US010864264B2

(12) United States Patent
Dormitzer et al.

(10) Patent No.: US 10,864,264 B2
(45) Date of Patent: Dec. 15, 2020

(54) INFLUENZA VIRUS REASSORTMENT

(71) Applicants: Seqirus UK Limited, Berkshire (GB); Synthetic Genomics, Inc., La Jolla, CA (US)

(72) Inventors: Philip Dormitzer, Cambridge, MA (US); Peter Mason, Cambridge, MA (US); Pirada Suphaphiphat, Cambridge, MA (US); Raul Gomila, Cambridge, MA (US)

(73) Assignees: Seqirus UK Limited, Maidenhead (GB); Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 16/657,082

(22) Filed: Oct. 18, 2019

(65) Prior Publication Data

US 2020/0215184 A1 Jul. 9, 2020

Related U.S. Application Data

(63) Continuation of application No. 16/258,816, filed on Jan. 28, 2019, now abandoned, which is a continuation of application No. 14/775,066, filed as application No. PCT/IB2014/059729 on Mar. 13, 2014, now Pat. No. 10,232,031.

(60) Provisional application No. 61/779,888, filed on Mar. 13, 2013.

(51) Int. Cl.

*A61K 39/145* (2006.01)
*A61K 39/00* (2006.01)
*C12N 7/00* (2006.01)
*A61K 39/12* (2006.01)
*C12N 7/02* (2006.01)

(52) U.S. Cl.

CPC ............ *A61K 39/145* (2013.01); *A61K 39/12* (2013.01); *C12N 7/00* (2013.01); *C12N 2760/16134* (2013.01); *C12N 2760/16234* (2013.01); *C12N 2760/16251* (2013.01); *C12N 2760/16252* (2013.01)

(58) Field of Classification Search

CPC ............ C12N 7/00; C12N 2760/16134; A61K 39/145; A61K 39/12; A61P 31/16
See application file for complete search history.

(56) References Cited

U.S. PATENT DOCUMENTS

2007/0231348 A1 10/2007 Kawaoka et al.

FOREIGN PATENT DOCUMENTS

CN 102257135 A 11/2011
CN 102666860 A 9/2012
JP 2011-527581 A 11/2011
WO WO 2002/024878 A2 3/2002
WO WO 2005/115448 A2 12/2005
WO WO 2006/098901 A2 9/2006
WO WO 2007/052056 A1 5/2007
WO WO 2010/006144 A2 1/2010
WO WO 2010/077986 A2 7/2010
WO WO 2011/012999 A1 2/2011

OTHER PUBLICATIONS

Hoffmaan et al., "Rescue of influenza B virus from eight plasmids", Proceeding of the national academy of sciences, 99(17), 2002: 11411-11416.*
GenBank Accession AFH57910, matrix protein 1 [Influenza B virus (B/Brisbane/60/2008)], Apr. 11, 2012.
GenBank Accession AFH57911, BM2 protein [Influenza B virus (B/Brisbane/60/2008)], Apr. 11, 2012.
GenBank Accession AFH57914, nucleoprotein [Influenza B virus (B/Brisbane/60/2008)], Apr. 11, 2012.
GenBank Accession AFH57915, nonstructural protein 1 [Influenza B virus (B/Brisbane/60/2008)], Apr. 11, 2012.
GenBank Accession AFH57916, nuclear export protein [Influenza B virus (B/Brisbane/60/2008)], Apr. 11, 2012.
GenBank Accession AFH57917, polymerase PA [Influenza B virus (B/Brisbane/60/2008)], Apr. 11, 2012.
GenBank Accession AFH57918, polymerase PB1 [Influenza B virus (B/Brisbane/60/2008)], Apr. 11, 2012.
GenBank Accession AFH57919, polymerase PB2 [Influenza B virus (B/Brisbane/60/2008)], Apr. 11, 2012.
Hoffmann et al., "Rescue of influenza B virus from eight plasmids," Proc Natl Acad Sci U S A, 99(17): 11411-11416, (2002).
Hiromoto et al., "Phylogenetic analysis of the three polymerase genes (PB1, PB2 and PA) of influenza B virus," J Gen Virol, 81(Pt 4): 929-937, (2000).
International Search Report for PCT/IB2014/059729, dated Sep. 19, 2014.
Lindstrom et al., "Comparative analysis of evolutionary mechanisms of the hemagglutinin and three internal protein genes of influenza B virus: multiple cocirculating lineages and frequent reassortment of the NP, M, and NS genes," J Virol, 73(5):4413-4426, (1999).
Onodera et al., "Development of the influenza B reassortant NYMC BX-35 for use as seed virus for influenza B vaccine production," Influenza and Other Respiratory Viruses 5 (Suppl. 1), 328-394.
Rota et al., "Antigenic and genetic characterization of the haemagglutinins of recent cocirculating strains of influenza B virus," J Gen Virol, 73( (Pt 10): 2737-2742, (1992).
Shiroh et al., "Development of the Influenza B Reassortant NYMC BX-35 for use as Seed Virus for Influenza B Vaccine Production," Influenza and Other Respiratory Viruses, vol. 5, pp. 392-394, (2011).
Tsai et al., "Increasing appearance of reassortant influenza B virus in Taiwan from 2002 to 2005," J Clin Microbiol, 44(8): 2705-2713, (2006).

* cited by examiner

*Primary Examiner* — Barry A Chestnut
(74) *Attorney, Agent, or Firm* — Finnegan, Henderson, Farabow, Garrett & Dunner, LLP

(57) ABSTRACT

New influenza donor strains for the production of reassortant influenza B viruses are provided.

42 Claims, 10 Drawing Sheets

Specification includes a Sequence Listing.

INFLUENZA VIRUS REASSORTMENT

This application claims the benefit of U.S. provisional application 61/779,888 filed 13 Mar. 2013, the complete contents of which are incorporated herein by reference.

This invention was made in part with Government support under grant no. HHSO10020100061C awarded by the Biomedical Advanced Research and Development Authority (BARDA). The Government has certain rights in the invention.

TECHNICAL FIELD

This invention is in the field of influenza B virus reassortment. Furthermore, it relates to manufacturing vaccines for protecting against influenza B viruses.

BACKGROUND ART

The most efficient protection against influenza infection is vaccination against circulating strains and it is important to produce influenza viruses for vaccine production as quickly as possible.

Wild-type influenza viruses often grow to low titres in eggs and cell culture. In order to obtain a better-growing virus strain for vaccine production it is possible to reassort the circulating vaccine strain with a faster-growing high-yield donor strain. This can be achieved by co-infecting a culture host with the circulating influenza strain and the high-yield donor strain and selecting for reassortant viruses which contain the hemagglutinin (HA) and neuraminidase (NA) segments from the vaccine strain and the other viral segments (i.e. those encoding PB1, PB2, PA, NP, $M_1$, $M_2$, $NS_1$ and $NS_2$) from the donor strain. Another approach is to reassort the influenza viruses by reverse genetics (see, for example references 1 and 2).

Whilst it is common practice to use reassortant influenza A strains in vaccine production, reassortant influenza B strains are not usually used because wild-type influenza B viruses usually provide adequate yields in eggs. Furthermore, wild-type influenza B viruses have been reported to have a growth advantage over reassortant influenza B viruses (see, for example, reference 3). Accordingly, high growth influenza B reassortants have been generated only for a small number of recent influenza B viruses. These reassortants typically contain a mixture of backbone gene segments derived from B/Lee/40, B/Brisbane/60/08 and B/Panama/45/90 (4, 5).

To date, only two reassortant influenza B viruses (BX-35 and BX-39) have been used for commercial vaccine manufacturing. BX-35 contains the HA, NA, PA, PB1, and NS segments from the B/Brisbane/60/08 strain, the PB2 and M segments from B/Panama/45/90, and the NP segment from B/Lee/40. BX-39 contains the HA, NA, PBI, and M segments from the circulating B/Hubei-Wujiagang/159/08 strain, the PA and NS segments from B/Panama/45/90, and the PB2 and NP segments from B/Lee/40(6, 7).

There are currently only a limited number of donor strains for reassorting influenza B viruses for vaccine manufacture and the known reassortant influenza B viruses do not always grow better than the parent strain. Thus, there is a need in the art to provide further and improved donor strains for influenza B virus reassortment.

SUMMARY OF PREFERRED EMBODIMENTS

The invention thus provides reassortant influenza B viruses which can grow at the same speed or faster in a culture host (particularly in cell culture) compared to the corresponding wild-type influenza B virus from which the HA segment is derived. For example, the inventors have surprisingly discovered that a reassortant influenza B virus which comprises the HA segment from a first influenza B virus and the NP and/or PB2 segment from a second influenza B virus which is a B/Victoria/2/87-like strain grows particularly well in cell culture and eggs. The B/Victoria/2/87-like strain may be B/Brisbane/60/08.

The invention also provides reassortant influenza B viruses comprising the HA segment from a first influenza B virus and the NP segment from a second influenza B virus which is not B/Lee/40 or B/Ann Arbor/1/66 or B/Panama/45/90. For example, the reassortant influenza B virus may have a NP segment which does not have the sequence of SEQ ID NOs: 33, 38, 39 or 43. The reassortant influenza B virus may also have a NP segment which does not encode the protein of SEQ ID NOs: 19, 23, 44 or 45. The inventors have discovered that reassortant influenza B viruses which comprise a NP segment from an influenza B virus other than B/Lee/40 or B/Ann Arbor/1/66 or B/Panama/45/90 can grow very well in a culture host. The reassortant influenza B virus may comprise both the NP and PB2 segments from the second influenza B virus. The second influenza B virus is preferably a B/Victoria/2/87-like strain. The B/Victoria/2/87-like strain may be B/Brisbane/60/08.

The inventors have also discovered that a reassortant influenza B virus comprising the HA segment from a B/Yamagata/16/88-like strain and at least one backbone segment from a B/Victoria/2/87-like strain can grow well in a culture host. The reassortant influenza B virus may comprise two, three, four, five or six backbone segments from the B/Victoria/2/87-like strain. In a preferred embodiment, the reassortant influenza B virus comprises all the backbone segments from the B/Victoria/2/87-like strain. The B/Victoria/2/87-like strain may be B/Brisbane/60/08.

The invention also provides a reassortant influenza B virus comprising viral segments from a B/Victoria/2/87-like strain and a B/Yamagata/16/88-like strain, wherein the ratio of segments from the B/Victoria/2/87-like strain and the B/Yamagata/16/88-like strain is 1:7, 2:6, 3:5, 4:4, 5:3, 6:2 or 7:1. A ratio of 7:1, 6:2, 4:4, 3:5 or 1:7, in particular a ratio of 4:4, is preferred because such reassortant influenza B viruses grow particularly well in a culture host. The B/Victoria/2/87-like strain may be B/Brisbane/60/08. The B/Yamagata/16/88-like strain may be B/Panama/45/90. In these embodiments, the reassortant influenza B virus usually does not comprise all backbone segments from the same influenza B donor strain.

Also provided is a reassortant influenza B virus which comprises:

a) the PA segment of SEQ ID NO: 11, the PB1 segment of SEQ ID NO: 12, the PB2 segment of SEQ ID NO: 13, the NP segment of SEQ ID NO: 14, the NS segment of SEQ ID NO: 16 and the M segment of SEQ ID NO: 15; or b) the PA segment of SEQ ID NO: 11, the PB1 segment of SEQ ID NO: 31, the PB2 segment of SEQ ID NO: 13, the NP segment of SEQ ID NO: 14, the NS segment of SEQ ID NO: 35 and the M segment of SEQ ID NO: 34; or c) the PA segment of SEQ ID NO: 11, the PB1 segment of SEQ ID NO: 31, the PB2 segment of SEQ ID NO: 32, the NP segment of SEQ ID NO: 14, the NS segment of SEQ ID NO: 16 and the M segment of SEQ ID NO: 15; or d) the PA segment of SEQ ID NO: 30, the PB1 segment of SEQ ID NO: 12, the PB2 segment of SEQ ID NO: 13, the NP segment of SEQ ID NO: 14, the NS segment of SEQ ID NO: 16 and the M segment of SEQ ID NO: 15, or e) the PA segment of SEQ ID NO: 11, the PB1 segment of SEQ ID NO: 12, the PB2 segment of SEQ ID NO: 13, the NP segment of SEQ ID NO: 14, the NS segment of SEQ ID NO: 35 and the M segment of SEQ ID NO: 34, or f) the PA segment of SEQ ID NO: 30, the PB1 segment of SEQ ID NO: 31, the PB2 segment of SEQ ID NO: 13, the NP segment of SEQ ID NO: 33, the NS segment of SEQ ID NO: 35 and the M segment of SEQ ID NO: 34, or g) the PA segment of SEQ ID NO: 30, the PB1 segment of SEQ ID NO: 31, the PB2 segment of SEQ ID NO: 32, the NP segment of SEQ ID NO: 14, the NS segment of SEQ ID NO: 35 and the M segment of SEQ ID NO: 34, or h) the PA segment of SEQ ID NO: 11, the PB1 segment of SEQ ID NO: 12, the PB2 segment of SEQ ID NO: 13, the NP segment of SEQ ID NO: 33, the NS segment of SEQ ID NO: 35 and the M segment of SEQ ID NO: 34, or i) the PA segment of SEQ ID NO: 11, the PB1 segment of SEQ ID NO: 12, the PB2 segment of SEQ ID NO: 32, the NP segment of SEQ ID NO: 14, the NS segment of SEQ ID NO: 35 and the M segment of SEQ ID NO: 34, or j) the PA segment of SEQ ID NO: 30, the PB1 segment of SEQ ID NO: 12, the PB2 segment of SEQ ID NO: 13, the NP segment of SEQ ID NO: 14, the NS segment of SEQ ID NO: 35 and the M segment of SEQ ID NO: 34, or k) the PA segment of SEQ ID NO: 30, the PB1 segment of SEQ ID NO: 31, the PB2 segment of SEQ ID NO: 13, the NP segment of SEQ ID NO: 14, the NS segment of SEQ ID NO: 35 and the M segment of SEQ ID NO: 34.

In these reassortant influenza B viruses, the HA and NA segments may be from any influenza B strain.

Reassortant influenza B viruses with the combinations of segments as discussed in section (a) to (k) above are preferred because the inventors have shown that they grow particularly well in culture hosts. The reassortant influenza B strains of sections (a), (b) and (e) grow particularly well in culture hosts and are therefore particularly preferred.

The invention also provides variants of the reassortant influenza B viruses identified in sections (a) to (k) above which comprise viral segments that have at least 97% identity, at least 98% identity, or at least 99% identity to the viral segments identified in these sections. Such variants can preferably grow to a viral titre in a culture host which is within 3% of the viral titre achieved with the reassortant influenza B strain from which the variant is derived in the same time and under the same growth conditions.

The invention provides methods of preparing the reassortant influenza B viruses of the invention. These methods comprise steps of (i) introducing into a culture host one or more expression construct(s) which encode(s) the viral segments required to produce a reassortant influenza B virus of the invention and (ii) culturing the culture host in order to produce the reassortant virus; and optionally (iii) purifying the virus obtained in step (ii).

These methods may further comprise steps of: (iv) infecting a culture host with the virus obtained in step (ii) or step (iii); (v) culturing the culture host from step (iv) to produce further virus; and optionally (vi) purifying the virus obtained in step (v).

Expression constructs which can be used in the methods of the invention are also provided.

For example, the expression construct(s) may encode a reassortant influenza B virus comprising the HA segment from a first influenza B virus and the NP and/or PB2 segment from a second influenza B virus which is a B/Victoria/2/87-like strain. The NP and PB2 segments may both be from the B/Victoria/2/87-like strain. The B/Victoria/2/87-like strain is preferably B/Brisbane/60/08.

The expression construct(s) may also encode a reassortant influenza B virus comprising the HA segment from a first influenza B virus and the NP segment from a second influenza B virus which is not B/Lee/40 or B/Ann Arbor/1/66 or B/Panama/45/90. For example, the expression construct(s) may not encode a NP segment with the sequence of SEQ ID NOs: 19, 23, 44 or 45. The NP and PB2 segments may both be from the second influenza B virus. The second influenza B virus may be a B/Victoria/2/87-like strain and is preferably B/Brisbane/60/08.

The “first influenza virus” and the “second influenza virus” are different to each other.

The expression construct(s) can encode a reassortant influenza B virus comprising viral segments from a B/Victoria/2/87-like strain and a B/Yamagata/16/88-like strain, wherein the ratio of segments from the B/Victoria/2/87-like strain and the B/Yamagata/16/88-like strain is 1:7, 2:6, 3:5, 4:4, 5:3, 6:2 or 7:1. A ratio of 7:1, 6:2, 4:4, 3:5 or 1:7, in particular a ratio of 4:4, is preferred. The B/Victoria/2/87-like strain may be B/Brisbane/60/08. The B/Yamagata/16/88-like strain may be B/Panama/45/90.

Also provided are expression construct(s) which encode(s) a reassortant influenza B virus as described above.

The invention provides an expression system comprising one or more expression construct(s) of the invention. The invention also provides a host cell comprising an expression system of the invention. These host cells can express an influenza B virus from the expression construct(s) in the expression system.

The invention also provides a method for producing influenza viruses comprising steps of (a) infecting a culture host with a reassortant virus of the invention; (b) culturing the host from step (a) to produce the virus; and optionally (c) purifying the virus obtained in step (b).

The invention also provides a method of preparing a vaccine, comprising the steps of (a) preparing a virus by the methods of any one of the embodiments described above and (b) preparing a vaccine from the virus.

Also provided is a method of preparing a vaccine from the reassortant influenza B virus of the invention.

The invention also provides a vaccine which can be obtained by the methods of the invention.

Reassortant Viruses

The reassortant influenza B strains of the invention contain viral segments from a vaccine strain and one or more donor strain(s). The vaccine strain is the influenza strain which provides the HA segment of the reassortant influenza B strain. The vaccine strain can be any strain and can vary from season to season.

A donor strain is an influenza B strain which provides one or more of the backbone segments (i.e. those encoding PB1, PB2, PA, NP, $M_1$, $M_2$, $NS_1$ and $NS_2$) of the influenza B strain. The NA segment may also be provided by a donor strain or it may be provided by the vaccine strain. The reassortant influenza B viruses of the invention may also comprise one or more, but not all, of the backbone segments from the vaccine strain. As the reassortant influenza B virus contains a total of eight segments, it will therefore contain x (wherein x is from 1-7) viral segments from the vaccine strain and 8-x viral segments from the one or more donor strain(s).

As mentioned above, the purpose of the invention is to provide reassortant influenza B strains which, once rescued, can grow to higher or similar viral titres in a culture host. Thus, the reassortant influenza B virus strains of the invention can grow to higher or similar viral titres in cell culture and/or in eggs in the same time (for example 12 hours, 24 hours, 48 hours or 72 hours) and under the same growth conditions compared to the wild-type vaccine strain. In particular, they can grow to higher or similar viral titres in MDCK cells (such as MDCK 33016) in the same time and under the same growth conditions compared to the wild-type vaccine strain. The viral titre can be determined by standard methods known to those of skill in the art. Usefully, the reassortant influenza B viruses of the invention may achieve a viral titre which is at least 5% higher, at least 10% higher, at least 20% higher, at least 50% higher, at least 100% higher, at least 200% higher, or at least 500% higher than the viral titre of the wild-type vaccine strain in the same time frame and under the same conditions. The reassortant influenza B viruses may also grow to similar viral titres in the same time and under the same growth conditions compared to the wild-type vaccine strain. A similar titre in this context means that the reassortant influenza B viruses grow to a titre which is within 3% of the viral titre achieved with the wild-type vaccine strain in the same time and under the same growth conditions (i.e. wild-type titre ±3%).

Influenza B viruses currently do not display different HA subtypes, but influenza B virus strains do fall into two distinct lineages. These lineages emerged in the late 1980s and have HAs which can be antigenically and/or genetically distinguished from each other [8]. Current influenza B virus strains are either B/Victoria/2/87-like or B/Yamagata/16/88-like. These strains are usually distinguished antigenically, but differences in amino acid sequences have also been described for distinguishing the two lineages e.g. B/Yamagata/16/88-like strains often (but not always) have HA proteins with deletions at amino acid residue 164, numbered relative to the 'Lee40' HA sequence [9]. In some embodiments, the reassortant influenza B viruses of the invention may comprise viral segments from a B/Victoria/2/87-like strain. They may comprise viral segments from a B/Yamagata/16/88-like strain. Alternatively, they may comprise viral segments from a B/Victoria/2/87-like strain and a B/Yamagata/16/88-like strain.

Where the reassortant influenza B virus comprises viral segments from two or more influenza B virus strains, these viral segments may be derived from influenza B strains which have related neuraminidases. For instance, the influenza B strains which provide the viral segments may both have a B/Victoria/2/87-like neuraminidase [10] or may both have a B/Yamagata/16/88-like neuraminidase. For example, two B/Victoria/2/87-like neuraminidases may both have one or more of the following sequence characteristics: (1) not a serine at residue 27, but preferably a leucine; (2) not a glutamate at residue 44, but preferably a lysine; (3) not a threonine at residue 46, but preferably an isoleucine; (4) not a proline at residue 51, but preferably a serine; (5) not an arginine at residue 65, but preferably a histidine; (6) not a glycine at residue 70, but preferably a glutamate; (7) not a leucine at residue 73, but preferably a phenylalanine; and/or (8) not a proline at residue 88, but preferably a glutamine. Similarly, in some embodiments the neuraminidase may have a deletion at residue 43, or it may have a threonine; a deletion at residue 43, arising from a trinucleotide deletion in the NA gene, which has been reported as a characteristic of B/Victoria/2/87-like strains, although recent strains have regained Thr-43 [10]. Conversely, of course, the opposite characteristics may be shared by two B/Yamagata/16/88-like neuraminidases e.g. S27, E44, T46, P51, R65, G70, L73, and/or P88. These amino acids are numbered relative to the 'Lee40' neuraminidase sequence [11]. The reassortant influenza B virus may comprise a NA segment with the characteristics described above. Alternatively, or in addition, the reassortant influenza B virus may comprise a viral segment (other than NA) from an influenza B strain with a NA segment with the characteristics described above.

The backbone viral segments of an influenza B virus which is a B/Victoria/2/87-like strain can have a higher level of identity to the corresponding viral segment from B/Victoria/2/87 than it does to the corresponding viral segment of B/Yamagata/16/88 and vice versa. For example, the NP segment of B/Panama/45/90 (which is a B/Yamagata/16/88-like strain) has 99% identity to the NP segment of B/Yamagata/16/88 and only 96% identity to the NP segment of B/Victoria/2/87.

Where the reassortant influenza B virus of the invention comprises a backbone viral segment from a B/Victoria/2/87-like strain, the viral segments may encode proteins with the following sequences. The PA protein may have at least 97% identity, at least 98%, at least 99% identity or 100% identity to the sequence of SEQ ID NO: 1. The PB1 protein may have at least 97% identity, at least 98%, at least 99% identity or 100% identity to the sequence of SEQ ID NO: 2. The PB2 protein may have at least 97%, at least 98%, at least 99% or 100% identity to the sequence of SEQ ID NO: 3. The NP protein may have at least 97% identity, at least 98%, at least 99% identity or 100% identity to the sequence of SEQ ID NO: 4. The $M_1$ protein may have at least 97% identity, at least 98%, at least 99% identity or 100% identity to the sequence of SEQ ID NO: 5. The $M_2$ protein may have at least 97% identity, at least 98%, at least 99% identity or 100% identity to the sequence of SEQ ID NO: 6. The $NS_1$ protein may have at least 97% identity, at least 98%, at least 99% identity or 100% identity to the sequence of SEQ ID NO: 7. The $NS_2$ protein may have at least 97% identity, at least 98%, at least 99% identity or 100% identity to the sequence of SEQ ID NO: 8. In some embodiments, the reassortant influenza B virus may also comprise all of these backbone segments.

Where the reassortant influenza B viruses of the invention comprise a backbone viral segment from a B/Yamagata/16/88-like strain, the viral segment may encode proteins with the following sequences. The PA protein may have at least 97% identity, at least 98%, at least 99% identity or 100% identity to the sequence of SEQ ID NO: 20. The PB1 protein may have at least 97% identity, at least 98%, at least 99% identity or 100% identity to the sequence of SEQ ID NO: 21. The PB2 protein may have at least 97%, at least 98%, at least 99% or 100% identity to the sequence of SEQ ID NO: 22. The NP protein may have at least 97% identity, at least 98%, at least 99% identity or 100% identity to the sequence of SEQ ID NO: 23. The $M_1$ protein may have at least 97% identity, at least 98%, at least 99% identity or 100% identity to the sequence of SEQ ID NO: 24. The $M_2$ protein may have at least 97% identity, at least 98%, at least 99% identity or 100% identity to the sequence of SEQ ID NO: 25. The $NS_1$ protein may have at least 97% identity, at least 98%, at least 99% identity or 100% identity to the sequence of SEQ ID NO: 26. The $NS_2$ protein may have at least 97% identity, at least 98%, at least 99% identity or 100% identity to the sequence of SEQ ID NO: 27.

The invention can be practised with donor strains having a viral segment that has at least about 70%, at least about 75%, at least about 80%, at least about 85%, at least about 90%, at least about 95% or at least about 99%, or 100% identity to a sequence of SEQ ID NOs 11-16 or 30-35. Due to the degeneracy of the genetic code, it is possible to have the same polypeptide encoded by several nucleic acids with different sequences. For example, the nucleic acid sequences of SEQ ID NOs: 40 and 41 have only 73% identity even though they encode the same viral protein. Thus, the invention may be practised with viral segments that encode the same polypeptides as the sequences of SEQ ID NOs 11-16 or 30-35.

In general a reassortant influenza virus will contain only one of each backbone segment. For example, when the influenza virus comprises the NP segment from B/Brisbane/60/08 it will not at the same time comprise the NP segment from another influenza strain.

In some embodiments, the reassortant influenza B virus of the invention may comprise all backbone segments from the same influenza B donor strain. It may alternatively comprise backbone segments from more than one influenza donor strain, for example from two, three, four or five donor strains. Where the reassortant influenza B virus comprises backbone segments from two or three donor strains, each donor strain may provide more than one of the backbone segments of the reassortant influenza B virus, but one or two of the donor strains can also provide only a single backbone segment. It is preferred that at least one of the backbone segments is from a B/Yamagata/16/88-like strain as the inventors have found that such reassortant influenza viruses grow well in cell culture. A preferred B/Yamagata/16/88-like strain in the context of the invention is B/Panama/45/90. In general the reassortant influenza B virus cannot comprise more than six backbone segments. Accordingly, for example, if one of the donor strains provides five of the viral segments, the reassortant influenza B virus can only comprise backbone segments from a total of two different influenza strains (for example, two donor strains or a donor strain and a vaccine strain).

When the reassortant influenza B virus comprises the backbone segments from a single donor strain, the reassortant viruses will generally include segments from the donor strain and the vaccine strain in a ratio of 1:7, 2:6, 3:5, 4:4, 5:3, 6:2 or 7:1. When the reassortant viruses comprise backbone segments from two donor strains, the reassortant virus can include segments from the first donor strain, the second donor strain and the vaccine strain in a ratio of 1:1:6, 1:2:5, 1:3:4, 1:4:3, 1:5:2, 1:6:1, 2:1:5, 2:2:4, 2:3:3, 2:4:2, 2:5:1, 3:1:4, 3:2:3, 3:3:2, 3:4:1, 4:1:3, 4:2:2, 4:3:1, 5:1:2, 5:2:1 or 6:1:1.

The reassortant influenza B viruses contain the HA segment from the vaccine strain as this encodes the main vaccine antigens of the influenza virus and therefore comes from the vaccine strain. The reassortant viruses of the invention preferably also have the NA segment from the vaccine strain, but the invention also encompasses reassortants which comprise the HA and NA segments from different strains.

Strains which can be used as vaccine strains include strains which are resistant to antiviral therapy (e.g. resistant to oseltamivir [12] and/or zanamivir), including resistant pandemic strains [13].

Reassortant viruses which contain an NS segment that does not encode a functional NS protein are also within the scope of the present invention. NS1 knockout mutants are described in reference 14. These NS1-mutant virus strains are particularly suitable for preparing live attenuated influenza vaccines.

Variations in the DNA and the amino acid sequence may stem from spontaneous mutations which can occur during passaging of the viruses. Such variant influenza strains can also be used in the invention.

Reverse Genetics

The invention is particularly suitable for producing the reassortant influenza B virus strains through reverse genetics techniques. In these techniques, the viruses are produced in culture hosts using one or more expression construct(s). The expression construct(s) may encode all the segments which are necessary to produce the reassortant influenza B viruses of the invention.

Reverse genetics for influenza viruses can be practised with 12 plasmids to express the four proteins required to initiate replication and transcription (PB1, PB2, PA and NP) and all eight viral genome segments. To reduce the number of constructs, however, a plurality of RNA polymerase I transcription cassettes (for viral RNA synthesis) can be included on a single plasmid (e.g. sequences encoding 1, 2, 3, 4, 5, 6, 7 or all 8 influenza vRNA segments), and a plurality of protein-coding regions with RNA polymerase II promoters on another plasmid (e.g. sequences encoding 1, 2, 3, 4, 5, 6, 7 or 8 influenza mRNA transcripts) [15]. It is also possible to include one or more influenza vRNA segments under control of a pol I promoter and one or more influenza protein coding regions under control of another promoter, in particular a pol II promoter, on the same plasmid. This is preferably done by using bi-directional plasmids.

Preferred aspects of the reference 15 method involve: (a) PB1, PB2, NP and PA mRNA-encoding regions on a single expression construct; and (b) all 8 vRNA encoding segments on a single expression construct. Including the neuraminidase (NA) and hemagglutinin (HA) segments on one expression construct and the six other viral segments on another expression construct is particularly preferred as newly emerging influenza virus strains usually have mutations in the NA and/or HA segments.

Therefore, the advantage of having the HA and/or NA segments on a separate expression construct is that only the vector comprising the HA and NA sequence needs to be replaced. Thus, in one aspect of the invention the NA and/or HA segments of the vaccine strain may be included on one expression construct and the vRNA encoding segments from the donor strain(s) of the invention, excluding the HA and/or NA segment(s), are included on a different expression construct. The invention thus provides an expression construct comprising one, two, three, four, five or six vRNA encoding backbone viral segments of a donor strain of the invention. The expression construct may not comprise HA and/or NA viral segments that produce a functional HA and/or NA protein.

Known reverse genetics systems involve expressing DNA molecules which encode desired viral RNA (vRNA) molecules from pol I promoters, bacterial RNA polymerase promoters, bacteriophage polymerase promoters, etc. As influenza viruses require the presence of viral polymerase to initiate the life cycle, systems may also provide these proteins e.g. the system further comprises DNA molecules that encode viral polymerase proteins such that expression of both types of DNA leads to assembly of a complete infectious virus. It is also possible to supply the viral polymerase as a protein.

Where reverse genetics is used for the expression of influenza vRNA, it will be evident to the person skilled in the art that precise spacing of the sequence elements with reference to each other is important for the polymerase to initiate replication. It is therefore important that the DNA molecule encoding the viral RNA is positioned correctly between the pol I promoter and the termination sequence, but this positioning is well within the capabilities of those who work with reverse genetics systems.

In order to produce a recombinant virus, a cell must express all segments of the viral genome which are necessary to assemble a virion. DNA cloned into the expression constructs of the present invention preferably provides all of the viral RNA and proteins, but it is also possible to use a helper virus to provide some of the RNA and proteins, although systems which do not use a helper virus are preferred. As the influenza virus is a segmented virus, the viral genome will usually be expressed using more than one expression construct in the methods of the invention. It is also envisioned, however, to combine one or more segments or even all segments of the viral genome on a single expression construct.

In some embodiments an expression construct will also be included which leads to expression of an accessory protein in the host cell. For instance, it can be advantageous to express a non-viral serine protease (e.g. trypsin) as part of a reverse genetics system.

Expression Constructs

Expression constructs used in the expression systems of the invention may be uni-directional or bi-directional expression constructs. Where more than one transgene is used in the methods (whether on the same or different expression constructs) it is possible to use uni-directional and/or bi-directional expression.

As influenza viruses require a protein for infectivity, it is generally preferred to use bi-directional expression constructs as this reduces the total number of expression constructs required by the host cell. Thus, the method of the invention may utilise at least one bi-directional expression construct wherein a gene or cDNA is located between an upstream pol II promoter and a downstream non-endogenous pol I promoter. Transcription of the gene or cDNA from the pol II promoter produces capped positive-sense viral mRNA which can be translated into a protein, while transcription from the non-endogenous pol I promoter produces negative-sense vRNA. The bi-directional expression construct may be a bi-directional expression vector.

Bi-directional expression constructs contain at least two promoters which drive expression in different directions (i.e. both 5' to 3' and 3' to 5') from the same construct. The two promoters can be operably linked to different strands of the same double stranded DNA. Preferably, one of the promoters is a pol I promoter and at least one of the other promoters is a pol II promoter. This is useful as the pol I promoter can be used to express uncapped vRNAs while the pol II promoter can be used to transcribe mRNAs which can subsequently be translated into proteins, thus allowing simultaneous expression of RNA and protein from the same construct. Where more than one expression construct is used within an expression system, the promoters may be a mixture of endogenous and non-endogenous promoters.

The pol I and pol II promoters used in the expression constructs may be endogenous to an organism from the same taxonomic order from which the host cell is derived. Alternatively, the promoters can be derived from an organism in a different taxonomic order than the host cell. The term “order” refers to conventional taxonomic ranking, and examples of orders are primates, rodentia, carnivora, marsupialia, cetacean, etc. Humans and chimpanzees are in the same taxonomic order (primates), but humans and dogs are in different orders (primates vs. carnivora). For example, the human pol I promoter can be used to express viral segments in canine cells (e.g. MDCK cells) [16].

The expression construct will typically include an RNA transcription termination sequence. The termination sequence may be an endogenous termination sequence or a termination sequence which is not endogenous to the host cell. Suitable termination sequences will be evident to those of skill in the art and include, but are not limited to, RNA polymerase I transcription termination sequence, RNA polymerase II transcription termination sequence, and ribozymes. Furthermore, the expression constructs may contain one or more polyadenylation signals for mRNAs, particularly at the end of a gene whose expression is controlled by a pol II promoter.

An expression system may contain at least two, at least three, at least four, at least five, at least six, at least seven, at least eight, at least nine, at least ten, at least eleven or at least twelve expression constructs.

An expression construct may be a vector, such as a plasmid or other episomal construct. Such vectors will typically comprise at least one bacterial and/or eukaryotic origin of replication. Furthermore, the vector may comprise a selectable marker which allows for selection in prokaryotic and/or eukaryotic cells. Examples of such selectable markers are genes conferring resistance to antibiotics, such as ampicillin or kanamycin. The vector may further comprise one or more multiple cloning sites to facilitate cloning of a DNA sequence.

As an alternative, an expression construct may be a linear expression construct. Such linear expression constructs will typically not contain any amplification and/or selection sequences. However, linear constructs comprising such amplification and/or selection sequences are also within the scope of the present invention. Reference 17 describes individual linear expression constructs for each viral segment. It is also possible to include more than one, for example two, three four, five or six viral segments on the same linear expression construct. Such a system has been described, for example, in reference 18. It is also possible to use an expression system in which some viral segments (for example the HA and/or NA segment) are encoded on a linear construct and the remaining viral segments (for example the backbone segments) are encoded on a non-linear construct, such as a vector, a plasmid or other episomal construct.

Expression constructs can be generated using methods known in the art. Such methods were described, for example, in reference 19. Where the expression construct is a linear expression construct, it is possible to linearise it before introduction into the host cell utilising a single restriction enzyme site. Alternatively, it is possible to excise the expression construct from a vector using at least two restriction enzyme sites. Furthermore, it is also possible to obtain a linear expression construct by amplifying it using a nucleic acid amplification technique (e.g. by PCR).

The expression constructs used in the systems of the invention may be non-bacterial expression constructs. This means that the construct can drive expression in a eukaryotic cell of viral RNA segments encoded therein, but it does not include components which would be required for propagation of the construct in bacteria. Thus the construct will not include a bacterial origin of replication (ori), and usually will not include a bacterial selection marker (e.g. an antibiotic resistance marker). Such expression constructs are described in reference 20.

The expression constructs may be prepared by chemical synthesis. The expression constructs may either be prepared entirely by chemical synthesis or in part. Suitable methods for preparing expression constructs by chemical synthesis are described, for example, in reference 20.

The expression constructs of the invention can be introduced into host cells using any technique known to those of skill in the art. For example, expression constructs can be introduced into host cells by employing electroporation, DEAE-dextran, calcium phosphate precipitation, liposomes, microinjection, or microparticle-bombardment. The expression construct(s) can be introduced into the same cell type which is subsequently used for the propagation of the reassortant influenza B viruses. Alternatively, the cells into which the expression constructs are introduced and the cells used for propagation of the reassortant influenza B viruses may be different. In some embodiments, untransfected cells of the same or a different cell type may be added to the host cells following transfection of the host cells with the expression construct(s), as described in reference 21.

Conventional Reassortment

Traditionally, influenza viruses are reassorted by co-infecting a culture host, usually eggs, with a donor strain and a vaccine strain. Reassortant viruses are selected by adding antibodies with specificity for the HA and/or NA proteins of the donor strain in order to select for reassortant viruses that contain the vaccine strain's HA and/or NA proteins. Over several passages of this treatment one can select for fast growing reassortant viruses containing the vaccine strain's HA and/or NA segments.

The reassortant influenza viruses can also be selected by adding an inhibitory agent which preferentially reduces the transcription and/or translation of the viral segments are not present in the desired reassortant influenza virus, as taught in WO2011/145081.

The invention is suitable for use in these methods. It can be easier to use a vaccine strain from a different influenza B lineage compared to the donor strain(s) as this facilitates selection for reassortant viruses. It is also possible, however, to use a vaccine strain from the same influenza B lineage as the donor strain(s) and in some aspects of the invention this preferred. In this case, antibodies or inhibitory agents with preferential specificity for the HA and/or NA proteins of the donor strain(s) should be available.

Culture Host

The culture host for use in the invention, can be any eukaryotic cell that can produce the virus of interest. The invention will typically use a cell line although, for example, primary cells may be used as an alternative. The cell will typically be mammalian or avian. Suitable mammalian cells include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [22-24]. Suitable dog cells are e.g. kidney cells, as in the CLDK and MDCK cell lines. Suitable avian embryonic stem cells, include the EBx cell line derived from chicken embryonic stem cells, EB45, EB14, and EB14-074 [25]. Chicken embryo fibroblasts (CEF) may also be used.

Further suitable cells include, but are not limited to: CHO; 293T; BHK; MRC 5; PER.C6 [26]; FRhL2; WI-38; etc. Suitable cells are widely available e.g. from the American Type Cell Culture (ATCC) collection [27], from the Coriell Cell Repositories [28], or from the European Collection of Cell Cultures (ECACC). For example, the ATCC supplies various different Vero cells under catalogue numbers CCL 81, CCL 81.2, CRL 1586 and CRL-1587, and it supplies MDCK cells under catalogue number CCL 34. PER.C6 is available from the ECACC under deposit number 96022940.

Preferred cells for use in the invention are MDCK cells [29-31], derived from Madin Darby canine kidney. The original MDCK cells are available from the ATCC as CCL 34. It is preferred that derivatives of MDCK cells are used. Such derivatives were described, for instance, in reference 29 which discloses MDCK cells that were adapted for growth in suspension culture ('MDCK 33016' or '33016-PF', deposited as DSM ACC 2219). Furthermore, reference 32 discloses MDCK-derived cells that grow in suspension in serum free culture ('B-702', deposited as FERM BP-7449). In some embodiments, the MDCK cell line used may be tumorigenic. It is also envisioned to use non-tumorigenic MDCK cells. For example, reference 33 discloses non tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (ATCC PTA-6503). Reference 34 discloses MDCK cells with high susceptibility to infection, including 'MDCK.5F1' cells (ATCC CRL 12042).

It is possible to use a mixture of more than one cell type to practise the methods of the invention. However, it is preferred that the methods of the invention are practised with a single cell type e.g. with monoclonal cells. Preferably, the cells used in the methods of the present invention are from a single cell line. Furthermore, the same cell line may be used for reassorting the virus and for any subsequent propagation of the virus.

Preferably, the cells are cultured in the absence of serum, to avoid a common source of contaminants. Various serum-free media for eukaryotic cell culture are known to the person skilled in the art (e.g. Iscove's medium, ultra CHO medium (BioWhittaker), EX-CELL (JRH Biosciences)). Furthermore, protein-free media may be used (e.g. PF-CHO (JRH Biosciences)). Otherwise, the cells for replication can also be cultured in the customary serum-containing media (e.g. MEM or DMEM medium with 0.5% to 10% of fetal calf serum).

The cells may be in adherent culture or in suspension.

The reassortant influenza B viruses of the invention may also be propagated using eggs as the culture host. The current standard method for influenza virus growth for vaccines uses embryonated hen eggs, with virus being purified from the egg contents (allantoic fluid). It is also possible to passage a virus through eggs and subsequently propagate it in cell culture and vice versa.

Virus Preparation

In one embodiment, the invention provides a method for producing influenza viruses comprising steps of (a) infecting a culture host with a reassortant virus of the invention; (b) culturing the host from step (a) to produce the virus; and optionally (c) purifying the virus produced in step (b).

The culture host in step (b) may be cells (as described above) or embryonated hen eggs. Where cells are used as a culture host in this aspect of the invention, it is known that cell culture conditions (e.g. temperature, cell density, pH value, etc.) are variable over a wide range subject to the cell line and the virus employed and can be adapted to the requirements of the application. The following information therefore merely represents guidelines.

Cells are preferably cultured in serum-free or protein-free media.

Multiplication of the cells can be conducted in accordance with methods known to those of skill in the art. For example, the cells can be cultivated in a perfusion system using ordinary support methods like centrifugation or filtration. Moreover, the cells can be multiplied according to the invention in a fed-batch system before infection. In the context of the present invention, a culture system is referred to as a fed-batch system in which the cells are initially cultured in a batch system and depletion of nutrients (or part of the nutrients) in the medium is compensated by controlled feeding of concentrated nutrients.

It can be advantageous to adjust the pH value of the medium during multiplication of cells before infection to a value between pH 6.6 and pH 7.8 and especially between a value between pH 7.2 and pH 7.3. Culturing of cells preferably occurs at a temperature between 30 and 40° C. When culturing the infected cells (step b), the cells are preferably cultured at a temperature of between 30° C. and 36° C. or between 32° C. and 34° C. or at 33° C. This is particularly preferred, as it has been shown that incubation of infected cells in this temperature range results in production of a virus that results in improved efficacy when formulated into a vaccine [35].

Oxygen partial pressure can be adjusted during culturing before infection preferably at a value between 25% and 95% and especially at a value between 35% and 60%. The values for the oxygen partial pressure stated in the context of the invention are based on saturation of air. Infection of cells occurs at a cell density of preferably about 8-25×$10^5$ cells/mL in the batch system or preferably about 5-20×$10^6$ cells/mL in the perfusion system. The cells can be infected with a viral dose (MOI value, "multiplicity of infection"; corresponds to the number of virus units per cell at the time of infection) between $10^{-8}$ and 10, preferably between 0.0001 and 0.5.

Virus may be grown on cells in adherent culture or in suspension. Microcarrier cultures can be used. In some embodiments, the cells may be adapted for growth in suspension.

The methods according to the invention also include harvesting and isolation of viruses or the proteins generated by them. During isolation of viruses or proteins, the cells are separated from the culture medium by standard methods like separation, filtration or ultrafiltration. The viruses or the proteins are then concentrated according to methods sufficiently known to those skilled in the art, like gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process.

Vaccine

Vaccines (particularly for influenza virus) are generally based either on live virus or on inactivated virus. Inactivated vaccines may be based on whole virions, 'split' virions, or on purified surface antigens. Antigens can also be presented in the form of virosomes. The invention can be used for manufacturing any of these types of vaccine but inactivated vaccines are preferred.

Where an inactivated virus is used, the vaccine may comprise whole virion, split virion, or purified surface antigens (for influenza, including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 36-41, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™ FLUARIX™, FLUZONE™ and FLUSHIELD™ products.

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

Another form of inactivated antigen is the virosome [42] (nucleic acid free viral-like liposomal particles). Virosomes can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

The methods of the invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate). Various forms of influenza virus vaccine are currently available (e.g. see chapters 17 & 18 of reference 43). Live virus vaccines include MedImmune's FLUMIST™ product.

The virus may be attenuated. The virus may be temperature-sensitive. The virus may be cold-adapted. These three features are particularly useful when using live virus as an antigen.

HA is the main immunogen in current inactivated influenza vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and ⅛ have been used, as have higher doses (e.g. 3× or 9× doses [44,45]). Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, etc. Particular doses include e.g. about 45, about 30, about 15, about 10, about 7.5, about 5, about 3.8, about 3.75, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^{65}$-$10^{75}$) per strain is typical.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

As well as being suitable for immunizing against inter-pandemic strains, the vaccines of the invention are particularly useful for immunizing against pandemic or potentially-pandemic strains. The invention is suitable for vaccinating humans as well as non-human animals.

Vaccines of the invention may include antigen(s) from one or more (e.g. 1, 2, 3, 4 or more) influenza virus strains, including influenza A virus and/or influenza B virus provided that at least one influenza strain is a reassortant influenza strain of the invention. Vaccines wherein two antigens are from a reassortant influenza strain of the invention are also envisioned. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [46], including antigens from two influenza A virus strains and two influenza B virus strains (preferably two influenza B strains of different lineages), or three influenza A virus strains and one influenza B virus strain. Where the influenza vaccine includes antigens from more than one influenza B strain one or more of these may be derived from a reassortant influenza B virus of the invention.

Vaccines of the invention are pharmaceutically acceptable. They usually include components in addition to the antigens e.g. they typically include one or more pharmaceutical carrier(s) and/or excipient(s). As described below, adjuvants may also be included. A thorough discussion of such components is available in reference 47.

Vaccines will generally be in aqueous form. However, some vaccines may be in dry form, e.g. in the form of injectable solids or dried or polymerized preparations on a patch.

Vaccines may include preservatives such as thiomersal or 2-phenoxyethanol. It is preferred, however, that the vaccine should be substantially free from (i.e. less than 5 μg/ml) mercurial material e.g. thiomersal-free [40,48]. Vaccines containing no mercury are more preferred. An α-tocopherol succinate can be included as an alternative to mercurial compounds [40]. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccines will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [49], but keeping osmolality in this range is nevertheless preferred.

Vaccines may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The vaccine is preferably sterile. The vaccine is preferably non-pyrogenic e.g. containing <1 EU (endotoxin unit, a standard measure) per dose, and preferably <0.1 EU per dose. The vaccine is preferably gluten-free.

Vaccines of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol-10 and polysorbate 80. Other residual components in trace amounts could be antibiotics (e.g. neomycin, kanamycin, polymyxin B).

A vaccine may include material for a single immunisation, or may include material for multiple immunisations (i.e. a 'multidose' kit). The inclusion of a preservative is preferred in multidose arrangements. As an alternative (or in addition) to including a preservative in multidose vaccines, the vaccines may be contained in a container having an aseptic adaptor for removal of material.

Influenza vaccines are typically administered in a dosage volume of about 0.5 ml, although a half dose (i.e. about 0.25 ml) may be administered to children.

Vaccines and kits are preferably stored at between 2° C. and 8° C. They should not be frozen. They should ideally be kept out of direct light.

Host Cell DNA

Where virus has been isolated and/or grown on a cell line, it is standard practice to minimize the amount of residual cell line DNA in the final vaccine, in order to minimize any potential oncogenic activity of the DNA.

Thus a vaccine of the invention preferably contains less than 10 ng (preferably less than 1 ng, and more preferably less than 100 pg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 50 & 51, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [52].

Adjuvants

Vaccines of the invention may advantageously include an adjuvant, which can function to enhance the immune responses (humoral and/or cellular) elicited in a subject who receives the vaccine. Preferred adjuvants comprise oil-in-water emulsions. Various such adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Another preferred oil is α-tocopherol (see below).

Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Where the vaccine contains a split virus, it is preferred that it contains free surfactant in the aqueous phase. This is advantageous as the free surfactant can exert a 'splitting effect' on the antigen, thereby disrupting any unsplit virions and/or virion aggregates that might otherwise be present. This can improve the safety of split virus vaccines [53].

Preferred emulsions have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [54-56], as described in more detail in Chapter 10 of ref. 57 and chapter 12 of ref. 58. The MF59 emulsion advantageously includes citrate ions e.g. 10 mM sodium citrate buffer.
- An emulsion comprising squalene, a tocopherol, and polysorbate 80. The emulsion may include phosphate buffered saline. These emulsions may have by volume from 2 to 10% squalene, from 2 to 10% tocopherol and from 0.3 to 3% polysorbate 80, and the weight ratio of squalene:tocopherol is preferably <1 (e.g. 0.90) as this can provide a more stable emulsion.

Squalene and polysorbate 80 may be present in a volume ratio of about 5:2 or at a weight ratio of about 11:5. Thus the three components (squalene, tocopherol, polysorbate 80) may be present at a weight ratio of 1068:1186:485 or around 55:61:25. One such emulsion ('AS03') can be made by dissolving Tween 80 in PBS to give a 2% solution, then mixing 90 ml of this solution with a mixture of (5 g of DL a tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d MPL). Another useful emulsion of this type may comprise, per human dose, 0.5-10 mg squalene, 0.5-11 mg tocopherol, and 0.1-4 mg polysorbate 80 [59] e.g. in the ratios discussed above.

- An emulsion of squalene, a tocopherol, and a Triton detergent (e.g. Triton X-100). The emulsion may also include a 3d-MPL (see below). The emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [60] (0.05-1% Thr-MDP, 5% squalane, 2.5% Pluronic L121 and 0.2% polysorbate 80). It can also be used without the Thr-MDP, as in the "AF" adjuvant [61] (5% squalane, 1.25% Pluronic L121 and 0.2% polysorbate 80). Microfluidisation is preferred.
- An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [62]. The emulsion may also include one or more of: alditol; a cryoprotective agent (e.g. a sugar, such as dodecylmaltoside and/or sucrose); and/or an alkylpolyglycoside. The emulsion may include a TLR4 agonist [63]. Such emulsions may be lyophilized
- An emulsion of squalene, poloxamer 105 and Abil-Care [64]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).
- An emulsion having from 0.5-50% of an oil, 0.1-10% of a phospholipid, and 0.05-5% of a non-ionic surfactant. As described in reference 65, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 66, produced by addition of aliphatic amine to desacylsaponin via the carboxyl group of glucuronic acid), dimethyidioctadecylammonium bromide and/or N,N-dioctadecyl-N, N-bis (2-hydroxyethyl)propanediamine.
- An emulsion in which a saponin (e.g. QuilA or QS21) and a sterol (e.g. a cholesterol) are associated as helical micelles [67].
- An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [68].
- An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [68].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids.

The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

Packaging of Vaccines

Suitable containers for vaccines of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colourless glass. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or vaccine may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

The invention provides a vaccine manufactured according to the invention. These vaccines are suitable for administration to human or non-human animal subjects, such as pigs or birds, and the invention provides a method of raising an immune response in a subject, comprising the step of administering a vaccine of the invention to the subject. The invention also provides a vaccine of the invention for use as a medicament, and provides the use of a vaccine of the invention for the manufacture of a medicament for raising an immune response in a subject.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [69]. Antibody responses are typically measured by hemagglutination inhibition, by microneutralisation, by single radial immunodiffusion (SRID), and/or by single radial hemolysis (SRH). These assay techniques are well known in the art.

Vaccines of the invention can be administered in various ways. The most preferred immunisation route is by intramuscular injection (e.g. into the arm or leg), but other available routes include subcutaneous injection, intranasal [70-72], oral [73], intradermal [74,75], transcutaneous, transdermal [76], etc.

Vaccines prepared according to the invention may be used to treat both children and adults. Influenza vaccines are currently recommended for use in pediatric and adult immunisation, from the age of 6 months. Thus a human subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), the young (e.g. ≤5 years old), hospitalised subjects, healthcare workers, armed service and military personnel, pregnant women, the chronically ill, immunodeficient subjects, subjects who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred vaccines of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced according to the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

The various steps of the methods may be carried out at the same or different times, in the same or different geographical locations, e.g. countries, and by the same or different people or entities.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 77. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 78.

References to a percentage sequence identity between two nucleic acid sequences mean that, when aligned, that percentage of bases are the same in comparing the two sequences. This alignment and the percent homology or sequence identity can be determined using software programs known in the art, for example those described in section 7.7.18 of reference 77. A preferred alignment program is GCG Gap (Genetics Computer Group, Wisconsin, Suite Version 10.1), preferably using default parameters, which are as follows: open gap=3; extend gap=1.

MODES FOR CARRYING OUT THE INVENTION

Development of New Donor Strains

Figure 1:
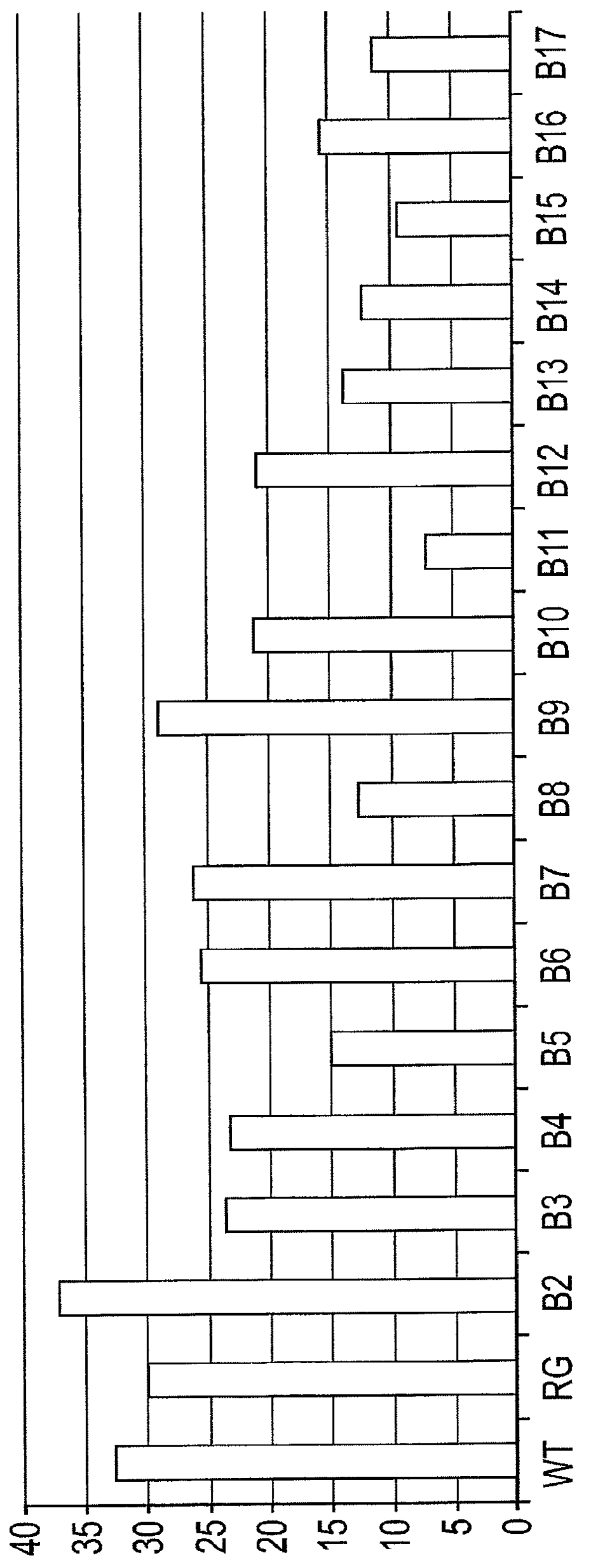
FIG. 1 compares the HA yield of different reassortant influenza B strains in MDCK cells relative to the wild-type (WT) or reverse genetics-derived (RG) B/Brisbane/60/08 strain. The viral segments of the tested influenza B viruses are shown in Table 1. The y-axis indicates the HA yield in μg/mL.

In order to provide high-growth donor strains, the inventors found that reassortant influenza B viruses comprising backbone segments from B/Brisbane/60/08 and B/Panama/45/90 grow particularly well in eggs and in cells, such as MDCK cells. To this end, reassortant influenza B viruses comprising backbone segments from these viruses are produced and the resulting influenza B viruses are grown in MDCK cells. The viral yield is determined by ELISA (as described in PCT/IB2012/057235) or a HA assay as known in the art.

Growth Characteristics of Reassortant Influenza B Viruses

Reassortant influenza B viruses are produced by reverse genetics which contain the HA and NA proteins from various influenza strains and the other viral segments from B/Brisbane/60/08 and/or B/Panama/45/90. As a control the corresponding wild-type influenza B strain is used. These viruses are cultured either in embyronated chicken eggs or in MDCK cells. The following influenza B strains are used:

TABLE 1

| | Backbone segments | | | | | | Antigenic determinants | |
|---|---|---|---|---|---|---|---|---|
| combo # | PA | PB1 | PB2 | NP | NS | M | HA | NA |
| 1 (WT) | Brisbane | Brisbane | Brisbane | Brisbane | Brisbane | Brisbane | Brisbane | Brisbane |
| 2 | Panama | Brisbane | Brisbane | Brisbane | Brisbane | Brisbane | Brisbane | Brisbane |
| 3 | Brisbane | Panama | Brisbane | Brisbane | Brisbane | Brisbane | Brisbane | Brisbane |
| 4 | Brisbane | Brisbane | Panama | Brisbane | Brisbane | Brisbane | Brisbane | Brisbane |
| 5 | Brisbane | Brisbane | Brisbane | Panama | Brisbane | Brisbane | Brisbane | Brisbane |
| 6 | Panama | Panama | Brisbane | Brisbane | Brisbane | Brisbane | Brisbane | Brisbane |
| 7 | Panama | Brisbane | Panama | Brisbane | Brisbane | Brisbane | Brisbane | Brisbane |
| 8 | Panama | Brisbane | Brisbane | Panama | Brisbane | Brisbane | Brisbane | Brisbane |
| 9 | Brisbane | Panama | Panama | Brisbane | Brisbane | Brisbane | Brisbane | Brisbane |
| 10 | Brisbane | Panama | Brisbane | Panama | Brisbane | Brisbane | Brisbane | Brisbane |
| 11 | Brisbane | Brisbane | Panama | Panama | Brisbane | Brisbane | Brisbane | Brisbane |
| 12 | Panama | Panama | Panama | Brisbane | Brisbane | Brisbane | Brisbane | Brisbane |
| 13 | Panama | Panama | Brisbane | Panama | Brisbane | Brisbane | Brisbane | Brisbane |
| 14 | Panama | Brisbane | Panama | Panama | Brisbane | Brisbane | Brisbane | Brisbane |
| 15 | Brisbane | Panama | Panama | Panama | Brisbane | Brisbane | Brisbane | Brisbane |
| 16 | Panama | Panama | Panama | Panama | Brisbane | Brisbane | Brisbane | Brisbane |
| 17 | Panama | Panama | Panama | Panama | Panama | Panama | Brisbane | Brisbane |
| 20 | Brisbane | Panama | Panama | Panama | Panama | Panama | Panama | Panama |
| 21 | Panama | Brisbane | Panama | Panama | Panama | Panama | Panama | Panama |
| 22 | Panama | Panama | Brisbane | Panama | Panama | Panama | Panama | Panama |
| 23 | Panama | Panama | Panama | Brisbane | Panama | Panama | Panama | Panama |
| 24 | Brisbane | Brisbane | Panama | Panama | Panama | Panama | Panama | Panama |
| 25 | Brisbane | Panama | Brisbane | Panama | Panama | Panama | Panama | Panama |
| 26 | Brisbane | Panama | Panama | Brisbane | Panama | Panama | Panama | Panama |
| 27 | Panama | Brisbane | Brisbane | Panama | Panama | Panama | Panama | Panama |
| 28 | Panama | Brisbane | Panama | Brisbane | Panama | Panama | Panama | Panama |
| 29 | Panama | Panama | Brisbane | Brisbane | Panama | Panama | Panama | Panama |
| 30 | Brisbane | Brisbane | Brisbane | Panama | Panama | Panama | Panama | Panama |
| 31 | Brisbane | Brisbane | Panama | Brisbane | Panama | Panama | Panama | Panama |
| 32 | Brisbane | Panama | Brisbane | Brisbane | Panama | Panama | Panama | Panama |
| 33 | Panama | Brisbane | Brisbane | Brisbane | Panama | Panama | Panama | Panama |
| 34 | Brisbane | Brisbane | Brisbane | Brisbane | Panama | Panama | Panama | Panama |
| 35 | Brisbane | Brisbane | Brisbane | Brisbane | Brisbane | Brisbane | Panama | Panama |

Figure 2:
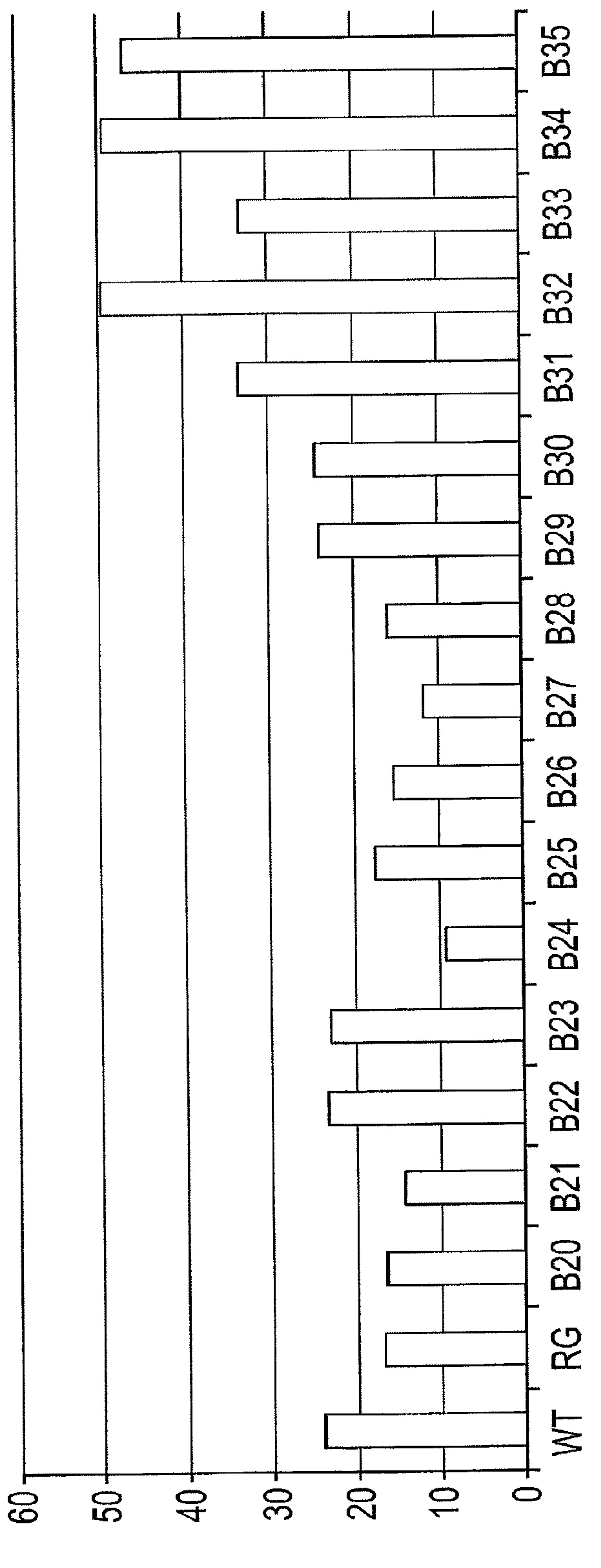
FIG. 2 compares the HA yield of different reassortant influenza B strains in MDCK cells relative to the wild-type (WT) or reverse genetics-derived (RG) B/Panama/45/90 strain. The viral segments of the tested influenza B viruses are shown in Table 1. The y-axis indicates the HA yield in μg/mL.
Figure 3A:
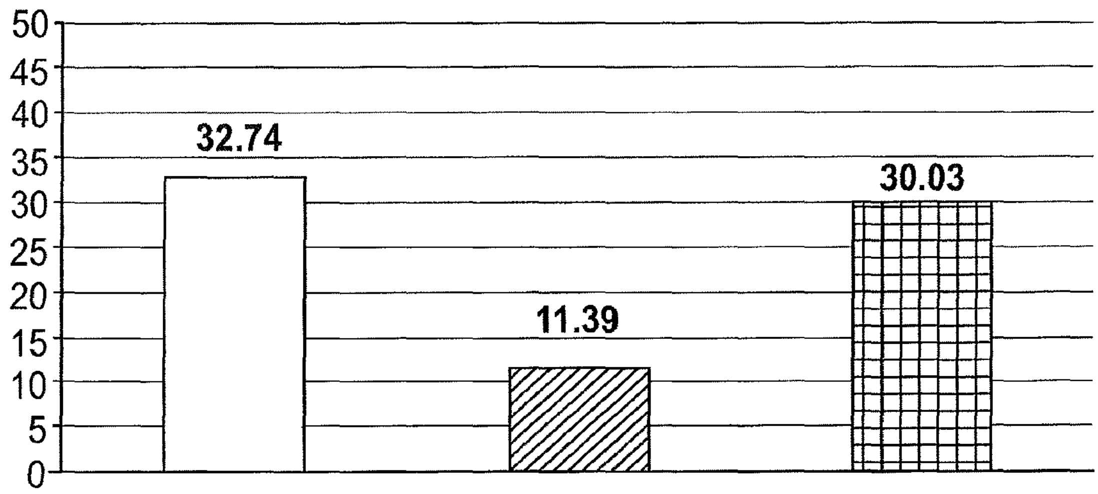
FIG. 3A, FIG. 3B, FIG. 3C, and FIG. 3D compare the HA yield of reassortant influenza B viruses comprising the B/Panama/45/90 or B/Brisbane/60/08 backbone with the HA yield obtained with the corresponding wild-type strain. The different experiments were performed using the B/Brisbane/60/08 HA and NA segments FIG. 3A, the B/Panama/45/90 HA and NA segments FIG. 3B, the B/Florida/4/06 HA and NA segments FIG. 3C or the B/Lee/40 HA and NA segments FIG. 3D. The white bar shows the results with wild-type-strain, the cross-hatched bar indicates the results with the B/Panama/45/90 backbone and the checked bar shows the results with the B/Brisbane/60/08 backbone. The y-axis in FIG. 3A, FIG. 3B, and FIG. 3C indicates the HA yield in μg/mL as determined by ELISA and the y-axis in FIG. 3D shows the HA titre as determined by HA assay.
Figure 3B:
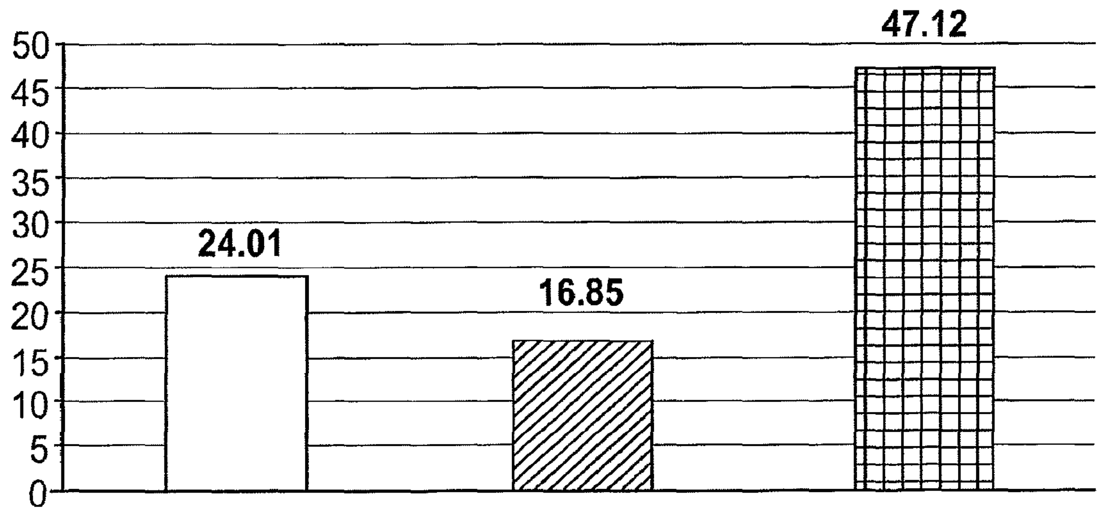
Figure 3C:
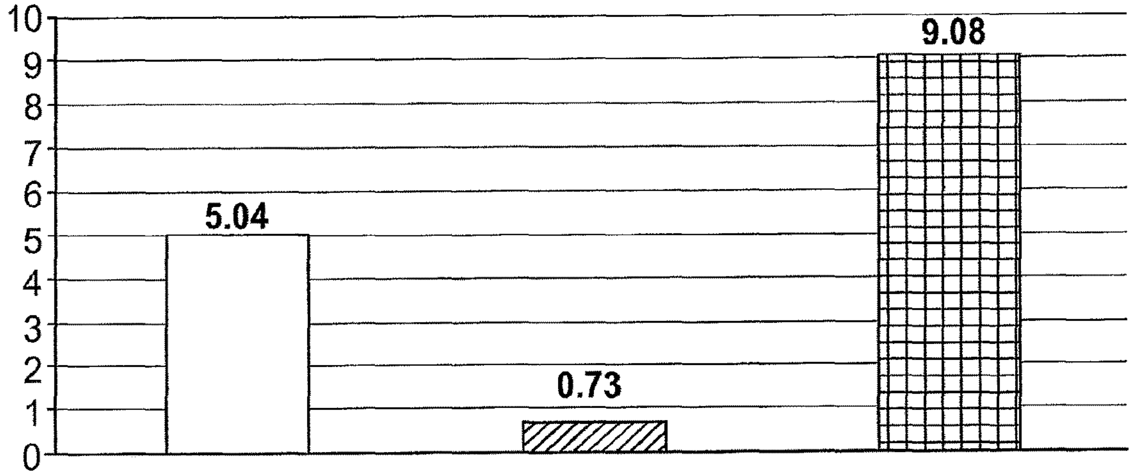
Figure 3D:
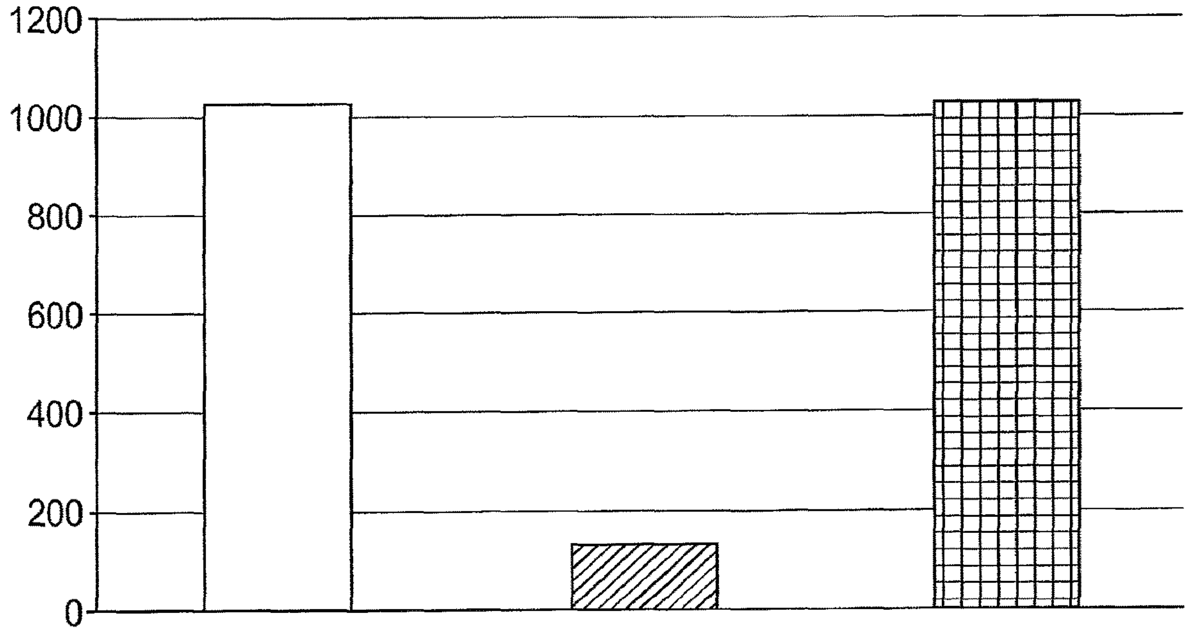
Figure 4A:
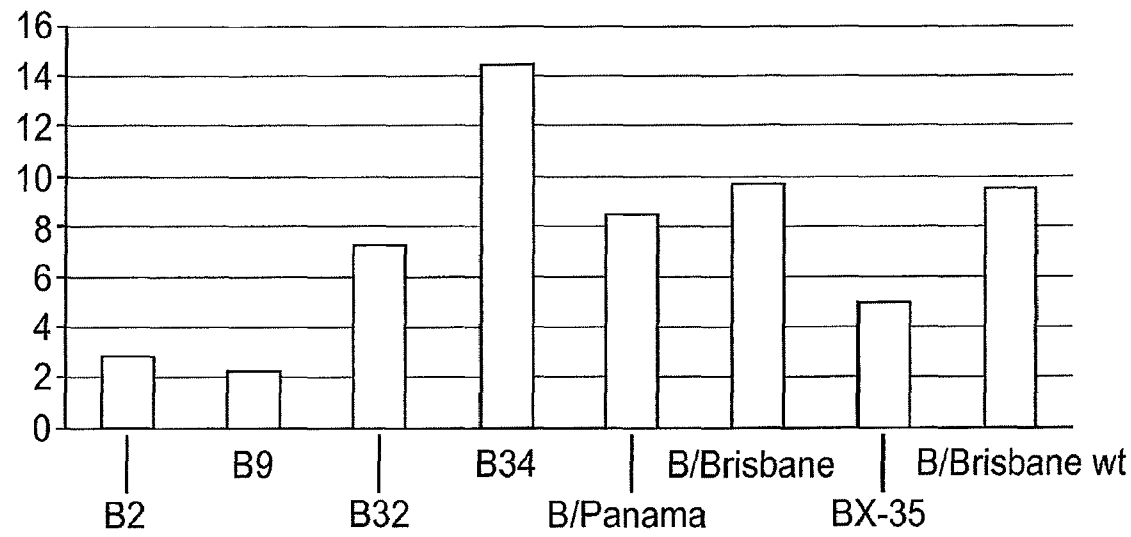
FIG. 4A, FIG. 4B, FIG. 4C, and FIG. 4D compare the HA yield of reassortant influenza B viruses comprising the #2, #9, #32, or #34 hybrid backbone (as shown in Table 1) with the HA yield obtained with the BX-35, B/Panama/45/90, or B/Brisbane/60/08 backbone or the corresponding wild-type virus. The different experiments were performed using the B/Brisbane/60/08 HA and NA segments FIG. 4A, the B/Panama/45/90 HA and NA segments FIG. 4B, the BX-35 HA and NA segments FIG. 4C or the B/Florida/4/06 HA and NA segments FIG. 4D. The y-axis indicates the HA yield in μg/mL.
Figure 4B:
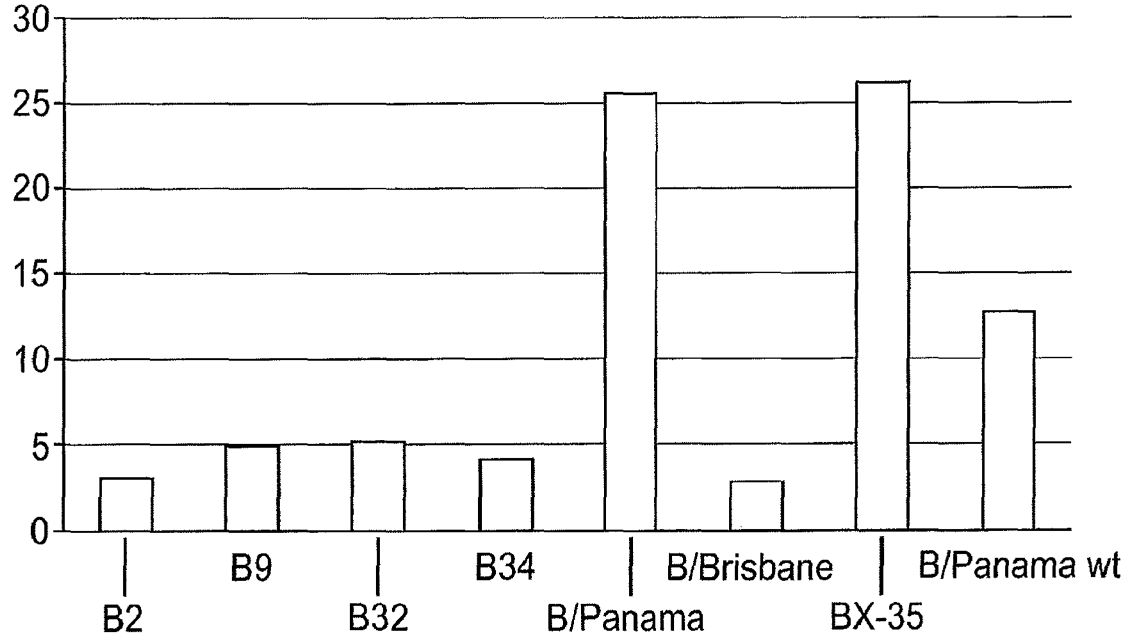
Figure 4C:
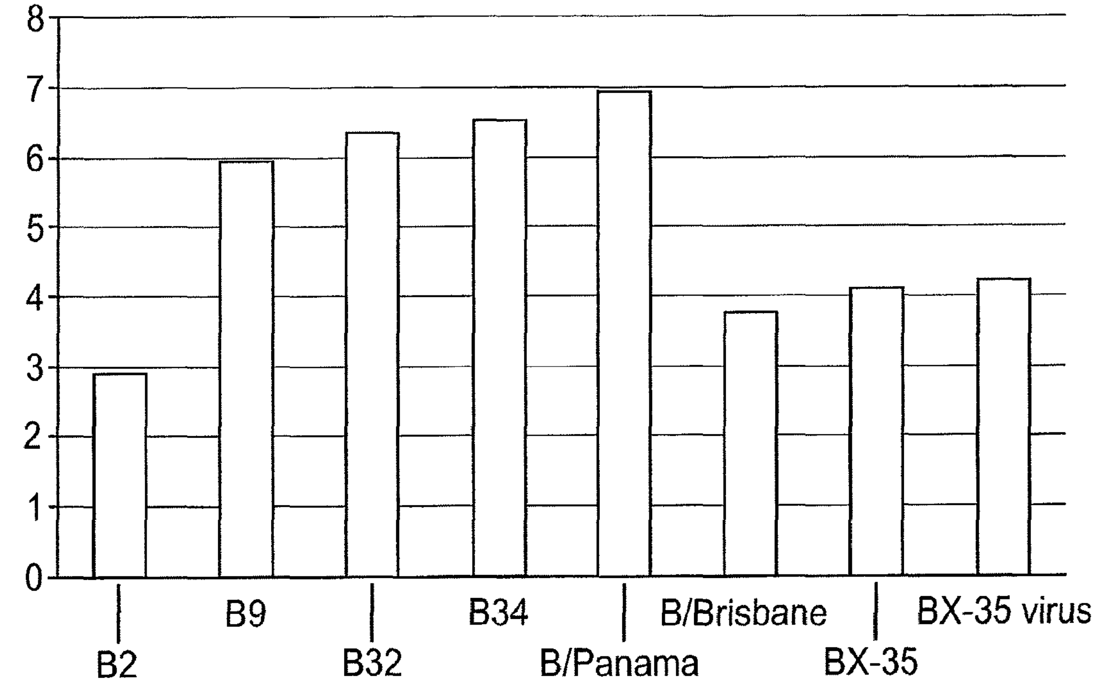
Figure 4D:
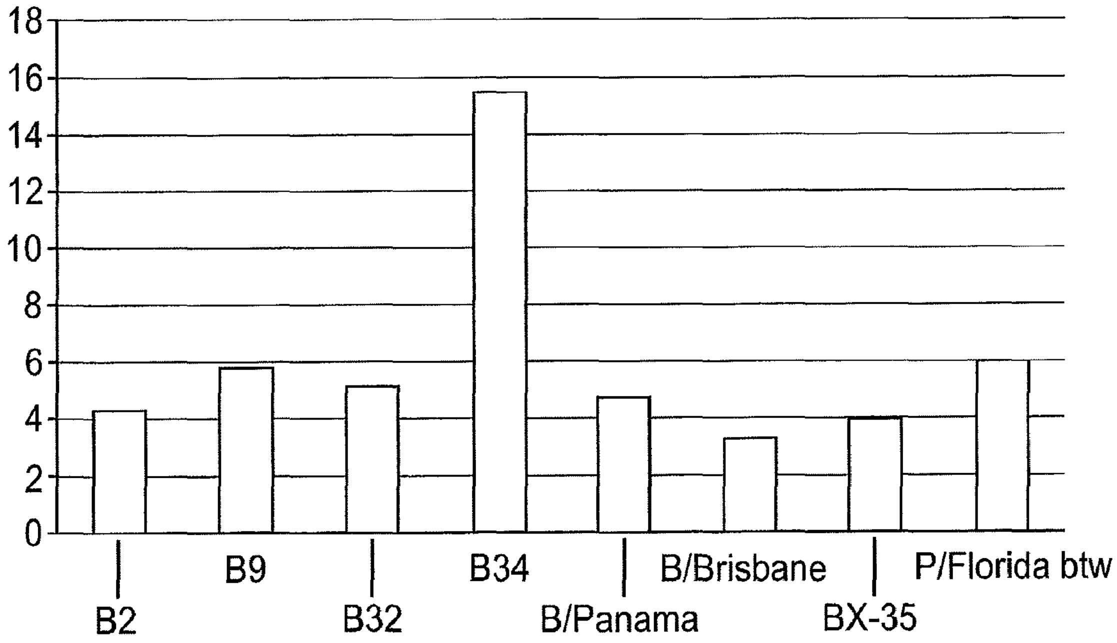
Figure 5A:
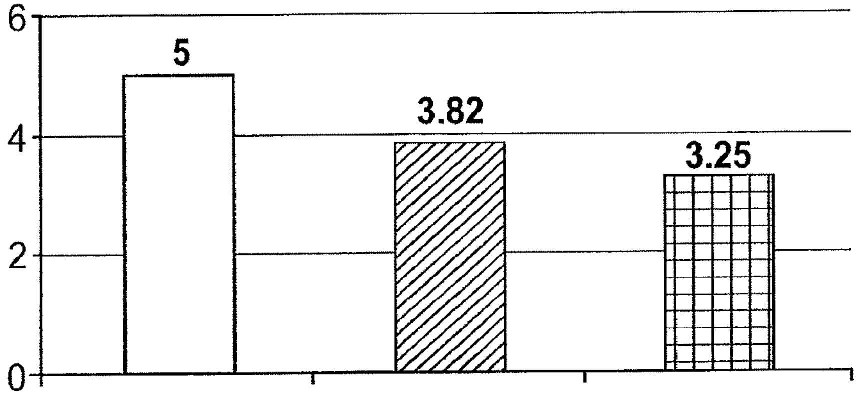
FIG. 5A, FIG. 5B, FIG. 5C, FIG. 5D, FIG. 5E, FIG. 5F, FIG. 5G, and FIG. 5H compare the HA yield of reassortant influenza B viruses comprising the #34 or B/Brisbane/60/08 backbones with the HA yield obtained with the corresponding wild-type strain. The different experiments were performed using the B/Panama/45/90 HA and NA segments FIG. 5A, the B/Brisbane/60/08 HA and NA segments FIG. 5B, the B/Florida/4/06 HA and NA segments FIG. 5C, the B/Brisbane/03/07 HA and NA segments FIG. 5D, the B/Brisbane/32/02 HA and NA segments FIG. 5E, the BX-35 HA and NA segments FIG. 5F, the B/Malaysia/2506/04 HA and NA segments FIG. 5G, or the B/Hubei-Wujiagang/159/08 HA and NA segments FIG. 5H. The white bar shows the results with the B/Brisbane/60/08 backbone, the cross-hatched bar indicates the results with the #34 backbone and the checked bar shows the results with the wild-type strain. The y-axis indicates the HA yield in μg/mL.
Figure 5B:
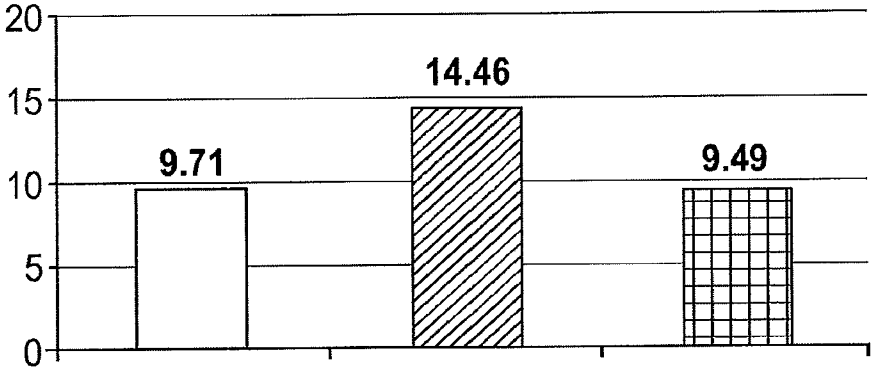
Figure 5C:
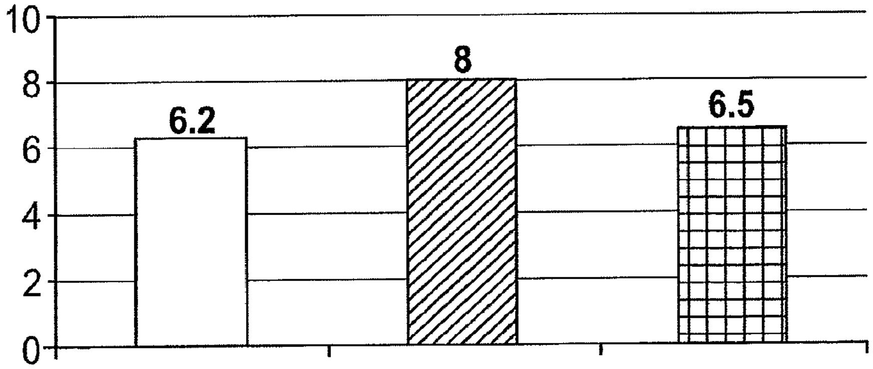
Figure 5D:
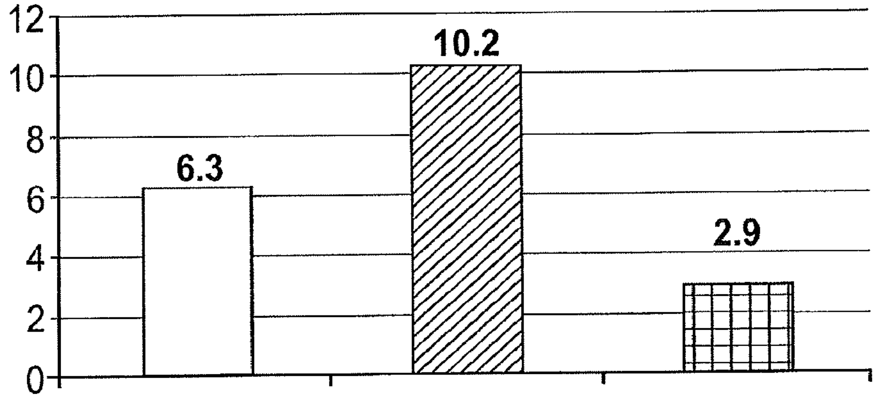
Figure 5E:
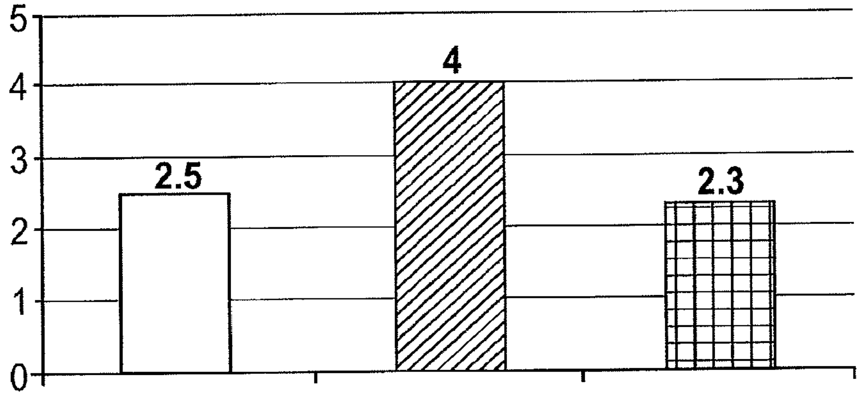
Figure 5F:
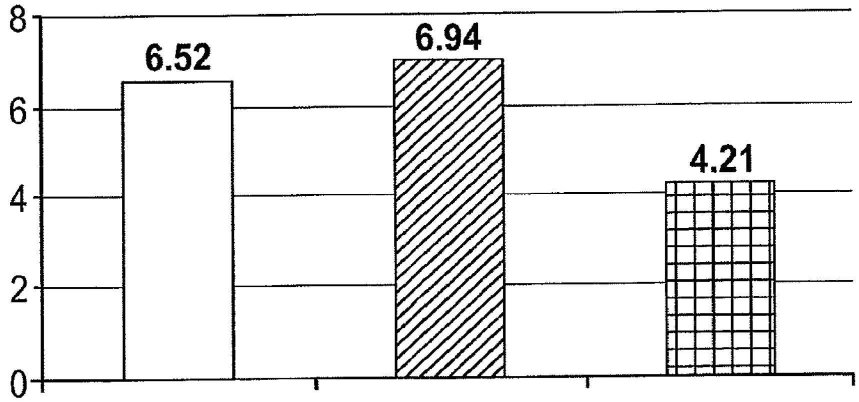
Figure 5G:
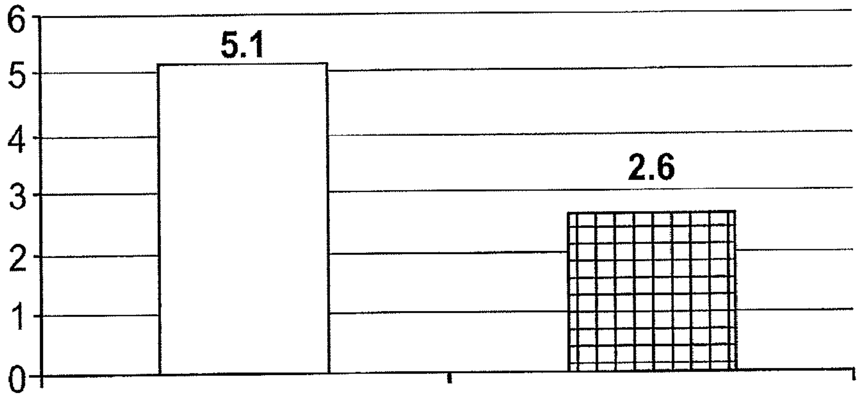
Figure 5H:
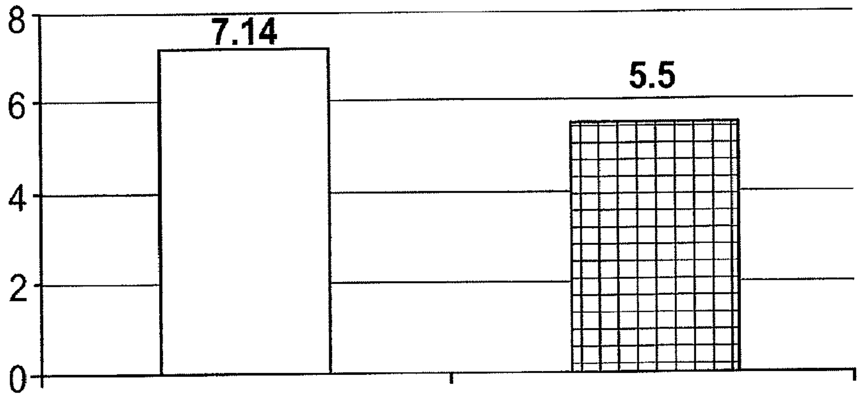

The results indicate that reassortant viruses #2, #9, #22, #23, #29, #30, #31, #32, #33, #34 and #35 grow equally well or even better in the culture host (see FIGS. 1 and 2) than the corresponding wild-type strain. Most of these strains comprise the NP segment from B/Brisbane/60/08 and some (in particular those which grew best) further contain the PB2 segment from B/Brisbane/60/08. All of these viruses also contain viral segments from the B/Victoria/2/87-like strain and the B/Yamagata/16/88-like strain at a ratio 7:1, 6:2, 4:4, 3:4 or 1:7.

Growth Characteristics of Reassortant Influenza B Viruses Comprising Backbone Segments From B/Brisbane/60/08

In order to test whether the reassortant influenza B viruses of the invention can be used with HA and NA segments from different strains, reassortant influenza B viruses comprising the HA and NA segments from B/Panama/45/90, B/Lee/40 or B/Florida/04/06 and the backbone segments from B/Brisbane/60/08 are produced. The reassortant influenza viruses are grown in MDCK cells for 60 hours and the HA yield is determined by ELISA or a HA assay. The data (see FIG. 3A, FIG. 3B, FIG. 3C, and FIG. 3D) show that all of the reassortant influenza B viruses grew to higher titres compared to the wild-type influenza B viruses which indicates that reassortant influenza B viruses of the invention are useful for a variety of different HA and NA segments.

Growth Characteristics of Reassortant Influenza B Viruses Comprising Hybrid Backbone Segments The growth characteristics of reassortant influenza B viruses comprising the backbone segments of the invention are also determined relative to the wild-type influenza B virus and the known influenza B reassortant BX35 which comprises the HA, NA, PA, PBI, and NS segments from B/Brisbane/60/08, the PB2 and M segments from B/Panama/45/90, and the NP segment from B/Lee/40. The backbones are tested with the HA and NA proteins of B/Brisbane/60/08, B/Panama/45/90, BX-35 and B/Florida/04/06. The reassortant influenza viruses are grown in MDCK cells for 60 hours and the HA yield is determined by ELISA or RP-HPLC. The data (see FIG. 4A, FIG. 4B, FIG. 4C, and FIG. 4D) show that reassortant influenza B viruses comprising the backbones of the invention can grow to higher titres compared to the wild-type and to reassortant influenza B viruses comprising the known BX35 backbone.

The HA yield obtained with the #34 and #35 is further tested using a number of different HA and NA segments. MDCK cells are infected with these reassortant influenza B viruses and the corresponding wild-type influenza B virus. The data (see FIG. 5A, FIG. 5B, FIG. 5C, FIG. 5D, FIG. 5E, FIG. 5F, FIG. 5G, and FIG. 5H) show that all of the reassortant influenza B viruses comprising a backbone according to the invention can grow equally well or better than the corresponding wild-type strain.

Growth Characteristics of Reassortant Influenza B Viruses in Eggs

Figure 6A:
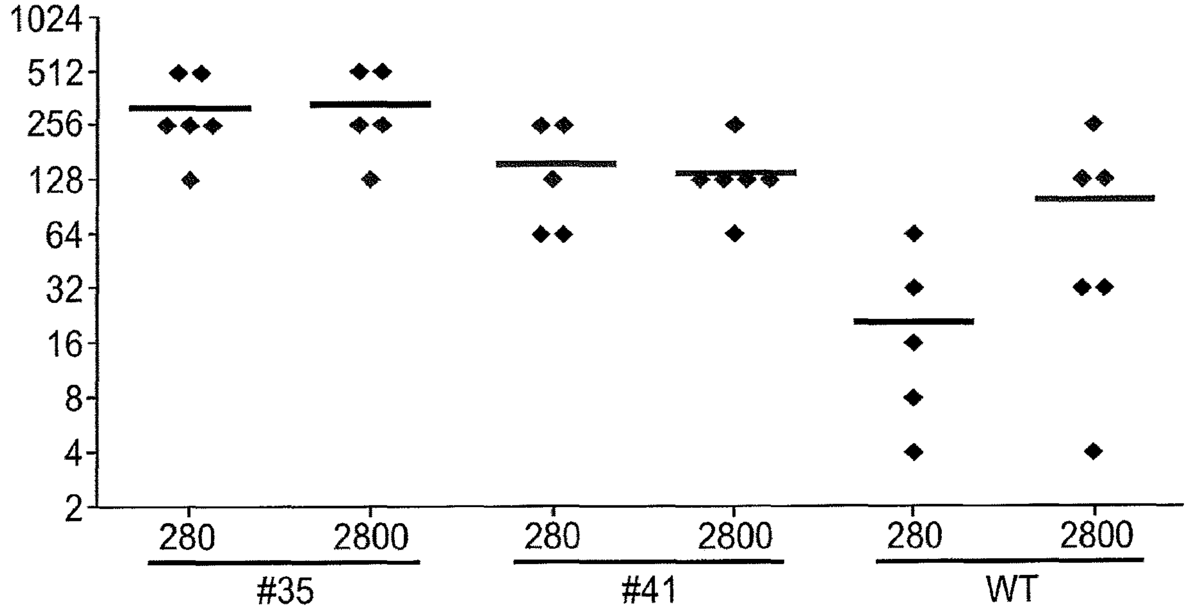
FIG. 6A and FIG. 6B compare the HA titre FIG. 6A and the viral growth FIG. 6B of (a) a reverse genetics-derived reassortant influenza B virus comprising all backbone segments from B/Brisbane/60/08 (#35) and the HA and NA segments from B/Wisconsin/1/10, (b) a reassortant influenza B virus which comprises the PB2, NP and M segments from B/Lee/40 and all other genes from B/Wisconsin/1/10 (#41), and (c) the wild-type B/Wisconsin/1/10 strain (WT) following growth in embryonated chicken eggs. Each triangle represents an individual egg and the bars represent mean values. "280" and "2800" indicate the infectious doses (IU) with which the eggs were inoculated. The y-axis in FIG. 6A represents the HA yield and the y-axis in FIG. 6B represents IU/mL.
Figure 6B:
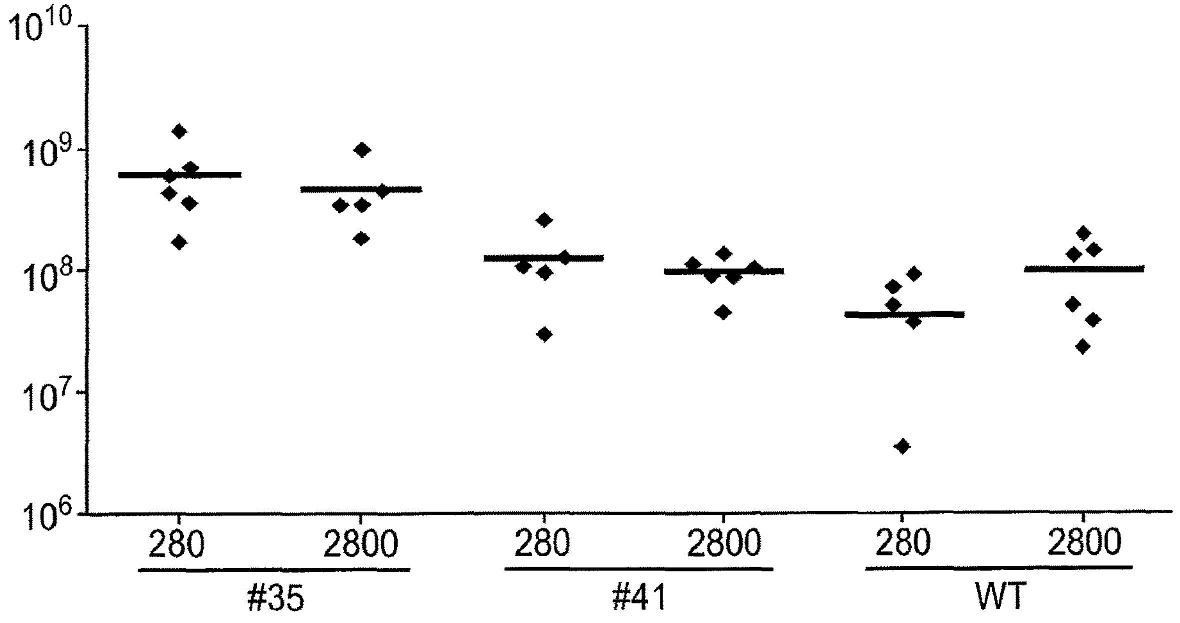

Embryonated chicken eggs were inoculated with either 280 or 2800 infectious doses (IU) of (a) a reverse genetics-derived reassortant influenza B virus comprising all backbone segments from B/Brisbane/60/08 (#35 backbone) and the HA and NA segments from B/Wisconsin/1/10, (b) a reassortant influenza B virus which comprises PB2, NP and M segments from B/Lee/40 and all other genes from B/Wisconsin/1/10 (BX-41), and (c) the wild-type B/Wisconsin/1/10 strain. Egg allantoic fluid was harvested 72h post-infection, and assayed for HA titer by HA Assay or virus growth by a focus-formation assay. The data (see FIG. 6A and FIG. 6B) show that the reassortant influenza B virus according to the invention can grow equally well or better than the control strains.

It will be understood that the invention has been described by way of example only and modifications may be made whilst remaining within the scope and spirit of the invention.

REFERENCES

[1] WO2007/002008
[2] WO2007/124327
[3] Goodeve et al. (1985) *Arch Virol.* 83(3-4):169-79.
[4] Audsley, J 2007, Alternative approaches in the preparation and growth of influenza B vaccine viruses, PhD Thesis, School of Applied Sciences, RMIT University.
[5] http://www.who.int/influenza/vaccines/virus/candidates_reagents/summary_b_cvv_20120621.pdf
[6] http://www.nibsc.ac.uk/documents/ifu/09-318.pdf
[7] http://www.nibsc.ac.uk/documents/ifu/12-202.pdf
[8] Rota et al. (1992) *J Gen Virol* 73:2737-42.
[9] GenBank sequence GI:325176.
[10] McCullers et al. (1999) *J Virol* 73:7343-8.
[11] GenBank sequence GI:325237.
[12] Herlocher et al. (2004) *J Infect Dis* 190(9):1627-30.
[13] Le et al. (2005) *Nature* 437(7062):1108.
[14] U.S. Pat. No. 6,468,544
[15] Neumann et al. (2005) Proc Natl Acad Sci USA 102:16825-9
[16] WO2010/133964
[17] WO2009/000891
[18] U.S. provisional application No. 61/273,151
[19] Sambrook et al, Molecular Cloning: A Laboratory Manual, 2 ed., 1989, Cold Spring Harbor Press, Cold Spring Harbor, N. Y
[20] WO2011/012999
[21] WO2011048560
[22] Kistner et al. (1998) Vaccine 16:960-8.
[23] Kistner et al. (1999) Dev Biol Stand 98:101-110.
[24] Bruhl et al. (2000) Vaccine 19:1149-58.
[25] WO2006/108846.
[26] Pau et al. (2001) Vaccine 19:2716-21.
[27] http://www.atcc.org/[28]
[28] http://locus.umdnj.edu/[29]
[29] WO97/37000.
[30] Brands et al. (1999) Dev Biol Stand 98:93-100.
[31] Halperin et al. (2002) Vaccine 20:1240-7.
[32] EP-A-1260581 (WO01/64846)
[33] WO2006/071563
[34] WO2005/113758
[35] WO97/37001
[36] WO02/28422.
[37] WO02/067983.
[38] WO02/074336.
[39] WO01/21151.
[40] WO02/097072.
[41] WO2005/113756.
[42] Huckriede et al. (2003) *Methods Enzymol* 373:74-91.
[43] Vaccines. (eds. Plotkins & Orenstein). 4th edition, 2004, ISBN: 0-7216-9688-0
[44] Treanor et al. (1996) *J Infect Dis* 173:1467-70.
[45] Keitel et al. (1996) *Clin Diagn Lab Immunol* 3:507-10.
[46] WO2008/068631.
[47] Gennaro (2000) *Remington: The Science and Practice of Pharmacy.* 20th edition, ISBN: 0683306472.
[48] Banzhoff (2000) *Immunology Letters* 71:91-96.
[49] Nony et al. (2001) *Vaccine* 27:3645-51.
[50] EP-B-0870508.
[51] U.S. Pat. No. 5,948,410.
[52] WO2007/052163.
[53] WO2007/052061
[54] WO90/14837.
[55] Podda & Del Giudice (2003) *Expert Rev Vaccines* 2:197-203.
[56] Podda (2001) *Vaccine* 19: 2673-2680.
[57] *Vaccine Design: The Subunit and Adjuvant Approach* (eds. Powell & Newman) Plenum Press 1995 (ISBN 0-306-44867-X).
[58] *Vaccine Adjuvants: Preparation Methods and Research Protocols* (Volume 42 of *Methods in Molecular Medicine* series). ISBN: 1-59259-083-7. Ed. O'Hagan.
[59] WO2008/043774.
[60] Allison & Byars (1992) *Res Immunol* 143:519-25.
[61] Hariharan et al. (1995) *Cancer Res* 55:3486-9.
[62] U.S.-2007/014805.
[63] U.S.-2007/0191314.
[64] Suli et al. (2004) *Vaccine* 22(25-26):3464-9.
[65] WO95/11700.
[66] U.S. Pat. No. 6,080,725.
[67] WO2005/097181.
[68] WO2006/113373.
[69] Potter & Oxford (1979) *Br Med Bull* 35: 69-75.
[70] Greenbaum et al. (2004) *Vaccine* 22:2566-77.
[71] Zurbriggen et al. (2003) *Expert Rev Vaccines* 2:295-304.
[72] Piascik (2003) *J Am Pharm Assoc* (Wash D.C.). 43:728-30.
[73] Mann et al. (2004) *Vaccine* 22:2425-9.
[74] Halperin et al. (1979) *Am J Public Health* 69:1247-50.
[75] Herbert et al. (1979) *J Infect Dis* 140:234-8.
[76] Chen et al. (2003) *Vaccine* 21:2830-6.
[77] *Current Protocols in Molecular Biology* (F. M. Ausubel et al., eds., 1987) Supplement 30.
[78] Smith & Waterman (1981) *Adv. Appl. Math.* 2: 482-489.

SEQUENCES
(PA, B/Brisbane/60/08)

SEQ ID NO: 1

MDTFITRNFQTTIIQKAKNTMAEFSEDPELQPAMLFNICVHLEVCYVISDMNFLDEEGKAYTALEGQGKEQNLRPQY

EVIEGMPRTIAWMVQRSLAQEHGIETPKYLADLFDYKTKRFIEVGITKGLADDYFWKKKEKLGNSMELMIFSYNQDY

-continued

SLSNESSLDEEGKGRVLSRLTELQAELSLKNLWQVLIGEEDVEKGIDFKLGQTISRLRDISVPAGFSNFEGMRSYID

NIDPKGAIERNLARMSPLVSVTPKKLTWEDLRPIGPHIYDHELPEVPYNAFLLMSDELGLANMTEGKSKKPKTLAKE

CLEKYSTLRDQTDPILIMKSEKANENFLWKLWRDCVNTISNEETSNELQKTNYAKWATGDGLTYQKIMKEVAIDDET

MCQEEPKIPNKCRVAAWVQTEMNLLSTLTSKRALDLPEIGPDIAPVEHVGSERRKYFVNEINYCKASTVMMKYVLFH

TSLLNESNASMGKYKVIPITNRVVNEKGESFDMLYGLAVKGQSHLRGDTDVVTVVTFEFSSTDPRVDSGKWPKYTVF

RIGSLFVSGREKSVYLYCRVNGTNKIQMKWGMEARRCLLQSMQQMEAIVEQESSIQGYDMTKACFKGDRVNSPKTFS

IGTQEGKLVKGSFGKALRVIFTKCLMHYVFGNAQLEGFSAESRRLLLLIQALKDRKGPWVFDLEGMYSGIEECISNN

PWVIQSVYWFNEWLGFEKEGNKVLESVDEIMDE (PB1, B/Brisbane/60/08)

SEQ ID NO: 2

MNINPYFLFIDVPVQAAISTTFPYTGVPPYSHGTGTGYTIDTVIRTHEYSNKGKQYISDVTGCTMVDPTNGPLPEDN

EPSAYAQLDCVLEALDRMDEEHPGLFQAASQNAMEALMVTTVDKLTQGRQTFDWTVCRNQPAATALNTTITSFRLND

LNGADKGGLIPFCQDIIDSLDRPEMTFFSVKNIKKKLPAKNRKGFLIKRIPMKVKDKITKVEYIKRALSLNTMTKDA

ERGKLKRRAIATAGIQIRGFVLVVENLAKNICENLEQSGLPVGGNEKKAKLSNAVAKMLSNCPPGGISMTVTGDNTK

WNECLNPRIFLAMTERITRDSPVWFRDFCSIAPVLFSNKIARLGKGFMITSKTKRLKAQIPCPDLFSIPLERYNEET

RAKLKKLKPFFNEEGTASLSPGMMMGMFNMLSTVLGVAALGIKNIGNKEYLWDGLQSSDDFALFVNAKDEETCMEGI

NDFYRTCKLLGVNMSKKKSYCNETGMFEFTSMFYRDGFVSNFAMELPSFGVAGVNESADMAIGMTIIKNNMINNGMG

PATAQTAIQLFIADYRYTYKCHRGDSKVEGKRMKIIKELWENTKGRDGLLVADGGPNIYNLRNLHIPEIVLKYNLMD

PEYKGRLLHPQNPFVGHLSIEGIKEADITPAHGPVKKMDYDAVSGTHSWRTKRNRSILNTDQRNMILEEQCYAKCCN

LFEACFNSASYRKPVGQHSMLEAMAHRLRMDARLDYESGRMSKDDFEKAMAHLGEIGYI (PB2, B/Brisbane/60/08)

SEQ ID NO: 3

MTLAKIELLKQLLRDNEAKTVLKQTTVDQYNIIRKFNTSRIEKNPSLRMKWAMCSNFPLALTKGDMANRIPLEYKGI

QLKTNAEDIGTKGQMCSIAAVTWWNTYGPIGDTEGFERVYESFFLRKMRLDNATWGRITFGPVERVRKRVLLNPLTK

EMPPDEASNVIMEILFPKEAGIPRESTWIHRELIKEKREKLKGTMITPIVLAYMLERELVARRRFLPVAGATSAEFI

EMLHCLQGENWRQIYHPGGNKLTESRSQSMIVACRKIIRRSIVASNPLELAVEIANKTVIDTEPLKSCLAAIDGGDV

ACDIIRAALGLKIRQRQRFGRLELKRISGRGFKNDEEILIGNGTIQKIGIWDGEEEFHVRCGECRGILKKSKMKLEK

LLINSAKKEDMRDLIILCMVFSQDTRMFQGVRGEINFLNRAGQLLSPMYQLQRYFLNRSNDLFDQWGYEESPKASEL

HGINESMNASDYTLKGIVVTRNVIDDFSSIETEKVSITKNLSLIKRTGEVIMGANDVSELESQAQLMITYDTPKMWE

MGTTKELVQNTYQWVLKNLVTLKAQFLLGKEDMFQWDAFEAFESIIPQKMAGQYSGFARAVLKQMRDQEVMKTDQFI

KLLPFCFSPPKLRSNGEPYQFLKLVLKGGGENFIEVRKGSPLFSYNPQTEVLTICGRMMSLKGKIEDEERNRSMGNA

VLAGFLVSGKYDPDLGDFKTIEELEKLKPGEKANILLYQGKPVKVVKRKRYSALSNDISQGIKRQRMTVESMGWALS (NP, B/Brisbane/60/08)

SEQ ID NO: 4

MSNMDIDGINTGTIDKTPEEITSGTSGTTRPIIRPATLAPPSNKRTRNPSPERATTSSEDDVGRKTQKKQTPTEIKK

SVYNMVVKLGEFYNQMMVKAGLNDDMERNLIQNAHAVERILLAATDDKKTEFQKKKNARDVKEGKEEIDHNKTGGTF

YKMVRDDKTIYFSPIRITFLKEEVKTMYKTTMGSDGFSGLNHIMIGHSQMNDVCFQRSKALKRVGLDPSLISTFAGS

TVPRRSGATGVAIKGGGTLVAEAIRFIGRAMADRGLLRDIKAKTAYEKILLNLKNKCSAPQQKALVDQVIGSRNPGI

ADIEDLTLLARSMVVVRPSVASKVVLPISIYAKIPQLGFNVEEYSMVGYEAMALYNMATPVSILRMGDDAKDKSQLF

FMSCFGAAYEDLRVLSALTGTEFKPRSALKCKGFHVPAKEQVEGMGAALMSIKLQFWAPMTRSGGNEVGGDGGSGQI

SCSPVFAVERPIALSKQAVRRMLSMNIEGRDADVKGNLLKMMNDSMAKKTSGNAFIGKKMFQISDKNKTNPIEIPIK

QTIPNFFFGRDTAEDYDDLDY

-continued ($M_1$, B/Brisbane/60/08)

SEQ ID NO: 5

MSLFGDTIAYLLSLTEDGEGKAELAEKLHCWFGGKEFDLDSALEWIKNKRCLTDIQKALIGASICFLKPKDQERKRR

FITEPLSGMGTTATKKKGLILAERKMRRCVSFHEAFEIAEGHESSALLYCLMVMYLNPGNYSMQVKLGTLCALCEKQ

ASHSHRAHSRAARSSVPGVRREMQMVSAMNTAKTMNGMGKGEDVQKLAEELQSNIGVLRSLGASQKNGEGIAKDVME

VLKQSSMGNSALVKKYL ($M_2$, B/Brisbane/60/08)

SEQ ID NO: 6

MLEPFQILTICSFILSALHFMAWTIGHLNQIKRGINMKIRIKGPNKETINREVSILRHSYQKEIQAKETMKEVLSDN

MEVLNDHIIIEGLSAEEIIKMGETVLEIEELH ($NS_1$, B/Brisbane/60/08)

SEQ ID NO: 7

MANNNMTTTQIEVGPGATNATINFEAGILECYERLSWQRALDYPGQDRLNRLKRKLESRIKTHNKSEPESKRMSLEE

RKAIGVKMMKVLLFMNPSAGIEGFEPYCMKSSSNSNCTKYNWTDYPSTPERCLDDIEEEPEDVDGPTEIVLRDMNNK

DARQKIKEEVNTQKEGKFRLTIKRDMRNVLSLRVLVNGTFLKHPNGHKSLSTLHRLNAYDQSGRLVAKLVATDDLTV

EDEEDGHRILNSLFERLNEGHSKPIRAAETAVGVLSQFGQEHRLSPEEGDN ($NS_2$, B/Brisbane/60/08)

SEQ ID NO: 8

MANNNMTTTQIEWRMKKMAIGSSTHSSSVLMKDIQSQFEQLKLRWESYPNLVKSTDYHQKRETIRLVTEELYLLSKR

IDDNILFHKTVIANSSIIADMVVSLSLLETLYEMKDVVEVYSRQCL (HA, B/Brisbane/60/08)

SEQ ID NO: 9

MKAIIVLLMVVTSNADRICTGITSSNSPHVVKTATQGEVNVTGVIPLTTTPTKSHFANLKGTETRGKLCPKCLNCTD

LDVALGRPKCTGKIPSARVSILHEVRPVTSGCFPIMHDRTKIRQLPNLLRGYEHIRLSTHNVINAENAPGGPYKIGT

SGSCPNITNGNGFFATMAWAVPKNDKNKTATNPLTIEVPYICTEGEDQITVWGEHSDNEAQMAKLYGDSKPQKFTSS

ANGVTTHYVSQIGGFPNQTEDGGLPQSGRIVVDYMVQKSGKTGTITYQRGILLPQKVWCASGRSKVIKGSLPLIGEA

DCLHEKYGGLNKSKPYYTGEHAKAIGNCPIWVKTPLKLANGTKYRPPAKLLKERGFFGAIAGFLEGGWEGMIAGWHG

YTSHGAHGVAVAADLKSTQEAINKITKNLNSLSELEVKNLQRLSGAMDELHNEILELDEKVDDLRADTISSQIELAV

LLSNEGIINSEDEHLLALERKLKKMLGPSAVEIGNGCFETKHKCNQTCLDRIAAGTFDAGEFSLPTFDSLNITAASL

NDDGLDNHTILLYYSTAASSLAVTLMIAIFVVYMVSRDNVSCSICL (NA, B/Brisbane/60/08)

SEQ ID NO: 10

MLPSTIQTLTLFLTSGGVLLSLYVSASLSYLLYSDILLKFSPTEITAPTMPLDCANASNVQAVNRSATKGVTLLLPE

PEWTYPRLSCPGSTFQKALLISPHRFGETKGNSAPLIIREPFIACGPNECKHFALTHYAAQPGGYYNGTRGDRNKLR

HLISVKLGKIPTVENSIFHMAAWSGSACHDGKEWTYIGVDGPDNNALLKVKYGEAYTDTYHSYANKILRTQESACNC

IGGNCYLMITDGSASGVSECRFLKIREGRIIKEIFPTGRVKHTEECTCGFASNKTIECACRDNSYTAKRPFVKLNVE

TDTAEIRLMCTDTYLDTPRPNDGSITGPCESNGDKGSGGIKGGFVHQRMESKIGRWYSRTMSKTERMGMGLYVKYDG

DPWADSDALAFSGVMVSMKEPGWYSFGFEIKDKKCDVPCIGIEMVHDGGKETWHSAATAIYCLMGSGQLLWDTVTGV

DMAL (PA, B/Brisbane/60/08)

SEQ ID NO: 11

AGCAGAAGCGGTGCGTTTGATTTGTCATAATGGATACTTTTATTACAAGAAACTTCCAGACTACAATAATACAAAAG

GCCAAAAACACAATGGCAGAATTTAGTGAAGATCCTGAATTGCAACCAGCAATGCTATTCAATATCTGCGTCCATCT

AGAGGTTTGCTATGTAATAAGTGACATGAATTTTCTTGACGAAGAAGGAAAAGCATATACAGCATTAGAAGGACAAG

GGAAAGAACAAAACTTGAGACCACAATATGAAGTAATTGAGGGAATGCCAAGAACCATAGCATGGATGGTCCAGAGA

TCCTTAGCTCAAGAGCATGGAATAGAGACTCCCAAGTATCTGGCTGATTTGTTTGATTATAAAACCAAAAGATTTAT

AGAAGTTGGAATAACAAAGGGATTGGCTGATGATTACTTTTGGAAAAAGAAAGAAAAGTTGGGAAATAGCATGGAAC

-continued

TGATGATATTCAGCTACAATCAAGACTACTCGTTAAGTAATGAATCCTCATTGGATGAGGAAGGGAAAGGGAGAGTG

CTAAGCAGACTCACAGAACTTCAGGCTGAATTAAGTCTGAAAAATTTATGGCAAGTTCTCATAGGAGAAGAAGATGT

TGAAAAGGGAATTGATTTTAAACTTGGACAAACAATATCTAGACTAAGGGATATATCTGTTCCAGCTGGTTTCTCCA

ATTTTGAAGGAATGAGGAGCTACATAGACAATATAGACCCAAAAGGAGCAATAGAGAGAAATCTAGCAAGGATGTCT

CCCTTAGTATCAGTCACACCTAAAAAGTTAACATGGGAGGACCTAAGACCAATAGGGCCTCACATTTACGACCATGA

GCTACCAGAAGTTCCATATAATGCCTTTCTTCTAATGTCTGATGAACTGGGATTGGCCAATATGACTGAGGGAAAGT

CCAAAAAACCGAAGACATTAGCCAAAGAATGTCTAGAAAAGTACTCAACACTACGGGATCAAACTGACCCAATATTA

ATAATGAAAAGCGAAAAAGCTAACGAAAATTTCCTATGGAAGCTTTGGAGAGACTGTGTAAATACAATAAGTAATGA

GGAAACGAGTAACGAGTTACAGAAAACCAATTATGCCAAATGGGCCACAGGGGATGGATTAACATACCAGAAAATAA

TGAAAGAAGTAGCAATAGATGACGAAACAATGTGCCAAGAAGAGCCTAAAATCCCTAACAAATGTAGAGTGGCTGCT

TGGGTTCAAACAGAGATGAATCTATTGAGCACTCTGACAAGTAAAAGAGCTCTGGACCTACCAGAAATAGGGCCAGA

CATAGCACCCGTGGAGCATGTAGGAAGTGAAAGAAGGAAATACTTTGTTAATGAAATCAACTACTGTAAGGCCTCTA

CAGTTATGATGAAGTATGTGCTTTTTCACACTTCATTGTTGAATGAAAGCAATGCCAGCATGGGAAAATACAAAGTA

ATACCAATAACCAATAGAGTAGTAAATGAAAAAGGAGAAAGTTTCGACATGCTTTACGGTCTGGCGGTTAAAGGACA

ATCTCATCTGAGGGGAGATACTGATGTTGTAACAGTTGTAACTTTCGAATTTAGTAGTACAGATCCAAGAGTGGACT

CAGGAAAGTGGCCAAAATATACTGTGTTTAGGATTGGCTCCCTATTTGTGAGTGGGAGGGAAAAATCTGTGTACTTG

TATTGCCGAGTGAATGGCACAAATAAGATCCAAATGAAATGGGGAATGGAAGCTAGAAGATGTTTGCTTCAATCAAT

GCAACAAATGGAGGCAATTGTTGAACAGGAATCATCAATACAAGGATATGACATGACCAAAGCCTGTTTCAAGGGAG

ACAGAGTAAATAGCCCCAAAACTTTCAGTATTGGAACTCAAGAAGGAAAACTAGTAAAAGGATCCTTTGGAAAAGCA

CTAAGAGTAATATTTACTAAATGCTTGATGCACTATGTATTTGGAAATGCCCAATTGGAGGGGTTTAGTGCCGAGTC

TAGGAGACTTCTACTGTTGATTCAAGCATTAAAGGACAGAAAGGGCCCTTGGGTGTTCGACTTAGAGGGAATGTATT

CTGGAATAGAAGAATGTATTAGCAACAACCCTTGGGTAATACAGAGTGTATACTGGTTCAATGAATGGTTGGGCTTT

GAAAAGGAGGGGAATAAAGTGTTGGAATCAGTGGATGAAATAATGGATGAATAAAAGGAAATGGTACTCAATTTGGT

ACTATTTTGTTCATTATGTATCTAAACATCCAATAAAAAGAACCAAGAATCAAAAATGCACGTGTTTCTACT (PB1, B/Brisbane/60/08)

SEQ ID NO: 12

AGCAGAAGCGGAGCCTTTAAGATGAATATAAATCCTTATTTTCTCTTCATAGATGTGCCCGTACAGGCAGCAATTTC

AACAACATTCCCATACACTGGTGTTCCCCCTTATTCCCATGGAACAGGAACAGGCTACACAATAGACACCGTGATCA

GAACGCATGAGTACTCAAACAAGGGGAAACAGTACATTTCTGATGTTACAGGATGCACAATGGTAGATCCAACAAAT

GGACCATTACCCGAAGATAATGAGCCGAGTGCCTATGCGCAATTAGATTGCGTTTTAGAGGCTTTGGATAGAATGGA

TGAAGAACACCCAGGTCTTTTTCAAGCAGCCTCACAGAATGCTATGGAGGCCCTAATGGTCACAACTGTAGACAAAT

TAACCCAGGGGAGACAGACTTTTGATTGGACAGTATGCAGAAACCAACCTGCTGCAACGGCACTGAACACAACAATA

ACCTCTTTTAGGTTGAATGATTTAAATGGAGCCGACAAAGGTGGATTAATACCTTTTTGCCAGGATATCATTGATTC

ATTAGACCGACCTGAAATGACTTTCTTCTCAGTAAAGAATATAAAGAAAAAATTGCCTGCCAAAAACAGAAAGGGTT

TCCTCATAAAGAGGATACCAATGAAGGTAAAAGACAAAATAACCAAAGTGGAATACATCAAAAGAGCATTATCATTA

AACACAATGACAAAAGACGCTGAAAGAGGCAAACTGAAAAGAAGAGCGATTGCCACTGCTGGAATACAAATCAGAGG

GTTTGTATTAGTAGTTGAAAACTTGGCTAAAAATATATGTGAAAATCTAGAACAAAGTGGTTTACCAGTAGGTGGAA

ACGAGAAGAAAGCCAAACTGTCAAACGCAGTGGCCAAAATGCTCAGTAACTGCCCACCAGGAGGGATTAGCATGACA

GTAACAGGAGACAATACAAAATGGAATGAATGTTTAAACCCAAGAATCTTTTTGGCTATGACTGAAAGAATAACCAG

AGACAGCCCAGTTTGGTTCAGGGATTTTTGTAGTATAGCACCGGTCCTGTTCTCCAATAAGATAGCAAGATTGGGGA

AAGGGTTTATGATAACAAGCAAAACAAAAAGACTGAAGGCTCAAATACCTTGTCCTGATCTGTTTAGTATACCGTTA

GAAAGATATAATGAAGAAACAAGGGCAAAATTGAAAAAGCTAAAACCATTCTTCAATGAAGAAGGAACTGCATCTTT

-continued

GTCGCCTGGGATGATGATGGGAATGTTTAATATGCTATCTACCGTGTTGGGAGTAGCTGCACTAGGTATCAAGAACA

TTGGAAACAAAGAATACTTATGGGATGGACTGCAATCTTCTGATGATTTTGCTCTGTTTGTTAATGCAAAGGATGAA

GAAACATGTATGGAAGGAATAAACGACTTTTACCGAACATGTAAATTATTGGGAGTAAACATGAGCAAAAAGAAAAG

TTACTGTAATGAGACTGGAATGTTTGAATTTACAAGCATGTTCTACAGAGATGGATTTGTATCTAATTTTGCAATGG

AACTCCCTTCGTTTGGGGTTGCTGGAGTAAATGAATCAGCAGATATGGCAATAGGAATGACAATAATAAAGAACAAC

ATGATCAACAATGGAATGGGTCCGGCAACAGCACAAACAGCCATACAGTTATTCATAGCTGATTATAGATACACCTA

CAAATGCCACAGGGGAGATTCCAAAGTAGAAGGAAAGAGAATGAAAATCATAAAGGAGTTATGGGAAAACACTAAAG

GAAGAGATGGTCTATTAGTAGCAGATGGTGGGCCCAACATTTACAATTTGAGAAACCTGCATATCCCAGAAATAGTA

TTAAAGTATAATCTAATGGACCCTGAATACAAAGGGCGGTTACTTCATCCTCAAAATCCCTTTGTGGGACATTTGTC

TATTGAGGGCATCAAAGAGGCAGACATAACCCCAGCACATGGTCCAGTAAAGAAAATGGACTACGATGCGGTGTCTG

GAACTCATAGTTGGAGAACCAAAAGAAACAGATCTATACTAAACACTGATCAGAGGAACATGATTCTTGAGGAACAA

TGCTACGCTAAATGTTGCAACCTATTTGAGGCCTGTTTTAACAGTGCATCATACAGGAAGCCAGTGGGTCAACATAG

CATGCTTGAGGCTATGGCCCACAGATTAAGAATGGATGCACGATTAGATTATGAATCAGGGAGAATGTCAAAGGATG

ATTTTGAGAAAGCAATGGCTCACCTTGGTGAGATTGGGTACATATAAGCTTCGAAGATGTTTATGGGGTTATTGGTC

ATCATTGAATACATGCGATACACAAATGATTAAAATGAAAAAAGGCTCGTGTTTCTACT (PB2, B/Brisbane/60/08)

SEQ ID NO: 13

AGCAGAAGCGGAGCGTTTTCAAGATGACATTGGCCAAAATTGAATTGTTAAAACAACTGCTAAGGGACAATGAAGCC

AAAACAGTTTTGAAGCAAACAACGGTAGACCAATATAACATAATAAGAAAATTCAATACATCAAGGATTGAAAAGAA

TCCTTCACTAAGGATGAAGTGGGCCATGTGTTCTAATTTTCCCTTGGCTCTAACCAAGGGCGATATGGCAAACAGAA

TCCCCTTGGAATACAAAGGGATACAACTTAAAACAAATGCTGAAGACATAGGAACCAAAGGCCAAATGTGCTCAATA

GCAGCAGTTACTTGGTGGAATACATATGGACCAATAGGAGATACTGAAGGTTTCGAAAGGGTCTACGAAAGCTTTTT

TCTCAGAAAAATGAGACTTGACAACGCCACTTGGGGCCGAATAACTTTTGGCCCAGTTGAAAGAGTGAGAAAAAGGG

TACTGCTAAACCCTCTCACCAAGGAAATGCCTCCGGATGAGGCGAGCAATGTGATAATGGAAATATTGTTCCCTAAA

GAAGCAGGAATACCAAGAGAATCCACTTGGATACATAGGGAACTGATAAAAGAAAAAAGAGAAAAATTGAAAGGAAC

AATGATAACTCCAATCGTACTGGCATACATGCTTGAAAGAGAACTGGTTGCTCGAAGAAGATTCTTGCCAGTGGCAG

GAGCAACATCAGCTGAGTTCATAGAAATGCTACACTGCTTACAAGGTGAAAATTGGAGACAAATATATCACCCAGGA

GGGAATAAATTAACTGAGTCCAGGTCTCAATCAATGATAGTAGCTTGTAGAAAAATAATCAGAAGATCAATAGTCGC

TTCAAACCCACTGGAGCTAGCTGTAGAAATTGCAAACAAGACTGTGATAGATACTGAACCTTTAAAGTCATGTCTGG

CAGCCATAGACGGAGGTGATGTAGCTTGTGACATAATAAGAGCTGCATTAGGACTAAAGATCAGACAAAGACAAAGA

TTTGGACGGCTTGAGCTAAAAAGAATATCAGGAAGAGGATTCAAAAATGATGAAGAAATATTAATAGGGAACGGAAC

AATACAGAAGATTGGAATATGGGACGGGGAAGAGGAGTTCCATGTAAGATGTGGTGAATGCAGGGGAATATTAAAAA

AGAGTAAAATGAAACTGGAAAAACTACTGATAAATTCAGCCAAAAAGGAGGATATGAGAGATTTAATAATCTTATGC

ATGGTATTTTCTCAAGACACTAGGATGTTCCAAGGAGTGAGAGGAGAAATAAATTTTCTTAATCGAGCAGGCCAACT

TTTATCTCCAATGTACCAACTCCAACGATATTTTTTGAATAGAAGCAACGACCTTTTTGATCAATGGGGGTATGAGG

AATCACCCAAAGCAAGTGAACTACATGGGATAAATGAATCAATGAATGCATCTGACTATACATTGAAAGGGATTGTA

GTGACAAGAAATGTAATTGACGACTTTAGCTCTATTGAAACAGAAAAAGTATCCATAACAAAAAATCTTAGTTTAAT

AAAAAGGACTGGGGAAGTCATAATGGGAGCTAATGACGTGAGTGAATTAGAATCACAAGCACAGCTGATGATAACAT

ATGATACACCTAAAATGTGGGAAATGGGAACAACCAAAGAACTGGTGCAAAACACTTATCAATGGGTGCTAAAAAAC

TTGGTGACACTGAAGGCTCAGTTTCTTCTAGGAAAAGAGGACATGTTCCAATGGGATGCATTTGAAGCATTTGAGAG

CATAATTCCTCAGAAGATGGCTGGTCAGTACAGTGGATTTGCAAGAGCAGTGCTCAAACAAATGAGAGACCAGGAGG

-continued

TTATGAAAACTGACCAGTTCATAAAGTTGTTGCCTTTTTGTTTCTCACCACCAAAATTAAGGAGCAATGGGGAGCCT

TATCAATTCTTAAAACTTGTGTTGAAAGGAGGAGGGGAAAATTTCATCGAAGTAAGGAAAGGGTCCCCTCTATTTTC

CTATAATCCACAAACAGAAGTCCTAACTATATGCGGCAGAATGATGTCATTAAAAGGGAAAATTGAAGATGAAGAAA

GGAATAGATCAATGGGTAATGCAGTATTAGCAGGCTTTCTCGTTAGTGGCAAGTATGACCCAGATCTTGGAGATTTC

AAAACTATTGAAGAACTTGAAAAGCTGAAACCGGGGGAAAAGGCAAACATCTTACTTTATCAAGGAAAACCAGTTAA

AGTAGTTAAAAGGAAAAGGTATAGTGCTTTGTCCAATGACATTTCACAAGGAATTAAGAGACAAAGAATGACAGTTG

AGTCTATGGGGTGGGCCTTGAGCTAATATAAATTTATCCATTAATTCAATGAACGCAATTGAGTGAAAAATGCTCGT

GTTTCTACT (NP, B/Brisbane/60/08)

SEQ ID NO: 14

AGCAGAAGCACAGCATTTTCTTGTGAACTTCAAGCACCAGTAAAAGAACTGAAAATCAAAATGTCCAACATGGATAT

TGACGGTATAAACACTGGGACAATTGACAAAACACCGGAAGAAATAACTTCTGGAACCAGTGGGACAACCAGACCAA

TCATTAGACCAGCAACCCTTGCCCCACCAAGCAACAAACGAACCCGTAACCCATCCCCGGAAAGAGCAACCACAAGC

AGTGAAGATGATGTCGGAAGGAAAACCCAAAAGAAACAGACCCCGACAGAGATAAAGAAGAGCGTCTACAACATGGT

GGTGAAACTGGGCGAATTCTATAACCAGATGATGGTCAAAGCTGGACTCAATGATGACATGGAGAGAAATCTAATCC

AAAATGCGCATGCCGTGGAAAGAATTCTATTGGCTGCCACTGATGACAAGAAAACCGAGTTCCAGAAGAAAAAGAAT

GCCAGAGATGTCAAAGAAGGGAAAGAAGAAATAGATCACAACAAAACAGGAGGCACCTTTTACAAGATGGTAAGAGA

TGATAAAACCATCTACTTCAGCCCTATAAGAATTACCTTTTTAAAAGAAGAGGTGAAAACAATGTACAAAACCACCA

TGGGGAGTGATGGCTTCAGTGGACTAAATCACATAATGATTGGGCATTCACAGATGAATGATGTCTGTTTCCAAAGA

TCAAAGGCACTAAAAAGAGTTGGACTTGATCCTTCATTAATCAGTACCTTTGCGGGAAGCACAGTCCCCAGAAGATC

AGGTGCGACTGGTGTTGCAATCAAAGGAGGTGGAACCTTAGTGGCTGAAGCCATTCGATTTATAGGAAGAGCAATGG

CAGACAGAGGGCTATTGAGAGACATCAAAGCCAAGACTGCCTATGAAAAGATTCTTCTGAATCTAAAAAACAAATGC

TCTGCGCCCCAACAAAAGGCTCTAGTTGATCAAGTGATCGGAAGCAGAAATCCGGGGATTGCAGACATTGAAGATCT

AACCCTGCTTGCTCGTAGTATGGTCGTTGTTAGGCCCTCTGTGGCAAGCAAAGTGGTGCTTCCCATAAGCATTTACG

CCAAAATACCTCAACTAGGGTTCAATGTTGAAGAGTACTCTATGGTTGGGTACGAAGCCATGGCTCTTTACAATATG

GCAACACCTGTGTCCATATTAAGAATGGGAGATGATGCAAAAGATAAATCGCAATTATTCTTCATGTCTTGCTTCGG

AGCTGCCTATGAAGACCTGAGAGTTTTGTCTGCATTAACAGGCACAGAATTCAAGCCTAGATCAGCATTAAAATGCA

AGGGTTTCCATGTTCCAGCAAAGGAACAGGTAGAAGGAATGGGAGCAGCTCTGATGTCCATCAAGCTCCAGTTTTGG

GCTCCGATGACCAGATCTGGGGGGAACGAAGTAGGTGGAGACGGAGGGTCTGGCCAAATAAGCTGCAGCCCAGTGTT

TGCAGTGGAAAGACCTATTGCTCTAAGCAAGCAAGCTGTAAGAAGAATGCTGTCAATGAATATTGAGGGACGTGATG

CAGATGTCAAAGGAAATCTACTCAAGATGATGAATGACTCAATGGCTAAGAAAACCAGTGGAAATGCTTTCATTGGG

AAGAAAATGTTTCAAATATCAGACAAAAACAAAACCAATCCCATTGAAATTCCAATTAAGCAGACCATCCCCAATTT

CTTCTTTGGGAGGGACACAGCAGAGGATTATGATGACCTCGATTATTAAGGCAACAAAATAGACACTATGACTGTGA

TTGTTTCAATACGTTTGGAATGTGGGTGTTTATTCTTATTAAAATAAATATAAAAAATGCTGTTGTTTCTACT (M, B/Brisbane/60/08)

SEQ ID NO: 15

AGCAGAAGCACGCACTTTCTTAAAATGTCGCTGTTTGGAGACACAATTGCCTACCTGCTTTCATTGACAGAAGATGG

AGAAGGCAAAGCAGAACTAGCAGAAAAATTACACTGTTGGTTTGGTGGGAAAGAATTTGACCTAGACTCTGCCTTGG

AATGGATAAAAAACAAAAGATGCTTAACTGATATACAAAAAGCACTAATTGGTGCCTCTATATGCTTTTTAAAACCC

AAAGACCAGGAAAGAAAAAGAAGATTCATCACAGAGCCCTTATCAGGAATGGGAACAACAGCAACAAAAAAGAAAGG

CCTGATTCTGGCTGAGAGAAAAATGAGAAGATGTGTGAGCTTTCATGAAGCATTTGAAATAGCAGAAGGCCATGAAA

GCTCAGCGCTACTATACTGTCTCATGGTCATGTACCTGAATCCTGGAAATTATTCAATGCAAGTAAAACTAGGAACG

CTCTGTGCTTTATGCGAGAAACAAGCATCACATTCACACAGGGCTCATAGCAGAGCAGCGAGATCTTCAGTGCCTGG

-continued

AGTGAGACGAGAAATGCAGATGGTCTCAGCTATGAACACAGCAAAAACAATGAATGGAATGGGAAAAGGAGAAGACG

TCCAAAAGCTGGCAGAAGAGTTGCAAAGCAACATTGGAGTGCTGAGATCTCTTGGGGCAAGCCAAAAGAATGGGGAA

GGGATTGCAAAGGATGTAATGGAAGTGCTAAAGCAGAGCTCCATGGGAAATTCAGCTCTTGTGAAGAAATATCTATA

ATGCTCGAACCATTTCAGATTCTTACAATTTGTTCTTTTATCTTATCAGCTCTCCATTTCATGGCTTGGACAATAGG

GCATTTGAATCAAATAAAAAGAGGAATAAACATGAAAATACGAATAAAAGGTCCAAACAAAGAGACAATAAACAGAG

AGGTATCAATTTTGAGACACAGTTACCAAAAAGAAATCCAGGCCAAAGAAACAATGAAGGAAGTACTCTCTGACAAC

ATGGAGGTATTGAATGACCACATAATAATTGAGGGGCTTTCTGCCGAAGAGATAATAAAAATGGGTGAAACAGTTTT

GGAGATAGAAGAATTGCATTAAATTCAATTTTACTGTATTTCTTACTATGCATTTAAGCAAATTGTAATCAATGTCA

GCAAATAAACTGGAAAAAGTGCGTTGTTTCTACT (NS, B/Brisbane/60/08)

SEQ ID NO: 16

AGCAGAAGCAGAGGATTTGTTTAGTCACTGGCAAACAGGGAAAAATGGCGAACAACAACATGACCACAACACAAATT

GAGGTGGGTCCGGGAGCAACCAATGCCACCATAAACTTTGAAGCAGGAATTCTAGAGTGCTATGAAAGGCTTTCATG

GCAAAGAGCCCTTGACTACCCTGGTCAAGACCGCCTAAACAGACTAAAGAGAAAATTAGAGTCAAGAATAAAGACTC

ACAACAAAAGTGAGCCTGAAAGTAAAAGGATGTCCCTTGAAGAGAGAAAAGCAATTGGAGTAAAAATGATGAAAGTA

CTCCTATTTATGAATCCGTCTGCTGGAATTGAAGGGTTTGAGCCATACTGTATGAAAAGTTCCTCAAATAGCAACTG

TACGAAATACAATTGGACTGATTACCCTTCAACACCAGAGAGGTGCCTTGATGACATAGAGGAAGAACCAGAGGATG

TTGATGGCCCAACTGAAATAGTATTAAGGGACATGAACAACAAAGATGCAAGGCAAAAGATAAAGGAGGAAGTAAAC

ACTCAGAAAGAAGGGAAGTTCCGTTTGACAATAAAAAGGGATATGCGTAATGTATTGTCCTTGAGAGTGTTGGTAAA

CGGAACATTCCTCAAACACCCCAATGGACACAAGTCCTTATCAACTCTGCATAGATTGAATGCATATGACCAGAGTG

GAAGGCTTGTTGCTAAACTTGTTGCCACTGATGATCTTACAGTGGAGGATGAAGAAGATGGCCATCGGATCCTCAAC

TCACTCTTCGAGCGTCTTAATGAAGGACATTCAAAGCCAATTCGAGCAGCTGAAACTGCGGTGGGAGTCTTATCCCA

ATTTGGTCAAGAGCACCGATTATCACCAGAAGAGGGAGACAATTAGACTGGTCACGGAAGAACTTTATCTTTTAAGT

AAAAGAATTGATGATAACATACTATTCCACAAAACAGTAATAGCTAACAGCTCCATAATAGCTGACATGGTTGTATC

ATTATCATTATTAGAAACATTGTATGAAATGAAGGATGTGGTTGAAGTGTACAGCAGGCAGTGCTTGTGAATTTAAA

ATAAAAATCCTCTTGTTACTACT (HA, B/Brisbane/60/08)

SEQ ID NO: 17

AGCAGAAGCAGAGCATTTTCTAATATCCACAAAATGAAGGCAATAATTGTACTACTCATGGTAGTAACATCCAATGC

AGATCGAATCTGCACTGGGATAACATCGTCAAACTCACCACATGTCGTCAAAACTGCTACTCAAGGGGAGGTCAATG

TGACTGGTGTAATACCACTGACAACAACACCCACCAAATCTCATTTTGCAAATCTCAAAGGAACAGAAACCAGGGGG

AAACTATGCCCAAAATGCCTCAACTGCACAGATCTGGACGTAGCCTTGGGCAGACCAAAATGCACGGGGAAAATACC

CTCGGCAAGAGTTTCAATACTCCATGAAGTCAGACCTGTTACATCTGGGTGCTTTCCTATAATGCACGACAGAACAA

AAATTAGACAGCTGCCTAACCTTCTCCGAGGATACGAACATATCAGGTTATCAACCCATAACGTTATCAATGCAGAA

AATGCACCAGGAGGACCCTACAAAATTGGAACCTCAGGGTCTTGCCCTAACATTACCAATGGAAACGGATTTTTCGC

AACAATGGCTTGGGCCGTCCCAAAAAACGACAAAAACAAAACAGCAACAAATCCATTAACAATAGAAGTACCATACA

TTTGTACAGAAGGAGAAGACCAAATTACCGTTTGGGGGTTCCACTCTGACAACGAGGCCCAAATGGCAAAGCTCTAT

GGGGACTCAAAGCCCCAGAAGTTCACCTCATCTGCCAACGGAGTGACCACACATTACGTTTCACAGATTGGTGGCTT

CCCAAATCAAACAGAAGACGGAGGACTACCACAAAGTGGTAGAATTGTTGTTGATTACATGGTGCAAAAATCTGGGA

AAACAGGAACAATTACCTATCAAAGGGGTATTTTATTGCCTCAAAAGGTGTGGTGCGCAAGTGGCAGGAGCAAGGTA

ATAAAAGGATCCTTGCCTTTAATTGGAGAAGCAGATTGCCTCCACGAAAAATACGGTGGATTAAACAAAAGCAAGCC

TTACTACACAGGGGAACATGCAAAGGCCATAGGAAATTGCCCAATATGGGTGAAAACACCCTTGAAGCTGGCCAATG

-continued

GAACCAAATATAGACCTCCTGCAAAACTATTAAAGGAAAGGGGTTTCTTCGGAGCTATTGCTGGTTTCTTAGAAGGA

GGATGGGAAGGAATGATTGCAGGTTGGCACGGATACACATCCCATGGGGCACATGGAGTAGCGGTGGCAGCAGACCT

TAAGAGCACTCAAGAGGCCATAAACAAGATAACAAAAAATCTCAACTCTTTGAGTGAGCTGGAAGTAAAGAATCTTC

AAAGACTAAGCGGTGCCATGGATGAACTCCACAACGAAATACTAGAACTAGATGAGAAAGTGGATGATCTCAGAGCT

GATACAATAAGCTCACAAATAGAACTCGCAGTCCTGCTTTCCAATGAAGGAATAATAAACAGTGAAGATGAACATCT

CTTGGCGCTTGAAAGAAAGCTGAAGAAAATGCTGGGCCCCTCTGCTGTAGAGATAGGGAATGGATGCTTTGAAACCA

AACACAAGTGCAACCAGACCTGTCTCGACAGAATAGCTGCTGGTACCTTTGATGCAGGAGAATTTTCTCTCCCCACC

TTTGATTCACTGAATATTACTGCTGCATCTTTAAATGACGATGGATTGGATAATCATACTATACTGCTTTACTACTC

AACTGCTGCCTCCAGTTTGGCTGTAACACTGATGATAGCTATCTTTGTTGTTTATATGGTCTCCAGAGACAATGTTT

CTTGCTCCATCTGTCTATAAGGGAAGTTAAGCCCTGTATTTTCCTTTATTGTAGTGCTTGTTTACTTGTTGTCATTA

CAAAGAAACGTTATTGAAAAATGCTCTTGTTACTACT (NA, B/Brisbane/60/08)

SEQ ID NO: 18

AGCAGAAGCAGAGCATCTTCTCAAAACTGAAGCAAATAGGCCAAAAATGAACAATGCTACCTTCAACTATACAAACG

TTAACCCTATTTCTCACATCAGGGGGAGTATTATTATCACTATATGTGTCAGCTTCATTATCATACTTACTATATTC

GGATATATTGCTAAAATTCTCACCAACAGAAATAACTGCACCAACAATGCCATTGGATTGTGCAAACGCATCAAATG

TTCAGGCTGTGAACCGTTCTGCAACAAAAGGGGTGACACTTCTTCTCCCAGAACCGGAGTGGACATACCCGCGTTTA

TCTTGCCCGGGCTCAACCTTTCAGAAAGCACTCCTAATTAGCCCTCATAGATTCGGAGAAACCAAAGGAAACTCAGC

TCCCTTGATAATAAGGGAACCTTTTATTGCTTGTGGACCAAATGAATGCAAACACTTTGCTCTAACCCATTATGCAG

CCCAACCAGGGGGATACTACAATGGAACAAGAGGAGACAGAAACAAGCTGAGGCATCTAATTTCAGTCAAATTGGGC

AAAATCCCAACAGTAGAAAACTCCATTTTCCACATGGCAGCATGGAGCGGGTCCGCGTGCCATGATGGTAAGGAATG

GACATATATCGGAGTTGATGGCCCTGACAATAATGCATTGCTCAAAGTAAAATATGGAGAAGCATATACTGACACAT

ACCATTCCTATGCAAACAAAATCCTAAGAACACAAGAAAGTGCCTGCAATTGCATCGGGGGAAATTGTTATCTTATG

ATAACTGATGGCTCAGCTTCAGGTGTTAGTGAATGCAGATTTCTTAAGATTCGAGAGGGCCGAATAATAAAAGAAAT

ATTTCCAACAGGAAGAGTAAAACACACTGAGGAATGCACATGCGGATTTGCCAGCAATAAAACCATAGAATGTGCCT

GTAGAGATAACAGTTACACAGCAAAAAGACCTTTTGTCAAATTAAACGTGGAGACTGATACAGCAGAAATAAGATTG

ATGTGCACAGATACTTATTTGGACACCCCCAGACCAAACGATGGAAGCATAACAGGCCCTTGTGAATCTAATGGGGA

CAAAGGGAGTGGAGGCATCAAGGGAGGATTTGTTCATCAAAGAATGGAATCCAAGATTGGAAGGTGGTACTCTCGAA

CGATGTCTAAAACTGAAAGGATGGGGATGGGACTGTATGTCAAGTATGATGGAGACCCATGGGCTGACAGTGATGCC

CTAGCTTTTAGTGGAGTAATGGTTTCAATGAAAGAACCTGGTTGGTACTCCTTTGGCTTCGAAATAAAAGATAAGAA

ATGCGATGTCCCCTGTATTGGGATAGAGATGGTACATGATGGTGGAAAAGAGACTTGGCACTCAGCAGCAACAGCCA

TTTACTGTTTAATGGGCTCAGGACAGCTGCTGTGGGACACTGTCACAGGTGTTGACATGGCTCTGTAATGGAGGAAT

GGTTGAGTCTGTTCTAAACCCTTTGTTCCTGTTTTGTTTGAACAATTGTCCTTACTAAACTTAATTGTTTCTGAAAA

ATGCTCTTGTTACTACT (NP, B/Lee/40)

SEQ ID NO: 19

MSNMDIDSINTGTIDKKPEELTPGTSGATRPIIKPATLAPPSNKRTRNPSPERTTTSSETDIGRKIQKKQTPTEIKK

SVYNMVVKLGEFYNQMMVKAGLNDDMERNLIQNAQAVERILLAATDDKKTEYQKKRNARDVKEGKEEIDHNKTGGTF

YKMVRDDKTIYFSPIKITFLKEEVKTMYKTTMGSDGFSGLNHIMIGHSQMNDVCFQRSKALKRVGLDPSLISTFAGS

TLPRRSGTTGVAIKGGGTLVAEAIRFIGRAMADRGLLRDIKAKTAYEKILLNLKNKCSAPQQKALVDQVIGSRNPGI

ADIEDLTLLARSMIVVRPSVASKVVLPISIYAKIPQLGFNIEEYSMVGYEAMALYNMATPVSILRMGDDAKDKSQLF

FMSCFGAAYEDLRVLSALTGTEFKPRSALKCKGFHVPAKEQVEGMGAALMSIKLQFWAPMTRSGGNEVSGEGGSGQI

-continued

SCSPVFAVERPIALSKQAVRRMLSMNVEGRDADVKGNLLKMMNDSMAKKTSGNAFIGKKMFQISDKNKVNPIEIPIK

QTIPSFFFGRDTAEDYDDLDY (PA, B/Panama/45/90)

SEQ ID NO: 20

MDTFITRNFQTTIIQKAKNTMAEFSEDPELQPAMLFNICVHLEVCYVISDMNFLDEEGKSYTALEGQGKEQNLRPQY

EVIEGMPRTIAWMVQRSLAQEHGIETPKYLADLFDYKTKRFIEVGITKGLADDYFWKKKEKLGNSMELMIFSYNQDY

SLSNESSLDEEGKGRVLSRLTELQAELSLKNLWQVLIGEEDVEKGIDFKLGQTISRLRDISVPAGFSNFEGMRSYID

NIDPKGAIERNLARMSPLVSATPKKLKWEDLRPIGPHIYNHELPEVPYNAFLLMSDELGLANMTEGKSKKPKTLAKE

CLEKYSTLRDQTDPILIMKSEKANENFLWKLWRDCVNTISNEEMSNELQKTNYAKWATGDGLTYQKIMKEVAIDDET

MCQEEPKIPNKCRVAAWVQTEMNLLSTLTSKRALDLPEIGPDVAPVEHVGSERRKYFVNEINCCKASTVMMKYVLFH

TSLLNESNASMGKYKVIPITNRVVNEKGESFDMLYGLAVKGQSHLRGDTDVVTVVTFEFSGTDPRVDSGKWPKYTVF

RIGSLFVSGREKSVYLYCRVNGTNKIQMKWGMEARRCLLQSMQQMEAIVEQESSIQGYDMTKACFKGDRVNSPKTFS

IGTQEGKLVKGSFGKALRVIFTKCLMHYVFGNAQLEGFSAESRRLLLLIQALKDRKGPWVFDLEGMYSGIEECISNN

PWVIQSAYWFNEWLGFEKEGSKVLESVDEIMNE (PB1, B/Panama/45/90)

SEQ ID NO: 21

MNINPYFLFIDVPIQAAISTTFPYTGVPPYSHGTGTGHTIDTVIRTHEYSNKGKQYVSDITGCTMVDPTNGPLPEDN

EPSAYAQLDCVLEALDRMDEEHPGLFQAASQNAMEALMVTTVDKLTQGRQTFDWTVCRNQPAATALNTTITSFRLND

LNGADKGGLVPFCQDIIDSLDKPEMTFFSVKNIKKKLPAKNRKGFLIKRIPMKVKDRITRVEYIKRALSLNTMTKDA

ERGKLKRRAIATAGIQIRGFVLVVENLAKNICENLEQSGLPVGGNEKKAKLSNAVAKMLSNCPPGGISMTVTGDNTK

WNECLNPRIFLAMTERITRDSPIWFRDFCSIAPVLFSNKIARLGKGFMITSKTKRLKAQIPCPDLFSIPLERYNEET

RAKLKKLKPFFNEEGTASLSPGMMMGMFNMLSTVLGVAALGIKNIGNKEYLWDGLQSSDDFALFVNAKDEETCMEGI

NDFYRTCKLLGINMSKKKSYCNETGMFEFTSMFYRDGFVSNFAMEIPSFGVAGVNESADMAIGMTIIKNNMINNGMG

PATAQTAIQLFIADYRYTYKCHRGDSKVEGKRMKIIKELWENTKGRDGLLVADGGPNIYNLRNLHIPEIVLKYNLMD

PEYKGRLLHPQNPFVGHLSIEGIKEADITPAHGPVKKMDYDAVSGTHSWRTKRNRSILNTDQRNMILEEQCYAKCCN

LFEACFNSASYRKPVGQHSMLEAMAHRLRVDARLDYESGRMSKDDFEKAMAHLGEIGYI (PB2, B/Panama/45/90)

SEQ ID NO: 22

MTLAKIELLKQLLRDNEAKTVLKQTTVDQYNIIRKFNTSRIEKNPSLRMKWAMCSNFPLALTKGDMANRIPLEYKGI

QLKTNAEDIGTKGQMCSIAAVTWWNTYGPIGDTEGFEKVYESFFLRKMRLDNATWGRITFGPVERVRKRVLLNPLTK

EMPPDEASNVIMEILFPKEAGIPRESTWIHRELIKEKREKLKGTMITPIVLAYMLERELVARRRFLPVAGATSAEFI

EMLHCLQGENWRQIYHPGGNKLTESRSQSMIVACRKIIRRSIVASNPLELAVEIANKTVIDTEPLKSCLTAIDGGDV

ACDIIRAALGLKIRQRQRFGRLELKRISGRGFKNDEEILIGNGTIQKIGIWDGEEEFHVRCGECRGILKKSKMRMEK

LLINSAKKEDMKDLIILCMVFSQDTRMFQGVRGEINFLNRAGQLLSPMYQLQRYFLNRSNDLFDQWGYEESPKASEL

HGINELMNASDYTLKGVVVTKNVIDDFSSTETEKVSITKNLSLIKRTGEVIMGANDVSELESQAQLMITYDTPKMWE

MGTTKELVQNTYQWVLKNLVTLKAQFLLGKEDMFQWDAFEAFESIIPQKMAGQYSGFARAVLKQMRDQEVMKTDQFI

KLLPFCFSPPKLRRNGEPYQFLRLVLKGGGENFIEVRKGSPLFSYNPQTEVLTICGRMMSLKGKIEDEERNRSMGNA

VLAGFLVSGKYDPDLGDFKTIEELEKLKPGEKANILLYQGKPVKVVKRKRYSALSNDISQGIKRQRMTVESMGWALS (NP, B/Panama/45/90)

SEQ ID NO: 23

MSNMDIDGINTGTIDKTPEEITSGTSGTTRPIIRPATLAPPSNKRTRNPSPERATTSSEADVGRKTQKKQTPTEIKK

SVYNMVVKLGEFYNQMMVKAGLNDDMERNLIQNAHAVERILLAATDDKKTEFQRKKNARDVKEGKEEIDHNKTGGTF

YKMVRDDKTIYFSPIRITFLKEEVKTMYKTTMGSDGFSGLNHIMIGHSQMNDVCFQRSKALKRVGLDPSLISTFAGS

TLPRRSGATGVAIKGGGTLVAEAIRFIGRAMADRGLLRDIKAKTAYEKILLNLKNKCSAPQQKALVDQVIGSRNPGI

-continued

ADIEDLTLLARSMVVVRPSVASKVVLPISIYAKIPQLGFNVEEYSMVGYEAMALYNMATPVSILRMGDDAKDKSQLF

FMSCFGAAYEDLRVLSALTGIEFKPRSALKCKGFHVPAKEQVEGMGAALMSIKLQFWAPMTRSGGNEVGGDGGSGQI

SCSPVFAVERPIALSKQAVRRMLSMNIEGRDADVKGNLLKMMNDSMAKKTNGNAFIGKKMFQISDKNKTNPVEIPIK

QTIPNEFFGRDTAEDYDDLDY ($M_1$, B/Panama/45/90)

SEQ ID NO: 24

MSLFGDTIAYLLSLTEDGEGKAELAEKLHCWFGGKEFDLDSALEWIKNKRCLTDIQKALIGASICFLKPKDQERKRR

FITEPLSGMGTTATKKKGLILAERKMRRCVSFHEAFEIAEGHESSALLYCLMVMYLNPGNYSMQVKLGTLCALCEKQ

ASHSHRAHSRAARSSVPGVRREMQMVSAMNTAKTMNGMGKGEDVQKLAEELQSNIGVLRSLGASQKNGEGIAKDVME

VLKQSSMGNSALVKKYL ($M_2$, B/Panama/45/90)

SEQ ID NO: 25

MLEPFQILSICSFILSALHFMAWTIGHLNQIKRGVNMKIRIKNPNKETINREVSILRHSYQKEIQAKETMKEVLSDN

MEVLSDHIVIEGLSAEEIIKMGETVLEVEELH ($NS_1$, B/Panama/45/90)

SEQ ID NO: 26

MADNMTTTQIEVGPGATNATINFEAGILECYERLSWQRALDYPGQDRLNKLKRKLESRIKTHNKSEPESKRMSLEER

KAIGVKMMKVLLFMNPSAGVEGFEPYCMKNPSNSNCPDCNWADYPPTPGKYLDGIEEEPENVGDSTEIVLRDMNNKD

ARQKIKEEVNTQKEGKFRLTIKRDIRNVLSLRVLVNGTFIKHPNGYKSLSTLHRLNAYDQSGRLVAKLVATDDLTVE

DEEDGHRILNSLFERLNEGHSKPIRAAETAVGVLSQFGQEHRLSPEERDN ($NS_2$, B/Panama/45/90)

SEQ ID NO: 27

MADNMTTTQIEWRMKKMAIGSSTHSSSVLMKDIQSQFEQLKLRWESYPNLVKSTDYHQKRETIRLVTEELYLLSKRI

DDNILFHKTVIANSSIIADMIVSLSLLETLYEMKDVVEVYSRQCL (HA, B/Panama/45/90)

SEQ ID NO: 28

MKAIIVLLMVVTSNADRICTGITSSNSPHVVKTATQGEVNVTGVIPLTTTPTKSHFANLKGTKTRGKLCPNCLNCTD

LDVALGRPMCVGTTPSAKASILHEVRPVTSGCFPIMHDRTKIRQLPNLLRGYENIRLSTQNVINAERAPGGPYRLGT

SGSCPNVTSRDGFFATMAWAVPRDNKTATNPLTVEVPYICTKGEDQITVWGFHSDDKTQMKNLYGDSNPQKFTSSAN

GVTTHYVSQIGGFPNQTEDGGLPQSGRIVVDYMVQKPGKTGTIVYQRGVLLPQKVWCASGRSKVIKGSLPLIGEADC

LHEKYGGLNKSKPYYTGEHAKAIGNCPIWVKTPLKLANGTKYRPPAKLLKERGFFGAIAGFLEGGWEGMIAGWHGYT

SHGAHGVAVAADLKSTQEAINKITKNLNSLSELEVKNLQRLSGAMDELHNEILELDEKVDDLRADTISSQIELAVLL

SNEGIINSEDEHLLALERKLKKMLGPSAVDIGNGCFETKHKCNQTCLDRIAAGTFNAGEFSLPTFDSLNITAASLND

DGLDNHTILLYYSTAASSLAVTLMIAIFIVYMVSRDNVSCSICL (NA, B/Panama/45/90)

SEQ ID NO: 29

MLPSTIQTLTLFLTSGGVLLSLYVSASLSYLLYSDILLKFSPTEITAPTMPLDCANASNVQAVNRSATKEMTLLLPE

PEWTYPRLSCPGSTFQKALLISPHRFGETRGNSAPLTIREPFIACGPKECKHFALTHYAAQPGGYYNGTREDRNKLR

HLISVKLGKIPTVENSIFHMAAWSGSACHDGREWTYIGVDGPDSNALIKIKYGEAYTDTYHSYANNILRTQESACNC

IGGDCYLMITDGSASGISKCRFLKIREGRIIKEIFPTGRVEHTEECTCGFASNKTIECACRDNSYTAKRPFVKLNVE

TDTAEIRLMCTETYLDTPRPDDGSITGPCESNGDKGRGGIKGGFVHQRMASKIGRWYSRTMSKTERMGMELYVKYDG

DPWTDSEALAPSGVMVSMEEPGWYSFGFEIKDKKCDVPCIGIEMVHDGGKKTWHSAATAIYCLMGSGQLLWDTVTGV

DMAL (PA, B/Panama/45/90)

SEQ ID NO: 30

AGCAGAAGCGGTGCGTTTGATTTGCCATAATGGATACTTTTATTACAAGAAACTTCCAGACTACAATAATACAAAAG

GCCAAAAACACAATGGCAGAATTTAGTGAAGATCCTGAATTACAACCAGCAATGCTATTCAACATCTGCGTCCATCT

AGAGGTTTGCTATGTAATAAGTGACATGAATTTTCTTGACGAAGAAGGAAAATCATATACAGCATTAGAAGGACAAG

-continued

GAAAAGAACAAAACTTGAGACCACAATATGAAGTAATTGAGGGAATGCCAAGAACCATAGCATGGATGGTCCAAAGA

TCCTTAGCTCAAGAGCATGGAATAGAGACTCCAAAGTATCTGGCTGATTTGTTTGATTATAAAACCAAGAGATTTAT

AGAAGTTGGAATAACAAAAGGATTGGCTGATGATTACTTTTGGAAAAAGAAAGAAAAGCTGGGAAATAGCATGGAAC

TGATGATATTCAGCTACAATCAAGACTATTCGTTAAGTAATGAATCCTCATTGGATGAGGAAGGGAAAGGGAGAGTG

CTAAGCAGACTCACAGAACTTCAGGCTGAATTAAGTCTGAAAAACCTATGGCAAGTTCTCATAGGAGAAGAAGATGT

TGAAAAGGGAATTGACTTTAAACTTGGACAAACAATATCTAGACTAAGGGATATATCTGTTCCAGCTGGTTTCTCCA

ATTTTGAAGGAATGAGGAGCTACATAGACAATATAGATCCTAAAGGAGCAATAGAAAGAAATCTAGCAAGGATGTCT

CCCTTAGTATCAGCCACACCTAAAAAGTTGAAATGGGAGGACCTAAGACCAATAGGGCCTCACATTTACAACCATGA

GTTACCAGAAGTTCCATATAATGCCTTTCTTCTAATGTCTGATGAATTGGGGCTGGCCAATATGACTGAGGGAAAGT

CCAAAAAACCGAAGACATTAGCCAAAGAATGTCTAGAAAAGTACTCAACACTACGGGATCAAACTGACCCAATATTA

ATAATGAAAAGCGAAAAAGCTAACGAAAATTTCCTATGGAAGCTGTGGAGGGACTGTGTAAATACAATAAGTAATGA

GGAAATGAGTAACGAGTTACAGAAAACCAATTATGCCAAGTGGGCCACAGGAGATGGATTAACATACCAGAAAATAA

TGAAAGAAGTAGCAATAGATGACGAAACAATGTGCCAAGAAGAGCCTAAAATCCCTAACAAATGTAGAGTGGCTGCT

TGGGTTCAAACAGAGATGAATTTATTGAGCACTCTGACAAGTAAAAGAGCTCTGGACCTACCAGAAATAGGGCCAGA

CGTAGCACCCGTGGAGCATGTAGGGAGTGAAAGAAGGAAATACTTTGTTAATGAAATCAACTGCTGTAAGGCCTCTA

CAGTTATGATGAAGTATGTGCTTTTTCACACTTCATTATTGAATGAAAGCAATGCCAGCATGGGAAAATATAAAGTA

ATACCAATAACCAATAGAGTAGTAAATGAAAAAGGAGAAAGTTTCGACATGCTTTATGGTCTGGCGGTTAAAGGACA

ATCTCATCTGAGGGGAGATACTGATGTTGTAACAGTTGTGACTTTCGAATTTAGTGGTACAGATCCCAGAGTGGACT

CAGGAAAGTGGCCAAAATATACTGTGTTTAGGATTGGCTCCCTATTTGTGAGTGGGAGGGAAAAATCTGTGTACCTA

TATTGCCGAGTGAATGGCACAAATAAGATCCAAATGAAATGGGGAATGGAAGCTAGAAGATGTCTGCTTCAATCAAT

GCAACAAATGGAAGCAATTGTTGAACAAGAATCATCGATACAAGGATATGACATGACCAAAGCTTGTTTCAAGGGAG

ACAGAGTAAATAGCCCCAAAACTTTTAGTATTGGGACTCAAGAAGGAAAACTAGTAAAAGGATCCTTTGGGAAAGCA

CTAAGAGTAATATTTACCAAATGTTTGATGCACTATGTATTTGGAAATGCCCAATTGGAGGGGTTTAGTGCCGAGTC

TAGGAGACTTCTACTGTTAATTCAAGCACTAAAGGACAGAAAGGGCCCTTGGGTGTTCGACTTAGAGGGAATGTATT

CTGGAATAGAAGAATGTATTAGTAACAACCCTTGGGTAATACAGAGTGCATACTGGTTCAATGAATGGTTGGGCTTT

GAAAAGGAGGGGAGTAAAGTATTAGAATCAGTAGATGAAATAATGAATGAATGAAAAAACATAGTACTCAATTTGGT

ACTATTTTGTTCATTATGTATCTAAACATCCAATAAAAAGAATCGAGAATCAAAAATGCACGTGTTTCTACT (PB1, B/Panama/45/90)

SEQ ID NO: 31

AGCAGAAGCGGAGCCTTTAAGATGAATATAAATCCTTATTTTCTCTTCATAGATGTACCCATACAGGCAGCAATTTC

AACAACATTCCCATACACCGGTGTTCCCCCTTACTCCCATGGAACGGGAACAGGCCACACAATAGACACCGTGATCA

GAACACATGAGTACTCGAACAAGGGAAAACAGTATGTTTCTGACATCACAGGATGTACAATGGTAGATCCAACAAAT

GGGCCATTACCCGAAGACAATGAGCCGAGTGCCTATGCACAATTAGATTGCGTTCTGGAGGCTTTGGATAGAATGGA

TGAAGAACATCCAGGTTTGTTTCAAGCAGCCTCACAGAATGCCATGGAGGCACTAATGGTCACAACTGTAGACAAAT

TAACCCAGGGGAGACAGACTTTTGATTGGACAGTATGCAGAAACCAGCCTGCTGCAACGGCACTAAACACAACAATA

ACCTCCTTTAGGTTGAATGATTTGAATGGAGCTGACAAGGGTGGATTGGTACCCTTTTGCCAAGATATCATTGATTC

ATTGGACAAACCTGAAATGACTTTCTTCTCAGTAAAGAATATAAAGAAAAAATTGCCTGCTAAAAACAGAAAGGGTT

TCCTCATAAAGAGAATACCAATGAAAGTAAAAGACAGGATAACCAGAGTGGAATACATCAAAAGAGCATTATCATTA

AACACAATGACAAAAGATGCTGAAAGGGGCAAACTAAAAAGAAGAGCGATTGCAACCGCTGGAATACAAATCAGAGG

GTTTGTATTAGTAGTTGAAAACTTGGCTAAAAATATCTGTGAAAATCTAGAACAAAGTGGTTTGCCCGTAGGTGGAA

ATGAAAAGAAGGCCAAACTGTCAAATGCAGTGGCCAAAATGCTCAGTAACTGCCCACCAGGAGGGATCAGCATGACA

-continued

GTAACAGGAGACAATACTAAATGGAATGAATGCTTAAATCCAAGAATCTTTTTGGCTATGACTGAAAGGATAACAAG

AGACAGCCCAATTTGGTTCCGGGATTTTTGTAGTATAGCACCGGTCTTGTTCTCCAATAAAATAGCCAGATTGGGAA

AAGGATTTATGATAACAAGCAAAACAAAAAGACTGAAGGCTCAAATACCTTGTCCAGATCTGTTTAGCATACCATTA

GAAAGATATAATGAAGAAACAAGGGCAAAATTAAAAAAGCTGAAACCATTCTTCAATGAAGAAGGAACGGCATCTTT

GTCGCCTGGGATGATGATGGGAATGTTTAATATGCTATCTACCGTGTTGGGAGTAGCCGCACTAGGTATCAAAAACA

TTGGAAACAAAGAATATTTATGGGATGGACTGCAATCTTCTGATGATTTTGCTCTGTTTGTTAATGCAAAAGATGAA

GAGACATGTATGGAAGGAATAAACGACTTTTACCGAACATGTAAATTATTGGGAATAAACATGAGCAAAAAGAAAAG

TTACTGTAATGAAACTGGAATGTTTGAATTTACAAGCATGTTCTATAGAGATGGATTTGTATCTAATTTTGCAATGG

AAATTCCTTCATTTGGAGTTGCTGGAGTAAATGAATCAGCAGATATGGCAATAGGAATGACAATAATAAAGAACAAT

ATGATCAACAATGGGATGGGTCCAGCAACAGCACAAACAGCCATACAATTATTCATAGCTGATTATAGGTACACCTA

CAAATGCCACAGGGGAGATTCCAAAGTGGAAGGAAAAAGAATGAAAATTATAAAGGAGCTATGGGAAAACACTAAAG

GAAGAGATGGTCTGTTAGTGGCAGATGGTGGGCCCAACATTTACAATTTGAGAAACTTACATATCCCAGAAATAGTA

TTGAAGTACAACCTAATGGACCCTGAATACAAAGGGCGGTTACTTCATCCTCAAAATCCATTTGTAGGACATTTATC

TATTGAGGGCATCAAAGAAGCAGATATAACCCCAGCACATGGTCCCGTAAAGAAAATGGATTATGATGCAGTATCTG

GAACTCATAGTTGGAGAACCAAAAGGAACAGATCTATACTAAATACTGACCAGAGGAACATGATTCTTGAGGAACAA

TGCTACGCTAAGTGTTGCAACCTTTTTGAGGCCTGTTTTAATAGTGCATCATACAGGAAACCAGTAGGTCAGCACAG

CATGCTTGAGGCTATGGCCCACAGATTAAGAGTGGATGCACGACTAGATTATGAATCAGGAAGAATGTCAAAGGATG

ATTTTGAGAAAGCAATGGCTCACCTTGGTGAGATTGGGTACATATAAGCTCCGAAGATGTCTATGGGGTTATTGGTC

ATCATTGAATACATGTGATAAACAAATGATTAAAATGAAAAAAGGCTCGTGTTTCTACT (PB2, B/Panama/45/90)

SEQ ID NO: 32

AGCAGAAGCGGAGCGTTTTCAAGATGACATTGGCTAAAATTGAATTGTTAAAACAACTGTTAAGGGACAATGAAGCC

AAAACAGTATTGAAACAAACAACGGTAGACCAATATAACATAATAAGAAAATTCAATACATCAAGAATTGAAAAGAA

CCCTTCATTGAGGATGAAGTGGGCAATGTGTTCTAATTTTCCCTTGGCTCTGACCAAGGGTGATATGGCAAACAGAA

TCCCCTTGGAATACAAGGGAATACAACTTAAAACAAATGCTGAAGACATAGGAACTAAAGGCCAAATGTGCTCAATA

GCAGCAGTTACCTGGTGGAATACATATGGACCAATAGGAGATACTGAAGGTTTCGAAAAGGTCTACGAAAGCTTTTT

TCTCAGAAAGATGAGACTTGACAATGCCACTTGGGGCCGAATAACTTTTGGCCCAGTTGAAAGAGTAAGAAAAAGGG

TACTGCTAAACCCTCTCACCAAGGAAATGCCTCCAGATGAAGCAAGTAATGTGATAATGGAAATATTGTTCCCTAAG

GAAGCAGGAATACCAAGAGAATCTACTTGGATACATAGGGAACTGATAAAAGAAAAAAGAGAAAAATTGAAAGGAAC

AATGATAACTCCCATTGTACTGGCATACATGCTTGAGAGAGAATTGGTTGCCAGAAGAAGGTTCCTGCCGGTGGCAG

GAGCAACATCAGCTGAGTTCATAGAAATGCTACACTGCTTACAAGGTGAAAATTGGAGACAAATATATCACCCAGGA

GGAAATAAACTAACTGAATCTAGGTCTCAATCGATGATTGTAGCTTGTAGAAAGATAATCAGAAGATCAATAGTCGC

ATCAAACCCATTAGAGCTAGCTGTAGAAATTGCAAACAAGACTGTGATAGATACTGAACCTTTAAAATCATGTCTGA

CAGCCATAGACGGAGGTGATGTAGCCTGTGACATAATAAGAGCTGCATTAGGACTAAAGATCAGACAAAGACAAAGA

TTTGGACGACTTGAACTAAAGAGAATATCAGGAAGAGGATTCAAAAATGATGAAGAAATATTAATCGGGAACGGAAC

AATACAGAAGATTGGAATATGGGACGGAGAAGAGGAGTTCCATGTAAGATGTGGTGAATGCAGGGGAATATTAAAAA

AGAGCAAAATGAGAATGGAAAAACTACTAATAAATTCAGCTAAAAAGGAAGACATGAAAGATTTAATAATCTTGTGC

ATGGTATTTTCTCAAGACACTAGGATGTTCCAAGGAGTGAGAGGAGAAATAAATTTTCTTAATAGAGCAGGCCAACT

TTTATCTCCAATGTACCAACTCCAAAGATATTTTTTGAATAGAAGCAACGATCTCTTTGATCAATGGGGGTATGAGG

AATCACCCAAAGCAAGTGAGCTACATGGAATAAATGAATTAATGAATGCATCTGACTACACTTTGAAAGGGGTTGTA

GTAACAAAAAATGTAATTGATGATTTTAGTTCTACTGAAACAGAAAAAGTATCTATAACAAAAAATCTTAGTTTAAT

AAAAAGGACTGGGGAAGTCATAATGGGGGCTAATGACGTAAGTGAATTAGAATCACAAGCTCAGCTAATGATAACAT

-continued

ATGATACACCTAAGATGTGGGAGATGGGAACAACCAAAGAACTGGTGCAAAACACCTACCAATGGGTGCTGAAAAAT

TTGGTAACACTGAAGGCTCAGTTTCTTCTAGGAAAAGAAGACATGTTCCAATGGGATGCATTTGAAGCATTTGAAAG

CATAATCCCCCAGAAGATGGCTGGCCAGTACAGTGGATTTGCAAGAGCAGTGCTCAAACAAATGAGAGACCAAGAGG

TTATGAAAACTGACCAGTTCATAAAGTTGTTGCCCTTTTGTTTCTCACCACCAAAATTAAGGAGAAATGGGGAGCCT

TATCAGTTCTTGAGGCTTGTATTGAAGGGAGGAGGAGAAAATTTCATCGAAGTAAGGAAAGGGTCCCCTCTATTCTC

TTACAATCCACAAACAGAAGTCCTAACTATATGCGGCAGAATGATGTCATTAAAAGGGAAAATTGAAGATGAAGAAA

GGAATAGATCAATGGGGAATGCAGTATTAGCGGGCTTTCTCGTTAGTGGCAAGTATGACCCAGATCTTGGAGATTTC

AAAACTATTGAAGAACTTGAAAAGCTGAAACCGGGGGAGAAAGCAAACATCTTACTTTATCAAGGAAAGCCCGTTAA

AGTAGTTAAAAGGAAAAGATATAGTGCTTTATCCAATGACATTTCACAAGGAATTAAGAGACAAAGAATGACAGTTG

AGTCCATGGGGTGGGCCTTGAGCTAATATAAATTTATCCATTAATTCAATAAACACAATTGAGTGAAAAATGCTCGT

GTTTCTACT (NP, B/Panama/45/90)

SEQ ID NO: 33

AGCAGAAGCACAGCATTTTCTTATTAACTTCAAGTACCAACAAAAGAACTGAAAATCAAAATGTCCAACATGGATAT

TGACGGTATCAACACTGGGACAATTGACAAAACACCGGAAGAAATAACTTCTGGAACCAGTGGGACAACCAGACCAA

TCATCAGACCAGCAACCCTTGCCCCACCAAGCAACAAACGAACCCGGAACCCATCCCCGGAAAGAGCAACCACAAGC

AGTGAAGCTGATGTCGGAAGGAAAACCCAAAAGAAACAGACCCCGACAGAGATAAAGAAGAGCGTCTACAATATGGT

AGTGAAACTGGGTGAATTCTATAACCAGATGATGGTCAAAGCTGGACTCAACGATGACATGGAGAGAAACCTAATCC

AAAATGCGCATGCTGTGGAAAGAATTCTATTGGCTGCCACTGATGACAAGAAAACTGAATTCCAGAGGAAAAAGAAT

GCCAGAGATGTCAAAGAAGGAAAAGAAGAAATAGACCACAACAAAACAGGAGGCACCTTTTACAAGATGGTAAGAGA

TGATAAAACCATCTACTTCAGCCCTATAAGAATTACCTTTTTAAAAGAAGAGGTGAAAACAATGTACAAAACCACCA

TGGGGAGTGATGGCTTCAGTGGACTAAATCACATAATGATTGGGCATTCACAGATGAATGATGTCTGTTTCCAAAGA

TCAAAGGCCCTAAAAAGAGTTGGACTTGACCCTTCATTAATCAGTACCTTTGCAGGAAGCACACTCCCCAGAAGATC

AGGTGCAACTGGTGTTGCAATCAAAGGAGGTGGAACTTTAGTGGCTGAAGCCATTCGATTTATAGGAAGAGCAATGG

CAGACAGAGGGCTATTGAGAGACATCAAAGCCAAGACTGCCTATGAAAAGATTCTTCTGAATCTAAAAAACAAATGC

TCTGCGCCCCAACAAAAGGCTCTAGTTGATCAAGTGATCGGAAGTAGAAATCCAGGGATTGCAGACATTGAAGACCT

AACCCTGCTTGCTCGTAGTATGGTCGTTGTTAGGCCCTCTGTGGCGAGCAAAGTAGTGCTTCCCATAAGCATTTATG

CTAAAATACCTCAACTAGGGTTCAATGTTGAAGAATACTCTATGGTTGGGTATGAAGCCATGGCTCTCTACAATATG

GCAACACCTGTTTCCATATTAAGAATGGGAGATGATGCAAAAGATAAATCGCAATTATTCTTCATGTCTTGCTTCGG

AGCTGCCTATGAAGACCTGAGAGTTTTGTCTGCATTAACAGGCATAGAATTCAAGCCTAGATCAGCATTAAAATGCA

AGGGTTTCCATGTTCCAGCAAAGGAACAGGTGGAAGGAATGGGGGCAGCTCTGATGTCCATCAAGCTCCAGTTTTGG

GCTCCAATGACCAGATCTGGAGGGAACGAAGTAGGTGGAGACGGAGGGTCTGGCCAAATAAGTTGCAGCCCAGTGTT

TGCAGTAGAAAGACCTATTGCTCTAAGCAAGCAAGCTGTAAGAAGAATGCTTTCAATGAATATTGAGGGACGTGATG

CAGATGTCAAAGGAAATCTACTCAAGATGATGAATGACTCAATGGCTAAGAAAACCAATGGAAATGCTTTCATTGGG

AAGAAAATGTTTCAAATATCAGACAAAAACAAAACCAATCCCGTTGAAATTCCAATTAAGCAGACCATCCCCAATTT

CTTCTTTGGGAGGGACACAGCAGAGGATTATGATGACCTCGATTATTAAAGCAACAAAATAGACACTATGACTGTGA

TTGTTTCAATACGTTTGGAATGTGGGTGTTTACTCTTATTGAAATAAATATAAAAAATGCTGTTGTTTCTACT (M, B/Panama/45/90)

SEQ ID NO: 34

AGCAGAAGCACGCACTTTCTTAAAATGTCGCTGTTTGGAGACACAATTGCCTACCTGCTTTCATTGACAGAAGATGG

AGAAGGCAAAGCAGAACTAGCAGAAAAATTACACTGTTGGTTCGGTGGGAAAGAATTTGACCTAGACTCTGCCTTGG

AATGGATAAAAAACAAAAGATGCTTAACTGATATACAGAAAGCACTAATTGGTGCCTCTATCTGCTTTTTAAAACCA

-continued

AAAGACCAAGAAAGAAAAAGAAGATTCATCACAGAGCCCCTATCAGGAATGGGAACAACAGCAACAAAAAAGAAGGG

CCTGATTCTAGCTGAGAGAAAAATGAGAAGATGTGTGAGTTTTCATGAAGCATTTGAAATAGCAGAAGGCCATGAAA

GCTCAGCGCTACTATATTGTCTCATGGTCATGTACCTGAACCCTGGAAATTATTCAATGCAAGTAAAACTAGGAACG

CTCTGTGCTTTGTGCGAGAAACAAGCATCACATTCACACAGGGCTCATAGCAGAGCAGCAAGATCTTCAGTGCCTGG

AGTGAGGCGAGAAATGCAGATGGTCTCAGCTATGAACACAGCAAAAACAATGAATGGAATGGGAAAGGGAGAAGACG

TCCAAAAACTGGCAGAAGAGCTGCAAAGCAACATTGGAGTATTGAGATCTCTTGGGGCAAGTCAAAAGAATGGGGAA

GGAATTGCAAAGGATGTGATGGAAGTGCTAAAGCAGAGCTCTATGGGAAATTCAGCTCTTGTGAAGAAATACCTATA

ATGCTCGAACCATTTCAGATTCTTTCAATTTGTTCTTTCATCTTATCAGCTCTCCATTTCATGGCTTGGACAATAGG

GCATTTGAATCAAATAAAAAGAGGAGTAAACATGAAAATACGAATAAAAAATCCAAATAAAGAGACAATAAACAGAG

AGGTATCAATTTTGAGACACAGTTACCAAAAAGAAATCCAGGCCAAAGAAACAATGAAGGAAGTACTCTCTGACAAC

ATGGAGGTATTGAGTGACCACATAGTAATTGAGGGGCTTTCTGCTGAAGAGATAATAAAAATGGGTGAAACAGTTTT

GGAGGTAGAAGAATTGCATTAAATTCAATTTTTACTGTATTTCTTGCTATGCATTTAAGCAAATTGTAATCAATGTC

AGCAAATAAACTGGAAAAAGTGCGTTGTTTCTACT (NS, B/Panama/45/90)

SEQ ID NO: 35

AGCAGAAGCAGAGGATTTGTTTAGTCACTGGCAAACGAAAAAATGGCGGACAACATGACCACAACACAAATTGAGGT

GGGTCCGGGAGCAACCAATGCCACCATAAACTTTGAAGCAGGAATTTTGGAGTGCTATGAAAGGCTTTCATGGCAAA

GAGCCCTTGACTACCCTGGTCAAGACCGCCTAAACAAACTAAAGAGAAAATTGGAATCAAGAATAAAGACTCACAAC

AAAAGTGAGCCAGAAAGTAAAAGGATGTCTCTTGAAGAGAGAAAAGCTATTGGGGTAAAAATGATGAAAGTGCTCCT

ATTTATGAACCCATCTGCTGGAGTTGAAGGGTTTGAGCCATATTGTATGAAAAATCCCTCCAATAGCAACTGTCCAG

ACTGCAATTGGGCTGATTACCCTCCAACACCAGGAAAGTACCTTGATGGCATAGAAGAAGAACCGGAGAATGTTGGT

GACTCAACTGAAATAGTATTAAGGGACATGAACAACAAAGATGCAAGGCAAAAGATAAAAGAGGAAGTAAACACTCA

GAAAGAAGGGAAATTCCGTTTGACAATAAAAAGGGATATACGTAATGTGTTGTCCTTGAGAGTGTTGGTAAACGGAA

CATTCATCAAGCACCCTAATGGATACAAGTCCTTATCAACTCTGCATAGATTGAATGCATATGACCAGAGTGGAAGA

CTTGTTGCTAAACTTGTTGCTACTGATGATCTTACAGTGGAGGATGAAGAAGATGGCCATCGGATCCTCAACTCACT

CTTCGAGCGTCTTAATGAAGGACATTCAAAGCCAATTCGAGCAGCTGAAACTGCGGTGGGAGTCTTATCCCAATTTG

GTCAAGAGCACCGATTATCACCAGAAGAGAGAGACAATTAGACTGGTTACGGAAGAACTTTATCTTTTAAGTAAAAG

AATTGATGATAACATATTGTTCCACAAAACAGTAATAGCCAACAGCTCCATAATAGCTGACATGATTGTATCATTAT

CATTATTGGAAACATTGTATGAAATGAAGGATGTGGTTGAAGTGTACAGCAGGCAGTGCTTGTGAATTTAAAATAAA

AATCCTCTTGTTACTACT (NA, B/Panama/45/90)

SEQ ID NO: 36

AGCAGAAGCAGAGCATCTTCTCAAAACTGAGGCAAATAGGCCAAAAATGAACAATGCTACCTTCAACTATACAAACG

TTAACCCTATTTCTCACATCAGGGGGAGTGTTATTATCACTATATGTGTCAGCTTCACTATCATACTTACTGTATTC

GGATATATTGCTAAAATTTTCACCAACAGAAATAACTGCACCAACAATGCCATTGGATTGTGCAAACGCATCAAATG

TTCAGGCTGTGAACCGTTCTGCAACAAAAGAGATGACACTTCTTCTCCCAGAACCGGAGTGGACATACCCTCGTTTA

TCTTGCCCGGGCTCAACCTTTCAGAAAGCACTCCTAATTAGCCCTCATAGATTCGGAGAAACCAGAGGAAACTCAGC

TCCCTTGACAATAAGGGAACCTTTTATTGCTTGTGGACCAAAGGAATGCAAACACTTTGCTCTAACCCATTATGCAG

CTCAACCAGGGGGATACTACAATGGAACAAGAGAGGACAGAAACAAGCTGAGGCATCTGATTTCAGTCAAATTGGGC

AAAATACCAACAGTAGAAAACTCCATTTTCCACATGGCAGCTTGGAGCGGGTCCGCATGCCATGATGGTAGAGAATG

GACATATATCGGAGTTGATGGCCCTGACAGTAATGCATTGATCAAAATAAAATATGGAGAAGCATATACTGACACAT

ACCATTCCTATGCAAACAACATCCTAAGAACACAAGAAAGTGCCTGCAATTGCATTGGGGGAGATTGTTATCTTATG

ATAACTGATGGCTCAGCTTCAGGAATTAGTAAATGCAGATTTCTTAAGATTCGAGAGGGTCGAATAATAAAAGAAAT

-continued

ATTTCCAACAGGAAGAGTAGAACATACTGAAGAATGCACATGCGGATTTGCCAGCAACAAAACCATAGAATGTGCCT

GTAGAGATAACAGTTACACAGCAAAAAGACCCTTTGTCAAATTAAATGTGGAGACTGATACAGCTGAAATAAGATTG

ATGTGCACAGAGACTTATTTGGACACCCCCAGACCAGATGATGGAAGCATAACAGGGCCTTGCGAATCTAATGGGGA

CAAAGGGCGTGGAGGCATCAAGGGAGGATTTGTTCATCAAAGAATGGCATCCAAGATTGGAAGATGGTACTCTCGAA

CGATGTCTAAAACTGAAGAATGGGGATGGAACTGTATGTCAAGTATGATGGAGACCCATGGACTGACAGTGAAGCC

CTTGCTCCTAGTGGAGTAATGGTTTCAATGGAAGAACCTGGTTGGTATTCTTTTGGCTTCGAAATAAAAGATAAGAA

ATGTGATGTCCCCTGTATTGGGATAGAGATGGTACACGATGGTGGAAAAAAGACTTGGCACTCAGCAGCAACAGCCA

TTTACTGTTTAATGGGCTCAGGACAATTGCTATGGGACACTGTCACAGGTGTTGATATGGCTCTGTAATGGAGGAAT

GGTTGAGTCTGTTCTAAACCCTTTGTTCCTATTTTGTTTGAATAATTGTCCTTACTGAACTTAATTGTTTCTGAAAA

ATGCTCTTGTTACTACT (HA, B/Panama/45/90)

SEQ ID NO: 37

AGCAGAAGCAGAGCATTTTCTAATATCCACAAAATGAAGGCAATAATTGTACTACTCATGGTAGTAACATCCAACGC

AGATCGAATCTGCACTGGGATAACATCTTCAAACTCACCTCATGTGGTCAAAACAGCTACTCAAGGGGAAGTCAATG

TGACTGGTGTGATACCACTGACAACAACACCAACAAAATCTCATTTTGCAAATCTAAAAGGAACAAAGACCAGAGGG

AAACTATGCCCAAACTGTCTCAACTGCACAGATCTGGATGTGGCCTTGGGCAGACCAATGTGTGTGGGGACCACACC

TTCGGCAAAAGCTTCAATACTCCACGAAGTCAGACCTGTTACATCCGGGTGCTTTCCTATAATGCACGACAGAACAA

AAATCAGACAGCTACCCAATCTTCTCAGAGGATATGAAAATATCAGATTATCAACCCAAAACGTTATCAACGCAGAA

AGAGCACCAGGAGGACCCTACAGACTTGGAACCTCAGGATCTTGCCCTAACGTTACCAGTAGAGACGGATTCTTCGC

AACAATGGCTTGGGCTGTCCCAAGGGACAACAAAACAGCAACGAATCCACTAACAGTAGAAGTACCATACATTTGTA

CAAAAGGAGAAGACCAAATTACTGTTTGGGGGTTCCATTCTGATGACAAAACCCAAATGAAAAACCTCTATGGAGAC

TCAAATCCTCAAAAGTTCACCTCATCTGCCAATGGAGTAACCACACATTATGTTTCTCAGATTGGTGGCTTCCCAAA

TCAAACAGAAGACGGAGGGCTACCACAAAGCGGCAGAATTGTTGTTGATTACATGGTGCAAAAACCTGGGAAAACAG

GAACAATTGTCTATCAAAGAGGTGTTTTGTTGCCTCAAAAGGTGTGGTGCGCAAGTGGCAGGAGCAAGGTAATAAAA

GGGTCCTTGCCTTTAATTGGTGAAGCAGATTGCCTTCACGAAAAATACGGTGGATTAAACAAAAGCAAGCCTTACTA

CACAGGAGAACATGCAAAAGCCATAGGAAATTGCCCAATATGGGTGAAAACACCTTTGAAGCTTGCCAATGGAACCA

AATATAGACCTCCTGCAAAACTATTAAAGGAAAGGGGTTTCTTCGGAGCTATTGCTGGTTTCTTAGAAGGAGGATGG

GAAGGAATGATTGCAGGTTGGCACGGATACACATCTCATGGAGCACATGGAGTGGCAGTGGCAGCAGACCTTAAGAG

TACGCAAGAAGCCATAAACAAGATAACAAAAAATCTCAATTCTTTGAGTGAGCTAGAAGTAAAGAATCTTCAAAGAC

TAAGTGGTGCCATGGATGAACTCCACAACGAAATACTCGAGCTGGATGAGAAAGTGGATGATCTCAGAGCTGACACA

ATAAGCTCGCAAATAGAGCTTGCAGTCTTGCTTTCCAACGAAGGAATAATAAACAGTGAAGATGAGCATCTATTGGC

ACTTGAGAGAAAACTAAAGAAAATGCTGGGTCCCTCTGCTGTAGACATAGGGAATGGATGCTTCGAAACCAAACACA

AGTGCAACCAGACCTGCTTAGACAGAATAGCTGCTGGCACCTTTAATGCAGGAGAATTTTCTCTTCCCACTTTTGAT

TCACTGAATATTACTGCTGCATCTTTAAATGATGATGGATTGGATAATCATACTATACTGCTCTACTACTCAACTGC

TGCTTCTAGTTTGGCTGTAACATTGATGATAGCTATTTTTATTGTTTATATGGTCTCCAGAGACAATGTTTCTTGCT

CCATCTGTCTATAAGGAAAATTAAGCCCTGTATTTTCCTTTGTTGTAGTGCTTGTTTGCTTGTTACCATTACAAAGA

AACGTTATTGAAAAATGCTCTTGTTACTACT (NP, B/Ann Arbor/1/66)

SEQ ID NO: 38

AGCAGAAGCACAGCATTTTCTTGTGAACTTCAAGTACCAACAAAAACTGAAAATCAAAATGTCCAACATGGATATTG

ACGGCATCAACACTGGAACAATTGACAAAACACCAGAAGAAATAACTTCCGGAACCAGTGGGGCAACCAGACCAATC

ATCAAGCCAGCAACCCTTGCCCCACCAAGCAATAAACGAACCCGAAACCCATCCCCAGAAAGGGCAACCACAAGCAG

-continued

CGAAGCGATTGTCGGAAGGAGAACCCAAAAGAAACAAACCCCGACAGAGATAAAGAAGAGCGTCTACAATATGGTAG

TGAAACTGGGTGAATTCTACAACCAGATGATGGTCAAAGCTGGACTCAACGATGACATGGAGAGAAACCTAATCCAA

AATGCACATGCTGTGGAAAGAATTCTATTGGCTGCTACTGATGACAAGAAAACTGAATACCAAAAGAAAAAGAATGC

CAGAGATGTCAAAGAAGGGAAAGAAGAAATAGACCACAACAAAACAGGAGGCACCTTTTATAAGATGGTAAGAGATG

ATAAAACCATCTACTTCAGCCCTATAAGAATTACCTTTTTAAAAGAAGAGGTGAAAACAATGTACAAGACCACCATG

GGGAGTGATGGTTTCAGTGGACTAAATCACATCATGATTGGGCATTCACAGATGAACGATGTCTGTTTCCAAAGATC

AAAGGCACTAAAAAGAGTTGGACTTGACCCTTCATTAATCAGTACTTTTGCAGGAAGCACACTCCCCAGAAGATCAG

GTGCAACTGGTGTTGCGATCAAAGGAGGTGGAACTTTAGTGGCAGAAGCCATTCGATTTATAGGAAGAGCAATGGCA

GACAGAGGGCTATTGAGAGACATCAGAGCCAAGACGGCCTATGAAAAGATTCTTCTGAATCTGAAAAACAAGTGCTC

TGCGCCCCAACAAAAGGCTCTAGTTGATCAAGTGATCGGAAGTAGAAACCCAGGGATTGCAGACATAGAAGACCTAA

CCCTGCTTGCCCGAAGCATGGTCGTTGTCAGGCCCTCTGTAGCGAGCAAAGTGGTGCTTCCCATAAGCATTAATGCT

AAAATACCTCAACTAGGGTTCAATGTTGAAGAATACTCTATGGTTGGGTATGAAGCCATGGCTCTTTATAATATGGC

AACACCTGTTTCCATATTAAGAATGGGAGACGATGCAAAAGATAAATCACAATTATTCTTCATGTCTTGCTTTGGAG

CTGCCTATGAAGACCAAAGAGTTTTGTCTGCACTAACCGGCACAGAATTCAAGCCTAGGTCAGCATTAAAGTGCAAG

GGTTTCCACGTTCCAGCAAAGGAGCAAGTGGAAGGAATGGGGGCAGCTCTGATGTCCATCAAGCTCCAGTTTTGGGC

CCCAATGACCAGATCTGGGGGGAACGAAGTAGGTGGAGACGGAGGGTCTGGTCAAATAAGTTGCAGCCCCGTGTTTG

CAGTAGAGAGACCTATTGCTCTAAGCAAGCAAGCTGTAAGAAGAATGCTGTCAATGAATATTGAGGGACGTGATGCA

GATGTCAAAGGAAATCTACTCAAGATGATGAATGATTCAATGGCTAAGAAAACCAATGGAAATGCTTTCATTGGGAA

GAAAATGTTTCAAATATCAGACAAAAACAAAATCAATCCCGTTGATATTCCAATTAAGCAGACCATCCCCAATTTCT

TCTTTGGGAGGGACACAGCAGAGGATTATGATGACCTCGATTATTAAAGCAACAAAATAGACACTATGGCTGTGACT

GTTTCAGTACGTTTGGAATGTGGGTGTTTACTCTTATTGAAATAAATGTAAAAAATGCTGTTGTTTCTACT (NP, B/Ann Arbor/1/66 - alternative sequence)

SEQ ID NO: 39

AGCAGAAGCACAGCATTTTCTTGTGAACTTCAAGTACCAACAAAAACTGAAAATCAAAATGTCCAACATGGATATTG

ACGGCATCAACACTGGAACAATTGACAAAACACCAGAAGAAATAACTTCCGGAACCAGTGGGGCAACCAGACCAATC

ATCAAGCCAGCAACCCTTGCCCCACCAAGCAATAAACGAACCCGAAACCCATCCCCAGAAAGGGCAACCACAAGCAG

CGAAGCGATTGTCGGAAGGAGAACCCAAAAGAAACAAACCCCGACAGAGATAAAGAAGAGCGTCTACAATATGGTAG

TGAAACTGGGTGAATTCTACAACCAGATGATGGTCAAAGCTGGACTCAACGATGACATGGAGAGAAACCTAATCCAA

AATGCACATGCTGTGGAAAGAATTCTATTGGCTGCTACTGATGACAAGAAAACTGAATACCAAAAGAAAAAGAATGC

CAGAGATGTCAAAGAAGGGAAAGAAGAAATAGACCACAACAAAACAGGAGGCACCTTTTATAAGATGGTAAGAGATG

ATAAAACCATCTACTTCAGCCCTATAAGAATTACCTTTTTAAAAGAAGAGGTGAAAACAATGTACAAGACCACCATG

GGGAGTGATGGTTTCAGTGGACTAAATCACATCATGATTGGGCATTCACAGATGAACGATGTCTGTTTCCAAAGATC

AAAGGCACTAAAAAGAGTTGGACTTGACCCTTCATTAATCAGTACTTTTGCAGGAAGCACACTCCCCAGAAGATCAG

GTGCAACTGGTGTTGCGATCAAAGGAGGTGGAACTTTAGTGGCAGAAGCCATTCGATTTATAGGAAGAGCAATGGCA

GACAGAGGGCTATTGAGAGACATCAGAGCCAAGACGGCCTATGAAAAGATTCTTCTGAATCTGAAAAACAAGTGCTC

TGCGCCCCAACAAAAGGCTCTAGTTGATCAAGTGATCGGAAGTAGAAACCCAGGGATTGCAGACATAGAAGACCTAA

CCCTGCTTGCCCGAAGCATGGTCGTTGTCAGGCCCTCTGTAGCGAGCAAAGTGGTGCTTCCCATAAGCATTAATGCT

AAAATACCTCAACTAGGGTTCAATGTTGAAGAATACTCTATGGTTGGGTATGAAGCCATGGCTCTTTATAATATGGC

AACACCTGTTTCCATATTAAGAATGGGAGACGATGCAAAAGATAAATCACAATTATTCTTCATGTCTTGCTTTGGAG

CTGCCTATGAAGACCAAAGAGTTTTGTCTGCACTAACCGGCACAGAATTCAAGCCTAGGTCAGCATTAAAGTGCAAG

GGTTTCCACGTTCCAGCAAAGGAGCAAGTGGAAGGAATGGGGGCAGCTCTGATGTCCATCAAGCTCCAGTTTTGGGC

CCCAATGACCAGATCTGGGGGGAACGAAGTAGGTGGAGACGGAGGGTCTGGTCAAATAAGTTGCAGCCCCGTGTTTG

-continued

CAGTAGAGAGACCTATTGCTCTAAGCAAGCAAGCTGTAAGAAGAATGCTGTCAATGAATATTGAGGGACGTGATGCA

GATGTCAAAGGAAATCTACTCAAGATGATGAATGATTCAATGGCTAAGAAAACCAATGGAAATGCTTTCATTGGGAA

GAAAATGTTTCAAATATCAGACAAAAACAAAATCAATCCCGTTGATATTCCAATTAAGCAGACCATCCCCAATTTCT

TCTTTGGGAGGGACACAGCAGAGGATTATGATGACCTCGATTATTAAAGCAACAAAATAGACACTATGGCTGTGACT

GTTTCAGTACGTTTGGAATGTGGGTGTTTACTCTTATTGAAATAAATGTAAAAAATGCTGTTGTTTCTACT (PB2, A/New Caledonia/20/1999)

SEQ ID NO: 40

ATGGAAAGAATAAAAGAGCTAAGGAATCTGATGTCACAATCTCGCACTCGCGAGATACTTACAAAAACTACTGTAGA

CCACATGGCCATAATCAAGAAATACACATCAGGAAGACAGGAGAAAAACCCATCACTTAGAATGAAATGGATGATGG

CAATGAAATACCCAATTACAGCAGATAAAAGGATAACGGAAATGATTCCTGAAAGAAATGAGCAAGGACAGACATTA

TGGAGTAAAGTGAATGATGCCGGATCAGACCGAGTGATGATATCACCCCTGGCTGTGACATGGTGGAACAGAAATGG

ACCAGTGGCAAGTACTATTCACTATCCAAAAATCTACAAAACTTACTTTGAAAAGGTTGAAAGGTTAAAACATGGAA

CCTTTGGCCCTGTACACTTTAGAAACCAAGTCAAAATACGCCGAAGAGTCGACATAAATCCTGGTCATGCAGACCTC

AGCGCCAAGGAGGCACAGGATGTAATTATGGAAGTTGTTTTCCCTAATGAAGTGGGAGCCAGAATACTAACATCAGA

ATCGCAATTAACGATAACCAAGGAGAAAAAAGAAGAACTCCAGAATTGCAAAATTTCCCCTTTGATGGTTGCATACA

TGTTAGAGAGGGAACTTGTCCGCAAAACGAGATTTCTCCCGGTTGCTGGTGGAACAAGCAGTGTGTACATTGAAGTT

TTGCATTTAACACAGGGGACATGCTGGGAGCAGATGTACACTCCAGGTGGGGAGGTGAGGAATGATGATGTTGATCA

AAGCCTAATTATTGCTGCTAGGAACATAGTGAGAAGAGCTGCAGTATCAGCAGATCCACTAGCATCTTTATTAGAAA

TGTGCCATAGCACACAGATTGGTGGGACAAGGATGGTGGATATTCTCAGGCAAAATCCAACAGAAGAACAAGCTGTG

GATATATGCAAAGCAGCAATGGGGCTGAGAATCAGTTCATCCTTCAGTTTTGGCGGATTCACATTTAAGAGAACAAG

TGGATCATCAGTCAAAAGGGAGGAAGAAGTGCTCACGGGCAATCTGCAAACATTGAAGCTAACTGTGCATGAGGGAT

ATGAAGAGTTCACAATGGTTGGGAAAAGGGCAACAGCTATACTCAGAAAAGCAACCAGGAGATTGATTCAACTAATA

GTGAGTGGAAGAGACGAACAGTCAATAGTCGAAGCAATAGTTGTAGCAATGGTATTCTCACAAGAAGATTGCATGGT

AAAAGCAGTTAGAGGTGATCTGAATTTCGTTAATAGAGCGAATCAGCGGTTGAATCCCATGCATCAACTTTTGAGAC

ATTTTCAGAAGGATGCTAAAGTACTTTTCTTAAATTGGGGAATTGAACCTATCGACAATGTGATGGGAATGATTGGG

ATATTACCTGATATGACTCCAAGTACCGAGATGTCAATGAGAGGAGTGAGAGTCAGCAAAATGGGTGTAGATGAATA

CTCCAATGCTGAAAGGGTAGTGGTGAGCATTGACCGTTTTTTGAGAGTCCGGGACCAAAGAGGAAATGTACTACTGT

CTCCAGAGGAAGTCAGTGAAACACAGGGAACAGAGAAACTGACAATAACTTACTCTTCATCAATGATGTGGGAGATT

AATGGCCCTGAGTCAGTGTTGATCAATACCTATCAGTGGATCATCAGAAACTGGGAGACTGTTAAAATTCAGTGGTC

TCAGAACCCTACAATGCTATACAATAAAATGGAATTCGAGCCATTTCAGTCTCTAGTCCCTAAGGCCATTAGAGGCC

AATACAGTGGGTTTGTTAGAACTCTATTTCAACAAATGAGGGATGTGCTTGGGACCTTTGACACAACTCAGATAATA

AAACTTCTTCCCTTTGCAGCCGCTCCACCAAAGCAAAGTAGAATGCAATTCTCATCATTGACTGTGAATGTGAGGGG

ATCAGGAATGAGAATACTTGTAAGGGGTAATTCTCCAGTATTCAACTACAACAAGACCACTAAGAGACTCACAGTCC

TCGGAAAGGATGCTGGCACTTTAACTGAAGACCCAGATGAAGGCACAGCTGGAGTGGAATCTGCTGTTCTAAGGGGA

TTCCTCATTCTAGGCAAAGAAGATAGAAGATATGGGCCAGCATTAAGCATCAATGAATTGAGCAACCTTGCGAAAGG

GGAAAAAGCTAATGTGCTAATTGGGCAAGGGGACGTAGTGTTGGTAATGAAACGAAAACGGGACTCTAGCATACTTA

CTGACAGCCAGACAGCGACCAAAAGAATTCGGATGGCCATCAAT (encodes the same amino acid sequence as SEQ ID NO: 40)

SEQ ID NO: 41

ATGGAACGCATTAAAGAACTGCGCAACCTGATGAGCCAGAGCCGCACCCGCGAAATTCTGACCAAAACCACCGTGGA

TCATATGGCGATTATTAAAAAATATACCAGCGGCCGCCAGGAAAAAAACCCGAGCCTGCGCATGAAATGGATGATGG

CGATGAAATATCCGATTACCGCGGATAAACGCATTACCGAAATGATTCCGGAACGCAACGAACAGGGCCAGACCCTG

-continued

TGGAGCAAAGTGAACGATGCGGGCAGCGATCGCGTGATGATTAGCCCGCTGGCGGTGACCTGGTGGAACCGCAACGG

CCCGGTGGCGAGCACCATTCATTATCCGAAAATTTATAAAACCTATTTTGAAAAAGTGGAACGCCTGAAACATGGCA

CCTTTGGCCCGGTGCATTTTCGCAACCAGGTGAAAATTCGCCGCCGCGTGGATATTAACCCGGGCCATGCGGATCTG

AGCGCGAAAGAAGCGCAGGATGTGATTATGGAAGTGGTGTTTCCGAACGAAGTGGGCGCGCGCATTCTGACCAGCGA

AAGCCAGCTGACCATTACCAAAGAAAAAAAAGAAGAACTGCAGAACTGCAAAATTAGCCCGCTGATGGTGGCGTATA

TGCTGGAACGCGAACTGGTGCGCAAAACCCGCTTTCTGCCGGTGGCGGGCGGCACCAGCAGCGTGTATATTGAAGTG

CTGCATCTGACCCAGGGCACCTGCTGGGAACAGATGTATACCCCGGGCGGCGAAGTGCGCAACGATGATGTGGATCA

GAGCCTGATTATTGCGGCGCGCAACATTGTGCGCCGCGCGGCGGTGAGCGCGGATCCGCTGGCGAGCCTGCTGGAAA

TGTGCCATAGCACCCAGATTGGCGGCACCCGCATGGTGGATATTCTGCGCCAGAACCCGACCGAAGAACAGGCGGTG

GATATTTGCAAAGCGGCGATGGGCCTGCGCATTAGCAGCAGCTTTAGCTTTGGCGGCTTTACCTTTAAACGCACCAG

CGGCAGCAGCGTGAAACGCGAAGAAGAAGTGCTGACCGGCAACCTGCAGACCCTGAAACTGACCGTGCATGAAGGCT

ATGAAGAATTTACCATGGTGGGCAAACGCGCGACCGCGATTCTGCGCAAAGCGACCCGCCGCCTGATTCAGCTGATT

GTGAGCGGCCGCGATGAACAGAGCATTGTGGAAGCGATTGTGGTGGCGATGGTGTTTAGCCAGGAAGATTGCATGGT

GAAAGCGGTGCGCGGCGATCTGAACTTTGTGAACCGCGCGAACCAGCGCCTGAACCCGATGCATCAGCTGCTGCGCC

ATTTTCAGAAAGATGCGAAAGTGCTGTTTCTGAACTGGGGCATTGAACCGATTGATAACGTGATGGGCATGATTGGC

ATTCTGCCGGATATGACCCCGAGCACCGAAATGAGCATGCGCGGCGTGCGCGTGAGCAAAATGGGCGTGGATGAATA

TAGCAACGCGGAACGCGTGGTGGTGAGCATTGATCGCTTTCTGCGCGTGCGCGATCAGCGCGGCAACGTGCTGCTGA

GCCCGGAAGAAGTGAGCGAAACCCAGGGCACCGAAAAACTGACCATTACCTATAGCAGCAGCATGATGTGGGAAATT

AACGGCCCGGAAAGCGTGCTGATTAACACCTATCAGTGGATTATTCGCAACTGGGAAACCGTGAAAATTCAGTGGAG

CCAGAACCCGACCATGCTGTATAACAAAATGGAATTTGAACCGTTTCAGAGCCTGGTGCCGAAAGCGATTCGCGGCC

AGTATAGCGGCTTTGTGCGCACCCTGTTTCAGCAGATGCGCGATGTGCTGGGCACCTTTGATACCACCCAGATTATT

AAACTGCTGCCGTTTGCGGCGGCGCCGCCGAAACAGAGCCGCATGCAGTTTAGCAGCCTGACCGTGAACGTGCGCGG

CAGCGGCATGCGCATTCTGGTGCGCGGCAACAGCCCGGTGTTTAACTATAACAAAACCACCAAACGCCTGACCGTGC

TGGGCAAAGATGCGGGCACCCTGACCGAAGATCCGGATGAAGGCACCGCGGGCGTGGAAAGCGCGGTGCTGCGCGGC

TTTCTGATTCTGGGCAAAGAAGATCGCCGCTATGGCCCGGCGCTGAGCATTAACGAACTGAGCAACCTGGCGAAAGG

CGAAAAAGCGAACGTGCTGATTGGCCAGGGCGATGTGGTGCTGGTGATGAAACGCAAACGCGATAGCAGCATTCTGA

CCGATAGCCAGACCGCGACCAAACGCATTCGCATGGCGATTAAC (HA, BX-35)

SEQ ID NO: 42

MKAIIVLLMVVTSNADRICTGITSSNSPHVVKTATQGEVNVTGVIPLTTTPTKSHFANLKGTETRGKLCPKCLNCTD

LDVALGRPKCTGKIPSARVSILHEVRPVTSGCFPIMHDRTKIRQLPNLLRGYEHIRLSTHNVINAENAPGGPYKIGT

SGSCPNITNGNGFFATMAWAVPKNDKNKTATNPLTIEVPYICTEGEDQITVWGFHSDDETQMAKLYGDSKPQKFTSS

ANGVTTHYVSQIGGFPNQTEDGGLPQSGRIVVDYMVQKSGKTGTITYQRGILLPQKVWCASGRSKVIKGSLPLIGEA

DCLHEKYGGLNKSKPYYTGEHAKAIGNCPIWVKTPLKLANGTKYRPPAKLLKERGFFGAIAGFLEGGWEGMIAGWHG

YTSHGAHGVAVAADLKSTQEAINKITKNLNSLSELEVKNLQRLSGAMDELHNEILELDEKVDDLRADTISSQIELAV

LLSNEGIINSEDEHLLALERKLKKMLGPSAVEIGNGCFETKHKCNQTCLDRIAAGTFDAGEFSLPTEDSLNITAASL

NDDGLDNHTILLYYSTAASSLAVTLMIAIFVVYMVSRDNVSCSICL (NP, B/Lee/40)

SEQ ID NO: 43

AGCATTTTCTTGTGAGCTTCGAGCACTAATAAAACTGAAAATCAAAATGTCCAACATGGATATTGACAGTATAAATA

CCGGAACAATCGATAAAAAACCAGAAGAACTGACTCCCGGAACCAGTGGGGCAACCAGACCAATCATCAAGCCAGCA

ACCCTTGCTCCGCCAAGCAACAAACGAACCCGAAATCCATCCCCAGAAAGGACAACCACAAGCAGTGAAACCGATAT

CGGAAGGAAAATCCAAAAGAAACAAACCCCAACAGAGATAAAGAAGAGCGTCTACAACATGGTGGTAAAGCTGGGTG

-continued

AATTCTACAACCAGATGATGGTCAAAGCTGGACTTAATGATGACATGGAAAGGAATCTAATCCAAAATGCACAAGCT

GTGGAGAGAATCCTATTGGCTGCAACTGATGACAAGAAAACTGAATACCAAAAGAAAAGGAATGCCAGAGATGTCAA

AGAAGGGAAGGAAGAAATAGACCACAACAAGACAGGAGGCACCTTTTATAAGATGGTAAGAGATGATAAAACCATCT

ACTTCAGCCCTATAAAAATTACCTTTTTAAAAGAAGAGGTGAAAACAATGTACAAGACCACCATGGGGAGTGATGGT

TTCAGTGGACTAAATCACATTATGATTGGACATTCACAGATGAACGATGTCTGTTTCCAAAGATCAAAGGCACTGAA

AAGGGTTGGACTTGACCCTTCATTAATCAGTACTTTTGCCGGAAGCACACTACCCAGAAGATCAGGTACAACTGGTG

TTGCAATCAAAGGAGGTGGAACTTTAGTGGCAGAAGCCATTCGATTTATAGGAAGAGCAATGGCAGACAGAGGGCTA

CTGAGAGACATCAAGGCCAAGACAGCCTATGAAAAGATTCTTCTGAATCTGAAAAACAAGTGCTCTGCGCCCCAACA

AAAGGCTCTAGTTGATCAAGTGATCGGAAGTAGGAACCCAGGGATTGCAGACATAGAAGACCTAACTCTGCTTGCCA

GAAGCATGATAGTTGTCAGACCCTCTGTAGCGAGCAAAGTGGTGCTTCCCATAAGCATTTATGCTAAAATACCTCAA

CTAGGATTCAATATCGAAGAATACTCTATGGTTGGGTATGAAGCCATGGCTCTTTATAATATGGCAACACCTGTTTC

CATATTAAGAATGGGAGATGACGCAAAAGATAAATCTCAACTATTCTTCATGTCGTGCTTCGGAGCTGCCTATGAAG

ATCTAAGAGTGTTATCTGCACTAACGGGCACCGAATTTAAGCCTAGATCAGCACTAAAATGCAAGGGTTTCCATGTC

CCGGCTAAGGAGCAAGTAGAAGGAATGGGGGCAGCTCTGATGTCCATCAAGCTTCAGTTCTGGGCCCCAATGACCAG

ATCTGGAGGGAATGAAGTAAGTGGAGAAGGAGGGTCTGGTCAAATAAGTTGCAGCCCTGTGTTTGCAGTAGAAAGAC

CTATTGCTCTAAGCAAGCAAGCTGTAAGAAGAATGCTGTCAATGAACGTTGAAGGACGTGATGCAGATGTCAAAGGA

AATCTACTCAAAATGATGAATGATTCGATGGCAAAGAAAACCAGTGGAAATGCTTTCATTGGGAAGAAAATGTTTCA

AATATCAGACAAAAACAAAGTCAATCCCATTGAGATTCCAATTAAGCAGACCATCCCCAGTTTCTTCTTTGGGAGGG

ACACAGCAGAGGATTATGATGACCTCGATTATTAAAGCAATAAAATAGACACTATGGCTGTGACTGTTTCAGTACGT

TTGGGATGTGGGTGTTTACTCTTATTGAAATAAATGTAAAA (NP, B/Ann Arbor/1/66)

SEQ ID NO: 44

MSNMDIDGINTGTIDKTPEEITSGTSGATRPIIKPATLAPPSNKRTRNPSPERATTSSEAIVGRRTQKKQTPTEIKK

SVYNMVVKLGEFYNQMMVKAGLNDDMERNLIQNAHAVERILLAATDDKKTEYQKKKNARDVKEGKEEIDHNKTGGTF

YKMVRDDKTIYFSPIRITFLKEEVKTMYKTTMGSDGFSGLNHIMIGHSQMNDVCFQRSKALKRVGLDPSLISTFAGS

TLPRRSGATGVAIKGGGTLVAEAIRFIGRAMADRGLLRDIRAKTAYEKILLNLKNKCSAPQQKALVDQVIGSRNPGI

ADIEDLTLLARSMVVVRPSVASKVVLPISINAKIPQLGENVEEYSMVGYEAMALYNMATPVSILRMGDDAKDKSQLF

FMSCFGAAYEDQRVLSALTGTEFKPRSALKCKGFHVPAKEQVEGMGAALMSIKLQFWAPMTRSGGNEVGGDGGSGQI

SCSPVFAVERPIALSKQAVRRMLSMNIEGRDADVKGNLLKMMNDSMAKKTNGNAFIGKKMFQISDKNKINPVDIPIK

QTIPNFFFGRDTAEDYDDLDY (NP, B/Ann Arbor/1/66)

SEQ ID NO: 45

MSNMDIDGINTGTIDKTPEEITSGTSGATRPIIKPATLAPPSNKRTRNPSPERAATSSEADVGRRTQKKQTPTEIKK

SVYNMVVKLGEFYNQMMVKAGLNDDMERNLIQNAHAAERILLAATDDKKTEFQKKKNARDVKEGKEEIDHNKTGGTF

YKMVRDDKTIYFSPIRITFLKEEVKTMYKTTMGSDGFSGLNHIMIGHSQMNDVCFQRSKALKRVGLDPSLISTFAGS

TLPRRSGATGVAIKGGGTLVAEAIRFIGRAMADRGLLRDIRAKTAYEKILLNLKNKCSAPQQKALVDQVIGSRNPGI

ADIEDLTLLARSMVVVRPSVASKVVLPISINAKIPQLGFNVEEYSMVGYEAMALYNMATPVSILRMGDDAKDKSQLF

EMSCFGAAYEDQRVLSALTGTEFKHRSALKCKGFHVPAKEQVEGMGAALMSIKLQFWAPMTRSGGNEVGGDGGSGQI

SCSPVFAVERPIALSKQAVRRMLSMNIEGRDADVKGNLLKMMNDSMTKKTNGNAFIGKKMFQISDKNKTNPIEIPIK

QTIPNFFFGRDTAEDYDDLDY

The invention claimed is:

1. A method of preparing a reassortant influenza B virus comprising steps of:

(i) introducing into a culture host one or more expression construct(s) which encode(s) the viral segments required to produce an influenza B virus wherein the expression construct(s) encode the HA segment from a first influenza B virus and the NP and/or PB2 segment from a second influenza B virus which is a B/Victoria/2/87-like strain; and (ii) culturing the culture host in order to produce a reassortant influenza B virus.

2. A method of preparing a reassortant influenza B virus comprising steps of:

(i) introducing into a culture host one or more expression construct(s) which encode(s) the viral segments required to produce an influenza B virus wherein the expression construct(s) encode the HA segment from a first influenza B virus and the NP segment from a second influenza B virus which is not B/Lee/40 or B/Ann Arbor/1/66 or B/Panama/45/90; and (ii) culturing the culture host in order to produce a reassortant influenza B virus.

3. The method of claim 2, wherein the NP and PB2 segments are from the second influenza B virus.

4. The method of claim 2, wherein the second influenza B virus is a B/Victoria/2/87-like strain.

5. The method of claim 1, wherein the PA, PB1, PB2, NP, NS and M segments are from the second influenza B virus.

6. The method of claim 1, wherein the reassortant influenza B virus comprises backbone segments from two or more influenza B strains.

7. The method of claim 6, wherein at least one backbone segment is from a B/Yamagata/16/88-like strain.

8. A method of preparing a reassortant influenza B virus comprising steps of (i) introducing into a culture host one or more expression construct(s) which encode(s) the viral segments required to produce an influenza B virus comprising the HA segment from a B/Yamagata/16/88-like strain and at least one backbone segment from a B/Victoria/2/87-like strain; and (ii) culturing the culture host in order to produce a reassortant influenza B virus.

9. The method of claim 8, wherein two, three, four, five or six backbone segments are from the B/Victoria/2/87-like strain.

10. The method of claim 8, wherein the ratio of segments from the B/Victoria/2/87-like strain and the B/Yamagata/16/88-like strain is 7:1, 6:2, 4:4, 3:5 or 1:7.

11. A method of preparing a reassortant influenza B virus comprising steps of (i) introducing into a culture host one or more expression construct(s) which encode(s) the viral segments required to produce an influenza B virus comprising viral segments from a B/Victoria/2/87-like strain and a B/Yamagata/16/88-like strain, wherein the ratio of segments from the B/Victoria/2/87-like strain and the B/Yamagata/16/88-like strain is 1:7, 2:6, 3:5, 4:4, 5:3, 6:2 or 7:1; and (ii) culturing the culture host in order to produce a reassortant influenza B virus.

12. The method of claim 10, wherein the ratio is 7:1, 6:2, 4:4, 3:5 or 1:7.

13. The method of claim 1, wherein the B/Victoria/2/87-like strain is B/Brisbane/60/08.

14. The method of claim 11, wherein the B/Yamagata/16/88-like strain is B/Panama/45/90.

15. The method of claim 1, wherein the NP segment encodes a protein which has at least 97%, at least 98%, at least 99% identity or 100% identity to the sequence of SEQ ID NO: 4.

16. The method of claim 1, wherein the PB2 segment encodes a protein which has at least 97%, at least 98%, at least 99% or 100% identity to the sequence of SEQ ID NO: 3.

17. The method of claim 1, wherein the NS segment encodes a protein which has at least 97%, at least 98%, at least 99% or 100% identity with the sequence of SEQ ID NO: 35 and/or wherein the M1 segment encodes a protein which has at least 97%, at least 98%, at least 99% or 100% identity with the sequence of SEQ ID NO: 34.

18. The method of claim 1, wherein the reassortant influenza B virus comprises:

a) a PA protein which has at least 97% identity, at least 98% identity, at least 99% identity or 100% identity to the sequence of SEQ ID NO: 1; and/or b) a PB1 protein which has at least 97% identity, at least 98% identity, at least 99% identity or 100% identity to the sequence of SEQ ID NO: 2; and/or c) a M1 protein which has at least 97% identity, at least 98%, at least 99% identity or 100% identity to the sequence of SEQ ID NO: 5; and/or d) a M2 protein which has at least 97% identity, at least 98% identity, at least 99% identity or 100% identity to the sequence of SEQ ID NO: 6; and/or e) a NS1 protein which has at least 97% identity, at least 98%, at least 99% identity or 100% identity to the sequence of SEQ ID NO: 7; and/or f) a NS2 protein which has at least 97% identity, at least 98%, at least 99% identity or 100% identity to the sequence of SEQ ID NO: 8.

19. A method of preparing a reassortant influenza B virus comprising steps of (i) introducing into a culture host one or more expression construct(s) which encode(s) the viral segments required to produce an influenza B virus comprising:

a) the PA segment of SEQ ID NO: 11, the PB1 segment of SEQ ID NO: 12, the PB2 segment of SEQ ID NO: 13, the NP segment of SEQ ID NO: 14, the NS segment of SEQ ID NO: 16 and the M segment of SEQ ID NO: 15; or b) the PA segment of SEQ ID NO: 11, the PB1 segment of SEQ ID NO: 31, the PB2 segment of SEQ ID NO:

13, the NP segment of SEQ ID NO: 14, the NS segment of SEQ ID NO: 35 and the M segment of SEQ ID NO: 34; or c) the PA segment of SEQ ID NO: 11, the PB1 segment of SEQ ID NO: 31, the PB2 segment of SEQ ID NO: 32, the NP segment of SEQ ID NO: 14, the NS segment of SEQ ID NO: 16 and the M segment of SEQ ID NO: 15; or d) the PA segment of SEQ ID NO: 30, the PB1 segment of SEQ ID NO: 12, the PB2 segment of SEQ ID NO: 13, the NP segment of SEQ ID NO: 14, the NS segment of SEQ ID NO: 16 and the M segment of SEQ ID NO: 15, or e) the PA segment of SEQ ID NO: 11, the PB1 segment of SEQ ID NO: 12, the PB2 segment of SEQ ID NO: 13, the NP segment of SEQ ID NO: 14, the NS segment of SEQ ID NO: 35 and the M segment of SEQ ID NO: 34;

f) the PA segment of SEQ ID NO: 30, the PB1 segment of SEQ ID NO: 31, the PB2 segment of SEQ ID NO: 13, the NP segment of SEQ ID NO: 33, the NS segment of SEQ ID NO: 35 and the M segment of SEQ ID NO: 34, or g) the PA segment of SEQ ID NO: 30, the PB1 segment of SEQ ID NO: 31, the PB2 segment of SEQ ID NO: 32, the NP segment of SEQ ID NO: 14, the NS segment of SEQ ID NO: 35 and the M segment of SEQ ID NO: 34, or h) the PA segment of SEQ ID NO: 11, the PB1 segment of SEQ ID NO: 12, the PB2 segment of SEQ ID NO: 13, the NP segment of SEQ ID NO: 33, the NS segment of SEQ ID NO: 35 and the M segment of SEQ ID NO: 34, or i) the PA segment of SEQ ID NO: 11, the PB1 segment of SEQ ID NO: 12, the PB2 segment of SEQ ID NO: 32, the NP segment of SEQ ID NO: 14, the NS segment of SEQ ID NO: 35 and the M segment of SEQ ID NO: 34, or j) the PA segment of SEQ ID NO: 30, the PB1 segment of SEQ ID NO: 12, the PB2 segment of SEQ ID NO: 13, the NP segment of SEQ ID NO: 14, the NS segment of SEQ ID NO: 35 and the M segment of SEQ ID NO: 34, or k) the PA segment of SEQ ID NO: 30, the PB1 segment of SEQ ID NO: 31, the PB2 segment of SEQ ID NO: 13, the NP segment of SEQ ID NO: 14, the NS segment of SEQ ID NO: 35 and the M segment of SEQ ID NO: 34; and (ii) culturing the culture host in order to produce a reassortant influenza B virus.

20. The method of claim 1, further comprising the step (iii) of purifying the reassortant virus obtained in step (ii).

21. A reassortant influenza B virus obtainable by the method of claim 1.

22. The method of claim 1, wherein the culture host is an embryonated hen egg.

23. The method of claim 1, wherein the culture host is a cell.

24. The method of claim 23, wherein the cell is an MDCK, Vero or PerC6 cell.

25. The method of claim 23, wherein the cell grows adherently.

26. The method of claim 23, wherein the cell grows in suspension.

27. The method of claim 26, wherein the MDCK cell is cell line MDCK 33016 (DSM ACC2219).

28. A method of preparing a vaccine, comprising the steps of (a) preparing a virus by the method of claim 1 and (b) preparing a vaccine from the virus.

29. A method of preparing a vaccine, comprising the step of preparing a vaccine from the virus of claim 21.

30. The method of claim 28, wherein step (b) involves inactivating the virus.

31. The method of claim 28, wherein the vaccine is a whole virion vaccine.

32. The method of claim 28, wherein the vaccine is a split virion vaccine.

33. The method of claim 28, wherein the vaccine is a surface antigen vaccine.

34. The method of claim 28, wherein the vaccine is a virosomal vaccine.

35. The method of claim 28, wherein the vaccine contains less than 10 ng of residual host cell DNA per dose.

36. The method of claim 28, wherein the vaccine comprises an antigen from an influenza A strain.

37. The method of claim 36, wherein the influenza A strain is of the H1, H2, H5, H7 or H9 subtype.

38. A vaccine obtainable by the method of claim 28.

39. An expression system comprising one or more expression construct(s) comprising the vRNA encoding segments of an influenza B virus of claim 21.

40. A host cell comprising the expression system of claim 39.

41. The host cell of claim 40, wherein the host cell is a mammalian cell.

42. The host cell of claim 41, wherein the host cell is an MDCK, Vero or PerC6 cell.

* * * * *

SEQUENCE LISTING

<160> NUMBER OF SEQ ID NOS: 45

<210> SEQ ID NO 1
<211> LENGTH: 726
<212> TYPE: PRT
<213> ORGANISM: Influenza B

<400> SEQUENCE: 1

Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
        35                  40                  45

Ser Asp Met Asn Phe Leu Asp Glu Glu Gly Lys Ala Tyr Thr Ala Leu
    50                  55                  60

Glu Gly Gln Gly Lys Glu Gln Asn Leu Arg Pro Gln Tyr Glu Val Ile
65                  70                  75                  80

Glu Gly Met Pro Arg Thr Ile Ala Trp Met Val Gln Arg Ser Leu Ala
                85                  90                  95

Gln Glu His Gly Ile Glu Thr Pro Lys Tyr Leu Ala Asp Leu Phe Asp
            100                 105                 110

Tyr Lys Thr Lys Arg Phe Ile Glu Val Gly Ile Thr Lys Gly Leu Ala
        115                 120                 125

Asp Asp Tyr Phe Trp Lys Lys Lys Glu Lys Leu Gly Asn Ser Met Glu
    130                 135                 140

Leu Met Ile Phe Ser Tyr Asn Gln Asp Tyr Ser Leu Ser Asn Glu Ser
145                 150                 155                 160

Ser Leu Asp Glu Glu Gly Lys Gly Arg Val Leu Ser Arg Leu Thr Glu
                165                 170                 175

Leu Gln Ala Glu Leu Ser Leu Lys Asn Leu Trp Gln Val Leu Ile Gly
            180                 185                 190

Glu Glu Asp Val Glu Lys Gly Ile Asp Phe Lys Leu Gly Gln Thr Ile
        195                 200                 205

Ser Arg Leu Arg Asp Ile Ser Val Pro Ala Gly Phe Ser Asn Phe Glu
    210                 215                 220

Gly Met Arg Ser Tyr Ile Asp Asn Ile Asp Pro Lys Gly Ala Ile Glu
225                 230                 235                 240

Arg Asn Leu Ala Arg Met Ser Pro Leu Val Ser Val Thr Pro Lys Lys
                245                 250                 255

Leu Thr Trp Glu Asp Leu Arg Pro Ile Gly Pro His Ile Tyr Asp His
            260                 265                 270

Glu Leu Pro Glu Val Pro Tyr Asn Ala Phe Leu Leu Met Ser Asp Glu
        275                 280                 285

Leu Gly Leu Ala Asn Met Thr Glu Gly Lys Ser Lys Lys Pro Lys Thr
    290                 295                 300

Leu Ala Lys Glu Cys Leu Glu Lys Tyr Ser Thr Leu Arg Asp Gln Thr
305                 310                 315                 320

Asp Pro Ile Leu Ile Met Lys Ser Glu Lys Ala Asn Glu Asn Phe Leu
                325                 330                 335

Trp Lys Leu Trp Arg Asp Cys Val Asn Thr Ile Ser Asn Glu Glu Thr
            340                 345                 350

Ser Asn Glu Leu Gln Lys Thr Asn Tyr Ala Lys Trp Ala Thr Gly Asp
        355                 360                 365

```
Gly Leu Thr Tyr Gln Lys Ile Met Lys Glu Val Ala Ile Asp Asp Glu
    370                 375                 380

Thr Met Cys Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Ile Ala Pro Val Glu
            420                 425                 430

His Val Gly Ser Glu Arg Arg Lys Tyr Phe Val Asn Glu Ile Asn Tyr
        435                 440                 445

Cys Lys Ala Ser Thr Val Met Met Lys Tyr Val Leu Phe His Thr Ser
    450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Met Leu
                485                 490                 495

Tyr Gly Leu Ala Val Lys Gly Gln Ser His Leu Arg Gly Asp Thr Asp
            500                 505                 510

Val Val Thr Val Val Thr Phe Glu Phe Ser Ser Thr Asp Pro Arg Val
        515                 520                 525

Asp Ser Gly Lys Trp Pro Lys Tyr Thr Val Phe Arg Ile Gly Ser Leu
    530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Glu Gln Glu Ser
            580                 585                 590

Ser Ile Gln Gly Tyr Asp Met Thr Lys Ala Cys Phe Lys Gly Asp Arg
        595                 600                 605

Val Asn Ser Pro Lys Thr Phe Ser Ile Gly Thr Gln Glu Gly Lys Leu
    610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Leu Ile Gln Ala Leu Lys Asp Arg Lys
            660                 665                 670

Gly Pro Trp Val Phe Asp Leu Glu Gly Met Tyr Ser Gly Ile Glu Glu
        675                 680                 685

Cys Ile Ser Asn Asn Pro Trp Val Ile Gln Ser Val Tyr Trp Phe Asn
    690                 695                 700

Glu Trp Leu Gly Phe Glu Lys Glu Gly Asn Lys Val Leu Glu Ser Val
705                 710                 715                 720

Asp Glu Ile Met Asp Glu
                725
```

<210> SEQ ID NO 2
<211> LENGTH: 752
<212> TYPE: PRT
<213> ORGANISM: Influenza B

<400> SEQUENCE: 2

```
Met Asn Ile Asn Pro Tyr Phe Leu Phe Ile Asp Val Pro Val Gln Ala
1               5                   10                  15
```

-continued

```
Ala Ile Ser Thr Thr Phe Pro Tyr Thr Gly Val Pro Pro Tyr Ser His
            20                  25                  30

Gly Thr Gly Thr Gly Tyr Thr Ile Asp Thr Val Ile Arg Thr His Glu
        35                  40                  45

Tyr Ser Asn Lys Gly Lys Gln Tyr Ile Ser Asp Val Thr Gly Cys Thr
    50                  55                  60

Met Val Asp Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
145                 150                 155                 160

Gly Gly Leu Ile Pro Phe Cys Gln Asp Ile Ile Asp Ser Leu Asp Arg
                165                 170                 175

Pro Glu Met Thr Phe Phe Ser Val Lys Asn Ile Lys Lys Lys Leu Pro
            180                 185                 190

Ala Lys Asn Arg Lys Gly Phe Leu Ile Lys Arg Ile Pro Met Lys Val
        195                 200                 205

Lys Asp Lys Ile Thr Lys Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
            260                 265                 270

Val Gly Gly Asn Glu Lys Lys Ala Lys Leu Ser Asn Ala Val Ala Lys
        275                 280                 285

Met Leu Ser Asn Cys Pro Pro Gly Gly Ile Ser Met Thr Val Thr Gly
    290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Val Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430
```

-continued

```
Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Val Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Leu Pro Ser Phe Gly
            500                 505                 510

Val Ala Gly Val Asn Glu Ser Ala Asp Met Ala Ile Gly Met Thr Ile
        515                 520                 525

Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
        595                 600                 605

Val Leu Lys Tyr Asn Leu Met Asp Pro Glu Tyr Lys Gly Arg Leu Leu
    610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Lys Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
        675                 680                 685

Ala Lys Cys Cys Asn Leu Phe Glu Ala Cys Phe Asn Ser Ala Ser Tyr
    690                 695                 700

Arg Lys Pro Val Gly Gln His Ser Met Leu Glu Ala Met Ala His Arg
705                 710                 715                 720

Leu Arg Met Asp Ala Arg Leu Asp Tyr Glu Ser Gly Arg Met Ser Lys
                725                 730                 735

Asp Asp Phe Glu Lys Ala Met Ala His Leu Gly Glu Ile Gly Tyr Ile
            740                 745                 750


<210> SEQ ID NO 3
<211> LENGTH: 770
<212> TYPE: PRT
<213> ORGANISM: Influenza B

<400> SEQUENCE: 3

Met Thr Leu Ala Lys Ile Glu Leu Leu Lys Gln Leu Leu Arg Asp Asn
1               5                   10                  15

Glu Ala Lys Thr Val Leu Lys Gln Thr Thr Val Asp Gln Tyr Asn Ile
            20                  25                  30

Ile Arg Lys Phe Asn Thr Ser Arg Ile Glu Lys Asn Pro Ser Leu Arg
        35                  40                  45

Met Lys Trp Ala Met Cys Ser Asn Phe Pro Leu Ala Leu Thr Lys Gly
    50                  55                  60
```

-continued

```
Asp Met Ala Asn Arg Ile Pro Leu Glu Tyr Lys Gly Ile Gln Leu Lys
65                  70                  75                  80

Thr Asn Ala Glu Asp Ile Gly Thr Lys Gly Gln Met Cys Ser Ile Ala
                85                  90                  95

Ala Val Thr Trp Trp Asn Thr Tyr Gly Pro Ile Gly Asp Thr Glu Gly
            100                 105                 110

Phe Glu Arg Val Tyr Glu Ser Phe Phe Leu Arg Lys Met Arg Leu Asp
        115                 120                 125

Asn Ala Thr Trp Gly Arg Ile Thr Phe Gly Pro Val Glu Arg Val Arg
    130                 135                 140

Lys Arg Val Leu Leu Asn Pro Leu Thr Lys Glu Met Pro Pro Asp Glu
145                 150                 155                 160

Ala Ser Asn Val Ile Met Glu Ile Leu Phe Pro Lys Glu Ala Gly Ile
                165                 170                 175

Pro Arg Glu Ser Thr Trp Ile His Arg Glu Leu Ile Lys Glu Lys Arg
            180                 185                 190

Glu Lys Leu Lys Gly Thr Met Ile Thr Pro Ile Val Leu Ala Tyr Met
        195                 200                 205

Leu Glu Arg Glu Leu Val Ala Arg Arg Arg Phe Leu Pro Val Ala Gly
    210                 215                 220

Ala Thr Ser Ala Glu Phe Ile Glu Met Leu His Cys Leu Gln Gly Glu
225                 230                 235                 240

Asn Trp Arg Gln Ile Tyr His Pro Gly Gly Asn Lys Leu Thr Glu Ser
                245                 250                 255

Arg Ser Gln Ser Met Ile Val Ala Cys Arg Lys Ile Ile Arg Arg Ser
            260                 265                 270

Ile Val Ala Ser Asn Pro Leu Glu Leu Ala Val Glu Ile Ala Asn Lys
        275                 280                 285

Thr Val Ile Asp Thr Glu Pro Leu Lys Ser Cys Leu Ala Ala Ile Asp
    290                 295                 300

Gly Gly Asp Val Ala Cys Asp Ile Ile Arg Ala Ala Leu Gly Leu Lys
305                 310                 315                 320

Ile Arg Gln Arg Gln Arg Phe Gly Arg Leu Glu Leu Lys Arg Ile Ser
                325                 330                 335

Gly Arg Gly Phe Lys Asn Asp Glu Glu Ile Leu Ile Gly Asn Gly Thr
            340                 345                 350

Ile Gln Lys Ile Gly Ile Trp Asp Gly Glu Glu Glu Phe His Val Arg
        355                 360                 365

Cys Gly Glu Cys Arg Gly Ile Leu Lys Lys Ser Lys Met Lys Leu Glu
    370                 375                 380

Lys Leu Leu Ile Asn Ser Ala Lys Lys Glu Asp Met Arg Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Gly Gln Leu Leu Ser Pro
            420                 425                 430

Met Tyr Gln Leu Gln Arg Tyr Phe Leu Asn Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Ser Met Asn Ala Ser Asp Tyr Thr Leu Lys Gly Ile Val
465                 470                 475                 480
```

Val Thr Arg Asn Val Ile Asp Asp Phe Ser Ser Ile Glu Thr Glu Lys
485 490 495

Val Ser Ile Thr Lys Asn Leu Ser Leu Ile Lys Arg Thr Gly Glu Val
500 505 510

Ile Met Gly Ala Asn Asp Val Ser Glu Leu Glu Ser Gln Ala Gln Leu
515 520 525

Met Ile Thr Tyr Asp Thr Pro Lys Met Trp Glu Met Gly Thr Thr Lys
530 535 540

Glu Leu Val Gln Asn Thr Tyr Gln Trp Val Leu Lys Asn Leu Val Thr
545 550 555 560

Leu Lys Ala Gln Phe Leu Leu Gly Lys Glu Asp Met Phe Gln Trp Asp
565 570 575

Ala Phe Glu Ala Phe Glu Ser Ile Ile Pro Gln Lys Met Ala Gly Gln
580 585 590

Tyr Ser Gly Phe Ala Arg Ala Val Leu Lys Gln Met Arg Asp Gln Glu
595 600 605

Val Met Lys Thr Asp Gln Phe Ile Lys Leu Leu Pro Phe Cys Phe Ser
610 615 620

Pro Pro Lys Leu Arg Ser Asn Gly Glu Pro Tyr Gln Phe Leu Lys Leu
625 630 635 640

Val Leu Lys Gly Gly Gly Glu Asn Phe Ile Glu Val Arg Lys Gly Ser
645 650 655

Pro Leu Phe Ser Tyr Asn Pro Gln Thr Glu Val Leu Thr Ile Cys Gly
660 665 670

Arg Met Met Ser Leu Lys Gly Lys Ile Glu Asp Glu Glu Arg Asn Arg
675 680 685

Ser Met Gly Asn Ala Val Leu Ala Gly Phe Leu Val Ser Gly Lys Tyr
690 695 700

Asp Pro Asp Leu Gly Asp Phe Lys Thr Ile Glu Glu Leu Glu Lys Leu
705 710 715 720

Lys Pro Gly Glu Lys Ala Asn Ile Leu Leu Tyr Gln Gly Lys Pro Val
725 730 735

Lys Val Val Lys Arg Lys Arg Tyr Ser Ala Leu Ser Asn Asp Ile Ser
740 745 750

Gln Gly Ile Lys Arg Gln Arg Met Thr Val Glu Ser Met Gly Trp Ala
755 760 765

Leu Ser
770

<210> SEQ ID NO 4
<211> LENGTH: 560
<212> TYPE: PRT
<213> ORGANISM: Influenza B

<400> SEQUENCE: 4

Met Ser Asn Met Asp Ile Asp Gly Ile Asn Thr Gly Thr Ile Asp Lys
1 5 10 15

Thr Pro Glu Glu Ile Thr Ser Gly Thr Ser Gly Thr Thr Arg Pro Ile
20 25 30

Ile Arg Pro Ala Thr Leu Ala Pro Pro Ser Asn Lys Arg Thr Arg Asn
35 40 45

Pro Ser Pro Glu Arg Ala Thr Thr Ser Ser Glu Asp Asp Val Gly Arg
50 55 60

Lys Thr Gln Lys Lys Gln Thr Pro Thr Glu Ile Lys Lys Ser Val Tyr
65 70 75 80

-continued

```
Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Val Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495
```

```
Lys Gly Asn Leu Leu Lys Met Met Asn Asp Ser Met Ala Lys Lys Thr
            500                 505                 510

Ser Gly Asn Ala Phe Ile Gly Lys Lys Met Phe Gln Ile Ser Asp Lys
        515                 520                 525

Asn Lys Thr Asn Pro Ile Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560


<210> SEQ ID NO 5
<211> LENGTH: 248
<212> TYPE: PRT
<213> ORGANISM: Influenza B

<400> SEQUENCE: 5

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 6
<211> LENGTH: 109
<212> TYPE: PRT
<213> ORGANISM: Influenza B

<400> SEQUENCE: 6

Met Leu Glu Pro Phe Gln Ile Leu Thr Ile Cys Ser Phe Ile Leu Ser
1               5                   10                  15
```

```
Ala Leu His Phe Met Ala Trp Thr Ile Gly His Leu Asn Gln Ile Lys
            20                  25                  30

Arg Gly Ile Asn Met Lys Ile Arg Ile Lys Gly Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Thr Met Lys Glu Val Leu Ser Asp Asn Met Glu Val
65                  70                  75                  80

Leu Asn Asp His Ile Ile Ile Glu Gly Leu Ser Ala Glu Glu Ile Ile
                85                  90                  95

Lys Met Gly Glu Thr Val Leu Glu Ile Glu Glu Leu His
            100                 105


<210> SEQ ID NO 7
<211> LENGTH: 282
<212> TYPE: PRT
<213> ORGANISM: Influenza B

<400> SEQUENCE: 7

Met Ala Asn Asn Asn Met Thr Thr Thr Gln Ile Glu Val Gly Pro Gly
1               5                   10                  15

Ala Thr Asn Ala Thr Ile Asn Phe Glu Ala Gly Ile Leu Glu Cys Tyr
            20                  25                  30

Glu Arg Leu Ser Trp Gln Arg Ala Leu Asp Tyr Pro Gly Gln Asp Arg
        35                  40                  45

Leu Asn Arg Leu Lys Arg Lys Leu Glu Ser Arg Ile Lys Thr His Asn
    50                  55                  60

Lys Ser Glu Pro Glu Ser Lys Arg Met Ser Leu Glu Glu Arg Lys Ala
65                  70                  75                  80

Ile Gly Val Lys Met Met Lys Val Leu Leu Phe Met Asn Pro Ser Ala
                85                  90                  95

Gly Ile Glu Gly Phe Glu Pro Tyr Cys Met Lys Ser Ser Ser Asn Ser
            100                 105                 110

Asn Cys Thr Lys Tyr Asn Trp Thr Asp Tyr Pro Ser Thr Pro Glu Arg
        115                 120                 125

Cys Leu Asp Asp Ile Glu Glu Glu Pro Glu Asp Val Asp Gly Pro Thr
    130                 135                 140

Glu Ile Val Leu Arg Asp Met Asn Asn Lys Asp Ala Arg Gln Lys Ile
145                 150                 155                 160

Lys Glu Glu Val Asn Thr Gln Lys Glu Gly Lys Phe Arg Leu Thr Ile
                165                 170                 175

Lys Arg Asp Met Arg Asn Val Leu Ser Leu Arg Val Leu Val Asn Gly
            180                 185                 190

Thr Phe Leu Lys His Pro Asn Gly His Lys Ser Leu Ser Thr Leu His
        195                 200                 205

Arg Leu Asn Ala Tyr Asp Gln Ser Gly Arg Leu Val Ala Lys Leu Val
    210                 215                 220

Ala Thr Asp Asp Leu Thr Val Glu Asp Glu Glu Asp Gly His Arg Ile
225                 230                 235                 240

Leu Asn Ser Leu Phe Glu Arg Leu Asn Glu Gly His Ser Lys Pro Ile
                245                 250                 255

Arg Ala Ala Glu Thr Ala Val Gly Val Leu Ser Gln Phe Gly Gln Glu
            260                 265                 270

His Arg Leu Ser Pro Glu Glu Gly Asp Asn
        275                 280
```

<210> SEQ ID NO 8
<211> LENGTH: 123
<212> TYPE: PRT
<213> ORGANISM: Influenza B

<400> SEQUENCE: 8

```
Met Ala Asn Asn Asn Met Thr Thr Thr Gln Ile Glu Trp Arg Met Lys
1               5                   10                  15

Lys Met Ala Ile Gly Ser Ser Thr His Ser Ser Ser Val Leu Met Lys
            20                  25                  30

Asp Ile Gln Ser Gln Phe Glu Gln Leu Lys Leu Arg Trp Glu Ser Tyr
        35                  40                  45

Pro Asn Leu Val Lys Ser Thr Asp Tyr His Gln Lys Arg Glu Thr Ile
    50                  55                  60

Arg Leu Val Thr Glu Glu Leu Tyr Leu Leu Ser Lys Arg Ile Asp Asp
65                  70                  75                  80

Asn Ile Leu Phe His Lys Thr Val Ile Ala Asn Ser Ser Ile Ile Ala
                85                  90                  95

Asp Met Val Val Ser Leu Ser Leu Leu Glu Thr Leu Tyr Glu Met Lys
            100                 105                 110

Asp Val Val Glu Val Tyr Ser Arg Gln Cys Leu
        115                 120
```

<210> SEQ ID NO 9
<211> LENGTH: 585
<212> TYPE: PRT
<213> ORGANISM: Influenza B

<400> SEQUENCE: 9

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205
```

-continued

```
His Ser Asp Asn Glu Ala Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585
```

<210> SEQ ID NO 10
<211> LENGTH: 466
<212> TYPE: PRT
<213> ORGANISM: Influenza B

<400> SEQUENCE: 10

```
Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Asn Glu Cys Lys
        115                 120                 125

His Phe Ala Leu Thr His Tyr Ala Ala Gln Pro Gly Gly Tyr Tyr Asn
    130                 135                 140

Gly Thr Arg Gly Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Asn Asn Ala Leu Leu Lys Val Lys Tyr Gly Glu
        195                 200                 205

Ala Tyr Thr Asp Thr Tyr His Ser Tyr Ala Asn Lys Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Val Ser Glu Cys Arg Phe Leu Lys Ile
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Asp
305                 310                 315                 320

Thr Tyr Leu Asp Thr Pro Arg Pro Asn Asp Gly Ser Ile Thr Gly Pro
                325                 330                 335

Cys Glu Ser Asn Gly Asp Lys Gly Ser Gly Gly Ile Lys Gly Gly Phe
            340                 345                 350

Val His Gln Arg Met Glu Ser Lys Ile Gly Arg Trp Tyr Ser Arg Thr
        355                 360                 365

Met Ser Lys Thr Glu Arg Met Gly Met Gly Leu Tyr Val Lys Tyr Asp
    370                 375                 380

Gly Asp Pro Trp Ala Asp Ser Asp Ala Leu Ala Phe Ser Gly Val Met
385                 390                 395                 400

Val Ser Met Lys Glu Pro Gly Trp Tyr Ser Phe Gly Phe Glu Ile Lys
                405                 410                 415
```

-continued

```
Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465


<210> SEQ ID NO 11
<211> LENGTH: 2305
<212> TYPE: DNA
<213> ORGANISM: Influenza B

<400> SEQUENCE: 11

agcagaagcg gtgcgtttga tttgtcataa tggatacttt tattacaaga aacttccaga     60

ctacaataat acaaaaggcc aaaaacacaa tggcagaatt tagtgaagat cctgaattgc    120

aaccagcaat gctattcaat atctgcgtcc atctagaggt ttgctatgta ataagtgaca    180

tgaattttct tgacgaagaa ggaaaagcat atacagcatt agaaggacaa gggaaagaac    240

aaaacttgag accacaatat gaagtaattg agggaatgcc aagaaccata gcatggatgg    300

tccagagatc cttagctcaa gagcatggaa tagagactcc caagtatctg gctgatttgt    360

ttgattataa aaccaaaaga tttatagaag ttggaataac aaagggattg gctgatgatt    420

acttttggaa aaagaaagaa aagttgggaa atagcatgga actgatgata ttcagctaca    480

atcaagacta ctcgttaagt aatgaatcct cattggatga ggaagggaaa gggagagtgc    540

taagcagact cacagaactt caggctgaat taagtctgaa aaatttatgg caagttctca    600

taggagaaga agatgttgaa aagggaattg attttaaact tggacaaaca atatctagac    660

taagggatat atctgttcca gctggtttct ccaatttga aggaatgagg agctacatag    720

acaatataga cccaaaagga gcaatagaga gaaatctagc aaggatgtct cccttagtat    780

cagtcacacc taaaaagtta acatgggagg acctaagacc aatagggcct cacatttacg    840

accatgagct accagaagtt ccatataatg cctttcttct aatgtctgat gaactgggat    900

tggccaatat gactgaggga aagtccaaaa aaccgaagac attagccaaa gaatgtctag    960

aaaagtactc aacactacgg gatcaaactg acccaatatt aataatgaaa agcgaaaaag   1020

ctaacgaaaa tttcctatgg aagctttgga gagactgtgt aaatacaata agtaatgagg   1080

aaacgagtaa cgagttacag aaaaccaatt atgccaaatg ggccacaggg gatggattaa   1140

cataccagaa aataatgaaa gaagtagcaa tagatgacga aacaatgtgc caagaagagc   1200

ctaaaatccc taacaaatgt agagtggctg cttgggttca aacagagatg aatctattga   1260

gcactctgac aagtaaaaga gctctggacc taccagaaat agggccagac atagcacccg   1320

tggagcatgt aggaagtgaa agaaggaaat actttgttaa tgaaatcaac tactgtaagg   1380

cctctacagt tatgatgaag tatgtgcttt ttcacacttc attgttgaat gaaagcaatg   1440

ccagcatggg aaaatacaaa gtaataccaa taaccaatag agtagtaaat gaaaaaggag   1500

aaagtttcga catgctttac ggtctggcgg ttaaaggaca atctcatctg aggggagata   1560

ctgatgttgt aacagttgta actttcgaat ttagtagtac agatccaaga gtggactcag   1620

gaaagtggcc aaaatatact gtgtttagga ttggctccct atttgtgagt gggagggaaa   1680

aatctgtgta cttgtattgc cgagtgaatg gcacaaataa gatccaaatg aaatggggaa   1740
```

```
tggaagctag aagatgtttg cttcaatcaa tgcaacaaat ggaggcaatt gttgaacagg   1800
aatcatcaat acaaggatat gacatgacca aagcctgttt caagggagac agagtaaata   1860
gccccaaaac tttcagtatt ggaactcaag aaggaaaact agtaaaagga tcctttggaa   1920
aagcactaag agtaatattt actaaatgct tgatgcacta tgtatttgga aatgcccaat   1980
tggaggggtt tagtgccgag tctaggagac ttctactgtt gattcaagca ttaaaggaca   2040
gaaagggccc ttgggtgttc gacttagagg gaatgtattc tggaatagaa gaatgtatta   2100
gcaacaaccc ttgggtaata cagagtgtat actggttcaa tgaatggttg ggctttgaaa   2160
aggaggggaa taaagtgttg gaatcagtgg atgaaataat ggatgaataa aaggaaatgg   2220
tactcaattt ggtactattt tgttcattat gtatctaaac atccaataaa aagaaccaag   2280
aatcaaaaat gcacgtgttt ctact                                         2305
```

<210> SEQ ID NO 12
<211> LENGTH: 2369
<212> TYPE: DNA
<213> ORGANISM: Influenza B

<400> SEQUENCE: 12

```
agcagaagcg gagcctttaa gatgaatata aatccttatt ttctcttcat agatgtgccc     60
gtacaggcag caatttcaac aacattccca tacactggtg ttcccccttta ttcccatgga   120
acaggaacag gctacacaat agacaccgtg atcagaacgc atgagtactc aaacaagggg   180
aaacagtaca tttctgatgt tacaggatgc acaatggtag atccaacaaa tggaccatta   240
cccgaagata atgagccgag tgcctatgcg caattagatt gcgttttaga ggctttggat   300
agaatggatg aagaacaccc aggtcttttt caagcagcct cacagaatgc tatggaggcc   360
ctaatggtca caactgtaga caaattaacc caggggagac agacttttga ttggacagta   420
tgcagaaacc aacctgctgc aacggcactg aacacaacaa taacctcttt taggttgaat   480
gatttaaatg gagccgacaa aggtggatta ataccttttt gccaggatat cattgattca   540
ttagaccgac ctgaaatgac tttcttctca gtaaagaata taaagaaaaa attgcctgcc   600
aaaaacagaa agggtttcct cataaagagg ataccaatga aggtaaaaga caaaataacc   660
aaagtggaat acatcaaaag agcattatca ttaaacacaa tgacaaaaga cgctgaaaga   720
ggcaaactga aaagaagagc gattgccact gctggaatac aaatcagagg gtttgtatta   780
gtagttgaaa acttggctaa aaatatatgt gaaaatctag aacaaagtgg tttaccagta   840
ggtggaaacg agaagaaagc caaactgtca aacgcagtgg ccaaaatgct cagtaactgc   900
ccaccaggag ggattagcat gacagtaaca ggagacaata caaaatggaa tgaatgttta   960
aacccaagaa tctttttggc tatgactgaa agaataacca gagacagccc agtttggttc  1020
agggattttt gtagtatagc accggtcctg ttctccaata agatagcaag attggggaaa  1080
gggtttatga taacaagcaa aacaaaaaga ctgaaggctc aaataccttg tcctgatctg  1140
tttagtatac cgttagaaag atataatgaa gaaacaaggg caaaattgaa aaagctaaaa  1200
ccattcttca atgaagaagg aactgcatct ttgtcgcctg ggatgatgat gggaatgttt  1260
aatatgctat ctaccgtgtt gggagtagct gcactaggta tcaagaacat tggaaacaaa  1320
gaatacttat gggatggact gcaatcttct gatgattttg ctctgtttgt taatgcaaag  1380
gatgaagaaa catgtatgga aggaataaac gacttttacc gaacatgtaa attattggga  1440
gtaaacatga gcaaaaagaa aagttactgt aatgagactg gaatgtttga atttacaagc  1500
atgttctaca gagatggatt tgtatctaat tttgcaatgg aactcccttc gtttggggtt  1560
```

-continued gctggagtaa atgaatcagc agatatggca ataggaatga caataataaa gaacaacatg 1620
atcaacaatg gaatgggtcc ggcaacagca caaacagcca tacagttatt catagctgat 1680
tatagataca cctacaaatg ccacagggga gattccaaag tagaaggaaa gagaatgaaa 1740
atcataaagg agttatggga aaacactaaa ggaagagatg gtctattagt agcagatggt 1800
gggcccaaca tttacaattt gagaaacctg catatcccag aaatagtatt aaagtataat 1860
ctaatggacc ctgaatacaa agggcggtta cttcatcctc aaaatccctt tgtgggacat 1920
ttgtctattg agggcatcaa agaggcagac ataaccccag cacatggtcc agtaaagaaa 1980
atggactacg atgcggtgtc tggaactcat agttggagaa ccaaaagaaa cagatctata 2040
ctaaacactg atcagaggaa catgattctt gaggaacaat gctacgctaa atgttgcaac 2100
ctatttgagg cctgttttaa cagtgcatca tacaggaagc cagtgggtca acatagcatg 2160
cttgaggcta tggcccacag attaagaatg gatgcacgat tagattatga atcagggaga 2220
atgtcaaagg atgattttga gaaagcaatg gctcaccttg gtgagattgg gtacatataa 2280
gcttcgaaga tgtttatggg gttattggtc atcattgaat acatgcgata cacaaatgat 2340
taaaatgaaa aaaggctcgt gtttctact 2369

<210> SEQ ID NO 13
<211> LENGTH: 2396
<212> TYPE: DNA
<213> ORGANISM: Influenza B

<400> SEQUENCE: 13
agcagaagcg gagcgttttc aagatgacat tggccaaaat tgaattgtta aaacaactgc 60
taagggacaa tgaagccaaa acagttttga agcaaacaac ggtagaccaa tataacataa 120
taagaaaatt caatacatca aggattgaaa agaatccttc actaaggatg aagtgggcca 180
tgtgttctaa ttttcccttg gctctaacca agggcgatat ggcaaacaga atccccttgg 240
aatacaaagg gatacaactt aaaacaaatg ctgaagacat aggaaccaaa ggccaaatgt 300
gctcaatagc agcagttact tggtggaata catatggacc aataggagat actgaaggtt 360
tcgaaagggt ctacgaaagc ttttttctca gaaaaatgag acttgacaac gccacttggg 420
gccgaataac ttttggccca gttgaaagag tgagaaaaag ggtactgcta aaccctctca 480
ccaaggaaat gcctccggat gaggcgagca atgtgataat ggaaatattg ttccctaaag 540
aagcaggaat accaagagaa tccacttgga tacataggga actgataaaa gaaaaaagag 600
aaaaattgaa aggaacaatg ataactccaa tcgtactggc atacatgctt gaaagagaac 660
tggttgctcg aagaagattc ttgccagtgg caggagcaac atcagctgag ttcatagaaa 720
tgctacactg cttacaaggt gaaaattgga gacaaatata tcacccagga gggaataaat 780
taactgagtc caggtctcaa tcaatgatag tagcttgtag aaaaataatc agaagatcaa 840
tagtcgcttc aaacccactg gagctagctg tagaaattgc aaacaagact gtgatagata 900
ctgaaccttt aaagtcatgt ctggcagcca tagacggagg tgatgtagct tgtgacataa 960
taagagctgc attaggacta aagatcagac aaagacaaag atttggacgg cttgagctaa 1020
aaagaatatc aggaagagga ttcaaaaatg atgaagaaat attaataggg aacggaacaa 1080
tacagaagat tggaatatgg gacggggaag aggagttcca tgtaagatgt ggtgaatgca 1140
ggggaatatt aaaaaagagt aaaatgaaac tggaaaaact actgataaat tcagccaaaa 1200
aggaggatat gagagattta ataatcttat gcatggtatt ttctcaagac actaggatgt 1260
tccaaggagt gagaggagaa ataaattttc ttaatcgagc aggccaactt ttatctccaa 1320
tgtaccaact ccaacgatat tttttgaata gaagcaacga cctttttgat caatgggggt 1380
atgaggaatc acccaaagca agtgaactac atgggataaa tgaatcaatg aatgcatctg 1440
actatacatt gaaagggatt gtagtgacaa gaaatgtaat tgacgacttt agctctattg 1500
aaacagaaaa agtatccata acaaaaaatc ttagtttaat aaaaaggact ggggaagtca 1560
taatgggagc taatgacgtg agtgaattag aatcacaagc acagctgatg ataacatatg 1620
atacacctaa aatgtgggaa atgggaacaa ccaaagaact ggtgcaaaac acttatcaat 1680
gggtgctaaa aaacttggtg acactgaagg ctcagtttct tctaggaaaa gaggacatgt 1740
tccaatggga tgcatttgaa gcatttgaga gcataattcc tcagaagatg gctggtcagt 1800
acagtggatt tgcaagagca gtgctcaaac aaatgagaga ccaggaggtt atgaaaactg 1860
accagttcat aaagttgttg ccttttttgtt tctcaccacc aaaattaagg agcaatgggg 1920
agccttatca attcttaaaa cttgtgttga aaggaggagg ggaaaatttc atcgaagtaa 1980
ggaaagggtc ccctctattt tcctataatc cacaaacaga agtcctaact atatgcggca 2040
gaatgatgtc attaaaaggg aaaattgaag atgaagaaag gaatagatca atgggtaatg 2100
cagtattagc aggctttctc gttagtggca agtatgaccc agatcttgga gatttcaaaa 2160
ctattgaaga acttgaaaag ctgaaaccgg gggaaaaggc aaacatctta ctttatcaag 2220
gaaaaccagt taaagtagtt aaaaggaaaa ggtatagtgc tttgtccaat gacatttcac 2280
aaggaattaa gagacaaaga atgacagttg agtctatggg gtgggccttg agctaatata 2340
aatttatcca ttaattcaat gaacgcaatt gagtgaaaaa tgctcgtgtt tctact 2396

<210> SEQ ID NO 14
<211> LENGTH: 1844
<212> TYPE: DNA
<213> ORGANISM: Influenza B

<400> SEQUENCE: 14
agcagaagca cagcattttc ttgtgaactt caagcaccag taaaagaact gaaaatcaaa 60
atgtccaaca tggatattga cggtataaac actgggacaa ttgacaaaac accggaagaa 120
ataacttctg gaaccagtgg gacaaccaga ccaatcatta gaccagcaac ccttgcccca 180
ccaagcaaca aacgaacccg taacccatcc ccggaaagag caaccacaag cagtgaagat 240
gatgtcggaa ggaaaaccca aaagaaacag accccgacag agataaagaa gagcgtctac 300
aacatggtgg tgaaactggg cgaattctat aaccagatga tggtcaaagc tggactcaat 360
gatgacatgg agagaaatct aatccaaaat gcgcatgccg tggaaagaat tctattggct 420
gccactgatg acaagaaaac cgagttccag aagaaaaaga atgccagaga tgtcaaagaa 480
gggaaagaag aaatagatca caacaaaaca ggaggcacct tttacaagat ggtaagagat 540
gataaaacca tctacttcag ccctataaga attacctttt taaaagaaga ggtgaaaaca 600
atgtacaaaa ccaccatggg gagtgatggc ttcagtggac taaatcacat aatgattggg 660
cattcacaga tgaatgatgt ctgtttccaa agatcaaagg cactaaaaag agttggactt 720
gatccttcat taatcagtac ctttgcggga agcacagtcc ccagaagatc aggtgcgact 780
ggtgttgcaa tcaaaggagg tggaacctta gtggctgaag ccattcgatt tataggaaga 840
gcaatggcag acagagggct attgagagac atcaaagcca agactgccta tgaaaagatt 900
cttctgaatc taaaaaacaa atgctctgcg ccccaacaaa aggctctagt tgatcaagtg 960
atcggaagca gaaatccggg gattgcagac attgaagatc taaccctgct tgctcgtagt 1020

```
atggtcgttg ttaggccctc tgtggcaagc aaagtggtgc ttcccataag catttacgcc   1080

aaaatacctc aactagggtt caatgttgaa gagtactcta tggttgggta cgaagccatg   1140

gctctttaca atatggcaac acctgtgtcc atattaagaa tgggagatga tgcaaaagat   1200

aaatcgcaat tattcttcat gtcttgcttc ggagctgcct atgaagacct gagagttttg   1260

tctgcattaa caggcacaga attcaagcct agatcagcat taaaatgcaa gggtttccat   1320

gttccagcaa aggaacaggt agaaggaatg ggagcagctc tgatgtccat caagctccag   1380

ttttgggctc cgatgaccag atctgggggg aacgaagtag gtggagacgg agggtctggc   1440

caaataagct gcagcccagt gtttgcagtg gaaagaccta ttgctctaag caagcaagct   1500

gtaagaagaa tgctgtcaat gaatattgag ggacgtgatg cagatgtcaa aggaaatcta   1560

ctcaagatga tgaatgactc aatggctaag aaaaccagtg gaaatgcttt cattgggaag   1620

aaaatgtttc aaatatcaga caaaaacaaa accaatccca ttgaaattcc aattaagcag   1680

accatcccca atttcttctt tgggagggac acagcagagg attatgatga cctcgattat   1740

taaggcaaca aaatagacac tatgactgtg attgtttcaa tacgtttgga atgtgggtgt   1800

ttattcttat taaaataaat ataaaaaatg ctgttgtttc tact                    1844
```

<210> SEQ ID NO 15
<211> LENGTH: 1189
<212> TYPE: DNA
<213> ORGANISM: Influenza B

<400> SEQUENCE: 15

```
agcagaagca cgcactttct taaaatgtcg ctgtttggag acacaattgc ctacctgctt     60

tcattgacag aagatggaga aggcaaagca gaactagcag aaaaattaca ctgttggttt    120

ggtgggaaag aatttgacct agactctgcc ttggaatgga taaaaaacaa aagatgctta    180

actgatatac aaaaagcact aattggtgcc tctatatgct ttttaaaacc caaagaccag    240

gaaagaaaaa gaagattcat cacagagccc ttatcaggaa tgggaacaac agcaacaaaa    300

aagaaaggcc tgattctggc tgagagaaaa atgagaagat gtgtgagctt tcatgaagca    360

tttgaaatag cagaaggcca tgaaagctca gcgctactat actgtctcat ggtcatgtac    420

ctgaatcctg gaaattattc aatgcaagta aaactaggaa cgctctgtgc tttatgcgag    480

aaacaagcat cacattcaca cagggctcat agcagagcag cgagatcttc agtgcctgga    540

gtgagacgag aaatgcagat ggtctcagct atgaacacag caaaaacaat gaatggaatg    600

ggaaaaggag aagacgtcca aaagctggca gaagagttgc aaagcaacat tggagtgctg    660

agatctcttg ggcaagccaa aaagaatggg gaagggattg caaaggatgt aatggaagtg    720

ctaaagcaga gctccatggg aaattcagct cttgtgaaga aatatctata atgctcgaac    780

catttcagat tcttacaatt tgttctttta tcttatcagc tctccatttc atggcttgga    840

caatagggca tttgaatcaa ataaaaagag gaataaacat gaaaatacga ataaaaggtc    900

caaacaaaga gacaataaac agagaggtat caattttgag acacagttac caaaaagaaa    960

tccaggccaa agaaacaatg aaggaagtac tctctgacaa catggaggta ttgaatgacc   1020

acataataat tgaggggctt tctgccgaag agataataaa aatgggtgaa acagttttgg   1080

agatagaaga attgcattaa attcaatttt actgtatttc ttactatgca tttaagcaaa   1140

ttgtaatcaa tgtcagcaaa taaactggaa aaagtgcgtt gtttctact               1189
```

<210> SEQ ID NO 16

<211> LENGTH: 1101
<212> TYPE: DNA
<213> ORGANISM: Influenza B

<400> SEQUENCE: 16
agcagaagca gaggatttgt ttagtcactg gcaaacaggg aaaaatggcg aacaacaaca 60
tgaccacaac acaaattgag gtgggtccgg gagcaaccaa tgccaccata aactttgaag 120
caggaattct agagtgctat gaaaggcttt catggcaaag agcccttgac taccctggtc 180
aagaccgcct aaacagacta aagagaaaat tagagtcaag aataaagact cacaacaaaa 240
gtgagcctga aagtaaaagg atgtcccttg aagagagaaa agcaattgga gtaaaaatga 300
tgaaagtact cctatttatg aatccgtctg ctggaattga agggtttgag ccatactgta 360
tgaaaagttc ctcaaatagc aactgtacga aatacaattg gactgattac ccttcaacac 420
cagagaggtg ccttgatgac atagaggaag aaccagagga tgttgatggc ccaactgaaa 480
tagtattaag ggacatgaac aacaaagatg caaggcaaaa gataaaggag gaagtaaaca 540
ctcagaaaga agggaagttc cgtttgacaa taaaaaggga tatgcgtaat gtattgtcct 600
tgagagtgtt ggtaaacgga acattcctca aacaccccaa tggacacaag tccttatcaa 660
ctctgcatag attgaatgca tatgaccaga gtggaaggct tgttgctaaa cttgttgcca 720
ctgatgatct tacagtggag gatgaagaag atggccatcg gatcctcaac tcactcttcg 780
agcgtcttaa tgaaggacat tcaaagccaa ttcgagcagc tgaaactgcg gtgggagtct 840
tatcccaatt tggtcaagag caccgattat caccagaaga gggagacaat tagactggtc 900
acggaagaac tttatctttt aagtaaaaga attgatgata acatactatt ccacaaaaca 960
gtaatagcta acagctccat aatagctgac atggttgtat cattatcatt attagaaaca 1020
ttgtatgaaa tgaaggatgt ggttgaagtg tacagcaggc agtgcttgtg aatttaaaat 1080
aaaaatcctc ttgttactac t 1101

<210> SEQ ID NO 17
<211> LENGTH: 1885
<212> TYPE: DNA
<213> ORGANISM: Influenza B

<400> SEQUENCE: 17
agcagaagca gagcattttc taatatccac aaaatgaagg caataattgt actactcatg 60
gtagtaacat ccaatgcaga tcgaatctgc actgggataa catcgtcaaa ctcaccacat 120
gtcgtcaaaa ctgctactca aggggaggtc aatgtgactg gtgtaatacc actgacaaca 180
acacccacca aatctcattt tgcaaatctc aaaggaacag aaaccagggg gaaactatgc 240
ccaaaatgcc tcaactgcac agatctggac gtagccttgg gcagaccaaa atgcacgggg 300 aaaatacccct cggcaagagt ttcaatactc catgaagtca gacctgttac atctgggtgc 360
tttcctataa tgcacgacag aacaaaaatt agacagctgc ctaaccttct ccgaggatac 420
gaacatatca ggttatcaac ccataacgtt atcaatgcag aaaatgcacc aggaggaccc 480
tacaaaattg gaacctcagg gtcttgccct aacattacca atggaaacgg atttttcgca 540
acaatggctt gggccgtccc aaaaaacgac aaaaacaaaa cagcaacaaa tccattaaca 600
atagaagtac catacatttg tacagaagga gaagaccaaa ttaccgtttg ggggttccac 660
tctgacaacg aggcccaaat ggcaaagctc tatggggact caaagcccca gaagttcacc 720
tcatctgcca acggagtgac cacacattac gtttcacaga ttggtggctt cccaaatcaa 780
acagaagacg gaggactacc acaaagtggt agaattgttg ttgattacat ggtgcaaaaa 840
tctgggaaaa caggaacaat tacctatcaa aggggtattt tattgcctca aaaggtgtgg 900
tgcgcaagtg gcaggagcaa ggtaataaaa ggatccttgc ctttaattgg agaagcagat 960
tgcctccacg aaaaatacgg tggattaaac aaaagcaagc cttactacac aggggaacat 1020
gcaaaggcca taggaaattg cccaatatgg gtgaaaacac ccttgaagct ggccaatgga 1080
accaaatata gacctcctgc aaaactatta aaggaaaggg gtttcttcgg agctattgct 1140
ggtttcttag aaggaggatg ggaaggaatg attgcaggtt ggcacggata cacatcccat 1200
ggggcacatg gagtagcggt ggcagcagac cttaagagca ctcaagaggc cataaacaag 1260
ataacaaaaa atctcaactc tttgagtgag ctggaagtaa agaatcttca aagactaagc 1320
ggtgccatgg atgaactcca caacgaaata ctagaactag atgagaaagt ggatgatctc 1380
agagctgata caataagctc acaaatagaa ctcgcagtcc tgctttccaa tgaaggaata 1440
ataaacagtg aagatgaaca tctcttggcg cttgaaagaa agctgaagaa aatgctgggc 1500
ccctctgctg tagagatagg gaatggatgc tttgaaacca aacacaagtg caaccagacc 1560
tgtctcgaca gaatagctgc tggtaccttt gatgcaggag aattttctct ccccaccttt 1620
gattcactga atattactgc tgcatcttta aatgacgatg gattggataa tcatactata 1680
ctgctttact actcaactgc tgcctccagt ttggctgtaa cactgatgat agctatcttt 1740
gttgtttata tggtctccag agacaatgtt tcttgctcca tctgtctata agggaagtta 1800
agccctgtat tttcctttat tgtagtgctt gtttacttgt tgtcattaca aagaaacgtt 1860
attgaaaaat gctcttgtta ctact 1885

<210> SEQ ID NO 18
<211> LENGTH: 1557
<212> TYPE: DNA
<213> ORGANISM: Influenza B

<400> SEQUENCE: 18
agcagaagca gagcatcttc tcaaaactga agcaaatagg ccaaaaatga acaatgctac 60
cttcaactat acaaacgtta accctatttc tcacatcagg gggagtatta ttatcactat 120
atgtgtcagc ttcattatca tacttactat attcggatat attgctaaaa ttctcaccaa 180
cagaaataac tgcaccaaca atgccattgg attgtgcaaa cgcatcaaat gttcaggctg 240
tgaaccgttc tgcaacaaaa ggggtgacac ttcttctccc agaaccggag tggacatacc 300
cgcgtttatc ttgcccgggc tcaacctttc agaaagcact cctaattagc cctcatagat 360
tcggagaaac caaaggaaac tcagctccct tgataataag ggaacctttt attgcttgtg 420
gaccaaatga atgcaaacac tttgctctaa cccattatgc agcccaacca gggggatact 480
acaatggaac aagaggagac agaaacaagc tgaggcatct aatttcagtc aaattgggca 540
aaatcccaac agtagaaaac tccattttcc acatggcagc atggagcggg tccgcgtgcc 600
atgatggtaa ggaatggaca tatatcggag ttgatggccc tgacaataat gcattgctca 660
aagtaaaata tggagaagca tatactgaca cataccattc ctatgcaaac aaaatcctaa 720
gaacacaaga aagtgcctgc aattgcatcg gggaaattg ttatcttatg ataactgatg 780
gctcagcttc aggtgttagt gaatgcagat ttcttaagat tcgagagggc cgaataataa 840
aagaaatatt tccaacagga agagtaaaac acactgagga atgcacatgc ggatttgcca 900
gcaataaaac catagaatgt gcctgtagag ataacagtta cacagcaaaa agaccttttg 960
tcaaattaaa cgtggagact gatacagcag aaataagatt gatgtgcaca gatacttatt 1020

-continued

```
tggacacccc cagaccaaac gatggaagca taacaggccc ttgtgaatct aatggggaca   1080

aagggagtgg aggcatcaag ggaggatttg ttcatcaaag aatggaatcc aagattggaa   1140

ggtggtactc tcgaacgatg tctaaaactg aaaggatggg gatgggactg tatgtcaagt   1200

atgatggaga cccatgggct gacagtgatg ccctagcttt tagtggagta atggtttcaa   1260

tgaaagaacc tggttggtac tcctttggct tcgaaataaa agataagaaa tgcgatgtcc   1320

cctgtattgg gatagagatg gtacatgatg gtggaaaaga gacttggcac tcagcagcaa   1380

cagccattta ctgtttaatg ggctcaggac agctgctgtg ggacactgtc acaggtgttg   1440

acatggctct gtaatggagg aatggttgag tctgttctaa accctttgtt cctgttttgt   1500

ttgaacaatt gtccttacta aacttaattg tttctgaaaa atgctcttgt tactact      1557
```

<210> SEQ ID NO 19
<211> LENGTH: 560
<212> TYPE: PRT
<213> ORGANISM: Influenza B

<400> SEQUENCE: 19

```
Met Ser Asn Met Asp Ile Asp Ser Ile Asn Thr Gly Thr Ile Asp Lys
1               5                   10                  15

Lys Pro Glu Glu Leu Thr Pro Gly Thr Ser Gly Ala Thr Arg Pro Ile
            20                  25                  30

Ile Lys Pro Ala Thr Leu Ala Pro Pro Ser Asn Lys Arg Thr Arg Asn
        35                  40                  45

Pro Ser Pro Glu Arg Thr Thr Thr Ser Ser Glu Thr Asp Ile Gly Arg
    50                  55                  60

Lys Ile Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala Gln
            100                 105                 110

Ala Val Glu Arg Ile Leu Leu Ala Ala Thr Asp Asp Lys Lys Thr Glu
        115                 120                 125

Tyr Gln Lys Lys Arg Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Lys Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Leu Pro Arg Arg Ser Gly Thr Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285
```

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Ile Val Val Arg Pro Ser Val Ala Ser Lys Val Val Leu Pro Ile
                325                 330                 335

Ser Ile Tyr Ala Lys Ile Pro Gln Leu Gly Phe Asn Ile Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Ser Gly Glu Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Val Glu Gly Arg Asp Ala Asp Val
                485                 490                 495

Lys Gly Asn Leu Leu Lys Met Met Asn Asp Ser Met Ala Lys Lys Thr
            500                 505                 510

Ser Gly Asn Ala Phe Ile Gly Lys Lys Met Phe Gln Ile Ser Asp Lys
        515                 520                 525

Asn Lys Val Asn Pro Ile Glu Ile Pro Ile Lys Gln Thr Ile Pro Ser
    530                 535                 540

Phe Phe Phe Gly Arg Asp Thr Ala Glu Asp Tyr Asp Asp Leu Asp Tyr
545                 550                 555                 560

<210> SEQ ID NO 20
<211> LENGTH: 726
<212> TYPE: PRT
<213> ORGANISM: Influenza B

<400> SEQUENCE: 20

Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
        35                  40                  45

Ser Asp Met Asn Phe Leu Asp Glu Glu Gly Lys Ser Tyr Thr Ala Leu
    50                  55                  60

Glu Gly Gln Gly Lys Glu Gln Asn Leu Arg Pro Gln Tyr Glu Val Ile
65                  70                  75                  80

Glu Gly Met Pro Arg Thr Ile Ala Trp Met Val Gln Arg Ser Leu Ala
                85                  90                  95

Gln Glu His Gly Ile Glu Thr Pro Lys Tyr Leu Ala Asp Leu Phe Asp

-continued

```
            100                 105                 110

Tyr Lys Thr Lys Arg Phe Ile Glu Val Gly Ile Thr Lys Gly Leu Ala
        115                 120                 125

Asp Asp Tyr Phe Trp Lys Lys Lys Glu Lys Leu Gly Asn Ser Met Glu
    130                 135                 140

Leu Met Ile Phe Ser Tyr Asn Gln Asp Tyr Ser Leu Ser Asn Glu Ser
145                 150                 155                 160

Ser Leu Asp Glu Glu Gly Lys Gly Arg Val Leu Ser Arg Leu Thr Glu
                165                 170                 175

Leu Gln Ala Glu Leu Ser Leu Lys Asn Leu Trp Gln Val Leu Ile Gly
            180                 185                 190

Glu Glu Asp Val Glu Lys Gly Ile Asp Phe Lys Leu Gly Gln Thr Ile
        195                 200                 205

Ser Arg Leu Arg Asp Ile Ser Val Pro Ala Gly Phe Ser Asn Phe Glu
    210                 215                 220

Gly Met Arg Ser Tyr Ile Asp Asn Ile Asp Pro Lys Gly Ala Ile Glu
225                 230                 235                 240

Arg Asn Leu Ala Arg Met Ser Pro Leu Val Ser Ala Thr Pro Lys Lys
                245                 250                 255

Leu Lys Trp Glu Asp Leu Arg Pro Ile Gly Pro His Ile Tyr Asn His
            260                 265                 270

Glu Leu Pro Glu Val Pro Tyr Asn Ala Phe Leu Leu Met Ser Asp Glu
        275                 280                 285

Leu Gly Leu Ala Asn Met Thr Glu Gly Lys Ser Lys Lys Pro Lys Thr
    290                 295                 300

Leu Ala Lys Glu Cys Leu Glu Lys Tyr Ser Thr Leu Arg Asp Gln Thr
305                 310                 315                 320

Asp Pro Ile Leu Ile Met Lys Ser Glu Lys Ala Asn Glu Asn Phe Leu
                325                 330                 335

Trp Lys Leu Trp Arg Asp Cys Val Asn Thr Ile Ser Asn Glu Glu Met
            340                 345                 350

Ser Asn Glu Leu Gln Lys Thr Asn Tyr Ala Lys Trp Ala Thr Gly Asp
        355                 360                 365

Gly Leu Thr Tyr Gln Lys Ile Met Lys Glu Val Ala Ile Asp Asp Glu
    370                 375                 380

Thr Met Cys Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Val Ala Pro Val Glu
            420                 425                 430

His Val Gly Ser Glu Arg Arg Lys Tyr Phe Val Asn Glu Ile Asn Cys
        435                 440                 445

Cys Lys Ala Ser Thr Val Met Met Lys Tyr Val Leu Phe His Thr Ser
    450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Met Leu
                485                 490                 495

Tyr Gly Leu Ala Val Lys Gly Gln Ser His Leu Arg Gly Asp Thr Asp
            500                 505                 510

Val Val Thr Val Val Thr Phe Glu Phe Ser Gly Thr Asp Pro Arg Val
        515                 520                 525
```

```
Asp Ser Gly Lys Trp Pro Lys Tyr Thr Val Phe Arg Ile Gly Ser Leu
    530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Glu Gln Glu Ser
            580                 585                 590

Ser Ile Gln Gly Tyr Asp Met Thr Lys Ala Cys Phe Lys Gly Asp Arg
        595                 600                 605

Val Asn Ser Pro Lys Thr Phe Ser Ile Gly Thr Gln Glu Gly Lys Leu
    610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Leu Ile Gln Ala Leu Lys Asp Arg Lys
            660                 665                 670

Gly Pro Trp Val Phe Asp Leu Glu Gly Met Tyr Ser Gly Ile Glu Glu
        675                 680                 685

Cys Ile Ser Asn Asn Pro Trp Val Ile Gln Ser Ala Tyr Trp Phe Asn
    690                 695                 700

Glu Trp Leu Gly Phe Glu Lys Glu Gly Ser Lys Val Leu Glu Ser Val
705                 710                 715                 720

Asp Glu Ile Met Asn Glu
                725


<210> SEQ ID NO 21
<211> LENGTH: 752
<212> TYPE: PRT
<213> ORGANISM: Influenza B

<400> SEQUENCE: 21

Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
            20                  25                  30

Gly Thr Gly Thr Gly His Thr Ile Asp Thr Val Ile Arg Thr His Glu
        35                  40                  45

Tyr Ser Asn Lys Gly Lys Gln Tyr Val Ser Asp Ile Thr Gly Cys Thr
    50                  55                  60

Met Val Asp Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
145                 150                 155                 160

Gly Gly Leu Val Pro Phe Cys Gln Asp Ile Ile Asp Ser Leu Asp Lys
```

```
                165                 170                 175

Pro Glu Met Thr Phe Phe Ser Val Lys Asn Ile Lys Lys Lys Leu Pro
            180                 185                 190

Ala Lys Asn Arg Lys Gly Phe Leu Ile Lys Arg Ile Pro Met Lys Val
        195                 200                 205

Lys Asp Arg Ile Thr Arg Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
            260                 265                 270

Val Gly Gly Asn Glu Lys Lys Ala Lys Leu Ser Asn Ala Val Ala Lys
        275                 280                 285

Met Leu Ser Asn Cys Pro Pro Gly Gly Ile Ser Met Thr Val Thr Gly
    290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Ile Pro Ser Phe Gly
            500                 505                 510

Val Ala Gly Val Asn Glu Ser Ala Asp Met Ala Ile Gly Met Thr Ile
        515                 520                 525

Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
            580                 585                 590
```

Gly Gly Pro Asn Ile Tyr Asn Leu Arg Asn Leu His Ile Pro Glu Ile
595 600 605

Val Leu Lys Tyr Asn Leu Met Asp Pro Glu Tyr Lys Gly Arg Leu Leu
610 615 620

His Pro Gln Asn Pro Phe Val Gly His Leu Ser Ile Glu Gly Ile Lys
625 630 635 640

Glu Ala Asp Ile Thr Pro Ala His Gly Pro Val Lys Lys Met Asp Tyr
645 650 655

Asp Ala Val Ser Gly Thr His Ser Trp Arg Thr Lys Arg Asn Arg Ser
660 665 670

Ile Leu Asn Thr Asp Gln Arg Asn Met Ile Leu Glu Glu Gln Cys Tyr
675 680 685

Ala Lys Cys Cys Asn Leu Phe Glu Ala Cys Phe Asn Ser Ala Ser Tyr
690 695 700

Arg Lys Pro Val Gly Gln His Ser Met Leu Glu Ala Met Ala His Arg
705 710 715 720

Leu Arg Val Asp Ala Arg Leu Asp Tyr Glu Ser Gly Arg Met Ser Lys
725 730 735

Asp Asp Phe Glu Lys Ala Met Ala His Leu Gly Glu Ile Gly Tyr Ile
740 745 750

<210> SEQ ID NO 22
<211> LENGTH: 770
<212> TYPE: PRT
<213> ORGANISM: Influenza B

<400> SEQUENCE: 22

Met Thr Leu Ala Lys Ile Glu Leu Leu Lys Gln Leu Leu Arg Asp Asn
1 5 10 15

Glu Ala Lys Thr Val Leu Lys Gln Thr Thr Val Asp Gln Tyr Asn Ile
20 25 30

Ile Arg Lys Phe Asn Thr Ser Arg Ile Glu Lys Asn Pro Ser Leu Arg
35 40 45

Met Lys Trp Ala Met Cys Ser Asn Phe Pro Leu Ala Leu Thr Lys Gly
50 55 60

Asp Met Ala Asn Arg Ile Pro Leu Glu Tyr Lys Gly Ile Gln Leu Lys
65 70 75 80

Thr Asn Ala Glu Asp Ile Gly Thr Lys Gly Gln Met Cys Ser Ile Ala
85 90 95

Ala Val Thr Trp Trp Asn Thr Tyr Gly Pro Ile Gly Asp Thr Glu Gly
100 105 110

Phe Glu Lys Val Tyr Glu Ser Phe Phe Leu Arg Lys Met Arg Leu Asp
115 120 125

Asn Ala Thr Trp Gly Arg Ile Thr Phe Gly Pro Val Glu Arg Val Arg
130 135 140

Lys Arg Val Leu Leu Asn Pro Leu Thr Lys Glu Met Pro Pro Asp Glu
145 150 155 160

Ala Ser Asn Val Ile Met Glu Ile Leu Phe Pro Lys Glu Ala Gly Ile
165 170 175

Pro Arg Glu Ser Thr Trp Ile His Arg Glu Leu Ile Lys Glu Lys Arg
180 185 190

Glu Lys Leu Lys Gly Thr Met Ile Thr Pro Ile Val Leu Ala Tyr Met
195 200 205

Leu Glu Arg Glu Leu Val Ala Arg Arg Arg Phe Leu Pro Val Ala Gly

-continued

```
210                 215                 220

Ala Thr Ser Ala Glu Phe Ile Glu Met Leu His Cys Leu Gln Gly Glu
225                 230                 235                 240

Asn Trp Arg Gln Ile Tyr His Pro Gly Gly Asn Lys Leu Thr Glu Ser
                245                 250                 255

Arg Ser Gln Ser Met Ile Val Ala Cys Arg Lys Ile Ile Arg Arg Ser
            260                 265                 270

Ile Val Ala Ser Asn Pro Leu Glu Leu Ala Val Glu Ile Ala Asn Lys
        275                 280                 285

Thr Val Ile Asp Thr Glu Pro Leu Lys Ser Cys Leu Thr Ala Ile Asp
    290                 295                 300

Gly Gly Asp Val Ala Cys Asp Ile Ile Arg Ala Ala Leu Gly Leu Lys
305                 310                 315                 320

Ile Arg Gln Arg Gln Arg Phe Gly Arg Leu Glu Leu Lys Arg Ile Ser
                325                 330                 335

Gly Arg Gly Phe Lys Asn Asp Glu Glu Ile Leu Ile Gly Asn Gly Thr
            340                 345                 350

Ile Gln Lys Ile Gly Ile Trp Asp Gly Glu Glu Glu Phe His Val Arg
        355                 360                 365

Cys Gly Glu Cys Arg Gly Ile Leu Lys Lys Ser Lys Met Arg Met Glu
    370                 375                 380

Lys Leu Leu Ile Asn Ser Ala Lys Lys Glu Asp Met Lys Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Gly Gln Leu Leu Ser Pro
            420                 425                 430

Met Tyr Gln Leu Gln Arg Tyr Phe Leu Asn Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Leu Met Asn Ala Ser Asp Tyr Thr Leu Lys Gly Val Val
465                 470                 475                 480

Val Thr Lys Asn Val Ile Asp Asp Phe Ser Ser Thr Glu Thr Glu Lys
                485                 490                 495

Val Ser Ile Thr Lys Asn Leu Ser Leu Ile Lys Arg Thr Gly Glu Val
            500                 505                 510

Ile Met Gly Ala Asn Asp Val Ser Glu Leu Glu Ser Gln Ala Gln Leu
        515                 520                 525

Met Ile Thr Tyr Asp Thr Pro Lys Met Trp Glu Met Gly Thr Thr Lys
    530                 535                 540

Glu Leu Val Gln Asn Thr Tyr Gln Trp Val Leu Lys Asn Leu Val Thr
545                 550                 555                 560

Leu Lys Ala Gln Phe Leu Leu Gly Lys Glu Asp Met Phe Gln Trp Asp
                565                 570                 575

Ala Phe Glu Ala Phe Glu Ser Ile Ile Pro Gln Lys Met Ala Gly Gln
            580                 585                 590

Tyr Ser Gly Phe Ala Arg Ala Val Leu Lys Gln Met Arg Asp Gln Glu
        595                 600                 605

Val Met Lys Thr Asp Gln Phe Ile Lys Leu Leu Pro Phe Cys Phe Ser
    610                 615                 620

Pro Pro Lys Leu Arg Arg Asn Gly Glu Pro Tyr Gln Phe Leu Arg Leu
625                 630                 635                 640
```

```
Val Leu Lys Gly Gly Gly Glu Asn Phe Ile Glu Val Arg Lys Gly Ser
                645                 650                 655

Pro Leu Phe Ser Tyr Asn Pro Gln Thr Glu Val Leu Thr Ile Cys Gly
            660                 665                 670

Arg Met Met Ser Leu Lys Gly Lys Ile Glu Asp Glu Glu Arg Asn Arg
        675                 680                 685

Ser Met Gly Asn Ala Val Leu Ala Gly Phe Leu Val Ser Gly Lys Tyr
    690                 695                 700

Asp Pro Asp Leu Gly Asp Phe Lys Thr Ile Glu Glu Leu Glu Lys Leu
705                 710                 715                 720

Lys Pro Gly Glu Lys Ala Asn Ile Leu Leu Tyr Gln Gly Lys Pro Val
                725                 730                 735

Lys Val Val Lys Arg Lys Arg Tyr Ser Ala Leu Ser Asn Asp Ile Ser
            740                 745                 750

Gln Gly Ile Lys Arg Gln Arg Met Thr Val Glu Ser Met Gly Trp Ala
        755                 760                 765

Leu Ser
    770


<210> SEQ ID NO 23
<211> LENGTH: 560
<212> TYPE: PRT
<213> ORGANISM: Influenza B

<400> SEQUENCE: 23

Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Thr Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Ala Asp Val Gly Arg
    50                  55                  60

Lys Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Phe Gln Arg Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Leu Pro Arg Arg Ser Gly Ala Thr
```

-continued 225 230 235 240

Gly Val Ala Ile Lys Gly Gly Gly Thr Leu Val Ala Glu Ala Ile Arg
245 250 255

Phe Ile Gly Arg Ala Met Ala Asp Arg Gly Leu Leu Arg Asp Ile Lys
260 265 270

Ala Lys Thr Ala Tyr Glu Lys Ile Leu Leu Asn Leu Lys Asn Lys Cys
275 280 285

Ser Ala Pro Gln Gln Lys Ala Leu Val Asp Gln Val Ile Gly Ser Arg
290 295 300

Asn Pro Gly Ile Ala Asp Ile Glu Asp Leu Thr Leu Leu Ala Arg Ser
305 310 315 320

Met Val Val Val Arg Pro Ser Val Ala Ser Lys Val Val Leu Pro Ile
325 330 335

Ser Ile Tyr Ala Lys Ile Pro Gln Leu Gly Phe Asn Val Glu Glu Tyr
340 345 350

Ser Met Val Gly Tyr Glu Ala Met Ala Leu Tyr Asn Met Ala Thr Pro
355 360 365

Val Ser Ile Leu Arg Met Gly Asp Asp Ala Lys Asp Lys Ser Gln Leu
370 375 380

Phe Phe Met Ser Cys Phe Gly Ala Ala Tyr Glu Asp Leu Arg Val Leu
385 390 395 400

Ser Ala Leu Thr Gly Ile Glu Phe Lys Pro Arg Ser Ala Leu Lys Cys
405 410 415

Lys Gly Phe His Val Pro Ala Lys Glu Gln Val Glu Gly Met Gly Ala
420 425 430

Ala Leu Met Ser Ile Lys Leu Gln Phe Trp Ala Pro Met Thr Arg Ser
435 440 445

Gly Gly Asn Glu Val Gly Gly Asp Gly Gly Ser Gly Gln Ile Ser Cys
450 455 460

Ser Pro Val Phe Ala Val Glu Arg Pro Ile Ala Leu Ser Lys Gln Ala
465 470 475 480

Val Arg Arg Met Leu Ser Met Asn Ile Glu Gly Arg Asp Ala Asp Val
485 490 495

Lys Gly Asn Leu Leu Lys Met Met Asn Asp Ser Met Ala Lys Lys Thr
500 505 510

Asn Gly Asn Ala Phe Ile Gly Lys Lys Met Phe Gln Ile Ser Asp Lys
515 520 525

Asn Lys Thr Asn Pro Val Glu Ile Pro Ile Lys Gln Thr Ile Pro Asn
530 535 540

Phe Phe Phe Gly Arg Asp Thr Ala Glu Asp Tyr Asp Asp Leu Asp Tyr
545 550 555 560

<210> SEQ ID NO 24
<211> LENGTH: 248
<212> TYPE: PRT
<213> ORGANISM: Influenza B

<400> SEQUENCE: 24

Met Ser Leu Phe Gly Asp Thr Ile Ala Tyr Leu Leu Ser Leu Thr Glu
1 5 10 15

Asp Gly Glu Gly Lys Ala Glu Leu Ala Glu Lys Leu His Cys Trp Phe
20 25 30

Gly Gly Lys Glu Phe Asp Leu Asp Ser Ala Leu Glu Trp Ile Lys Asn
35 40 45

```
Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 25
<211> LENGTH: 109
<212> TYPE: PRT
<213> ORGANISM: Influenza B

<400> SEQUENCE: 25

Met Leu Glu Pro Phe Gln Ile Leu Ser Ile Cys Ser Phe Ile Leu Ser
1               5                   10                  15

Ala Leu His Phe Met Ala Trp Thr Ile Gly His Leu Asn Gln Ile Lys
            20                  25                  30

Arg Gly Val Asn Met Lys Ile Arg Ile Lys Asn Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Thr Met Lys Glu Val Leu Ser Asp Asn Met Glu Val
65                  70                  75                  80

Leu Ser Asp His Ile Val Ile Glu Gly Leu Ser Ala Glu Glu Ile Ile
                85                  90                  95

Lys Met Gly Glu Thr Val Leu Glu Val Glu Glu Leu His
            100                 105


<210> SEQ ID NO 26
<211> LENGTH: 281
<212> TYPE: PRT
<213> ORGANISM: Influenza B

<400> SEQUENCE: 26

Met Ala Asp Asn Met Thr Thr Thr Gln Ile Glu Val Gly Pro Gly Ala
1               5                   10                  15
```

```
Thr Asn Ala Thr Ile Asn Phe Glu Ala Gly Ile Leu Glu Cys Tyr Glu
            20                  25                  30

Arg Leu Ser Trp Gln Arg Ala Leu Asp Tyr Pro Gly Gln Asp Arg Leu
        35                  40                  45

Asn Lys Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asn Pro Ser Ala Gly
                85                  90                  95

Val Glu Gly Phe Glu Pro Tyr Cys Met Lys Asn Pro Ser Asn Ser Asn
            100                 105                 110

Cys Pro Asp Cys Asn Trp Ala Asp Tyr Pro Pro Thr Pro Gly Lys Tyr
        115                 120                 125

Leu Asp Gly Ile Glu Glu Glu Pro Glu Asn Val Gly Asp Ser Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Ile Arg Asn Val Leu Ser Leu Arg Val Leu Val Asn Gly Thr
            180                 185                 190

Phe Ile Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Arg Asp Asn
        275                 280


<210> SEQ ID NO 27
<211> LENGTH: 122
<212> TYPE: PRT
<213> ORGANISM: Influenza B

<400> SEQUENCE: 27

Met Ala Asp Asn Met Thr Thr Thr Gln Ile Glu Trp Arg Met Lys Lys
1               5                   10                  15

Met Ala Ile Gly Ser Ser Thr His Ser Ser Ser Val Leu Met Lys Asp
            20                  25                  30

Ile Gln Ser Gln Phe Glu Gln Leu Lys Leu Arg Trp Glu Ser Tyr Pro
        35                  40                  45

Asn Leu Val Lys Ser Thr Asp Tyr His Gln Lys Arg Glu Thr Ile Arg
    50                  55                  60

Leu Val Thr Glu Glu Leu Tyr Leu Leu Ser Lys Arg Ile Asp Asp Asn
65                  70                  75                  80

Ile Leu Phe His Lys Thr Val Ile Ala Asn Ser Ser Ile Ile Ala Asp
                85                  90                  95

Met Ile Val Ser Leu Ser Leu Leu Glu Thr Leu Tyr Glu Met Lys Asp
            100                 105                 110
```

```
Val Val Glu Val Tyr Ser Arg Gln Cys Leu
        115                 120


<210> SEQ ID NO 28
<211> LENGTH: 583
<212> TYPE: PRT
<213> ORGANISM: Influenza B

<400> SEQUENCE: 28

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Asn Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asn Ala Glu Arg
    130                 135                 140

Ala Pro Gly Gly Pro Tyr Arg Leu Gly Thr Ser Gly Ser Cys Pro Asn
145                 150                 155                 160

Val Thr Ser Arg Asp Gly Phe Phe Ala Thr Met Ala Trp Ala Val Pro
                165                 170                 175

Arg Asp Asn Lys Thr Ala Thr Asn Pro Leu Thr Val Glu Val Pro Tyr
            180                 185                 190

Ile Cys Thr Lys Gly Glu Asp Gln Ile Thr Val Trp Gly Phe His Ser
        195                 200                 205

Asp Asp Lys Thr Gln Met Lys Asn Leu Tyr Gly Asp Ser Asn Pro Gln
    210                 215                 220

Lys Phe Thr Ser Ser Ala Asn Gly Val Thr Thr His Tyr Val Ser Gln
225                 230                 235                 240

Ile Gly Gly Phe Pro Asn Gln Thr Glu Asp Gly Gly Leu Pro Gln Ser
                245                 250                 255

Gly Arg Ile Val Val Asp Tyr Met Val Gln Lys Pro Gly Lys Thr Gly
            260                 265                 270

Thr Ile Val Tyr Gln Arg Gly Val Leu Leu Pro Gln Lys Val Trp Cys
        275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
```

```
        355                 360                 365

Phe Leu Glu Gly Gly Trp Glu Gly Met Ile Ala Gly Trp His Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580


<210> SEQ ID NO 29
<211> LENGTH: 466
<212> TYPE: PRT
<213> ORGANISM: Influenza B

<400> SEQUENCE: 29

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Glu Met Thr Leu Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Arg Gly Asn Ser Ala Pro
            100                 105                 110

Leu Thr Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140
```

```
Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Ile Lys Ile Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Ser Ala Ser Gly Ile Ser Lys Cys Arg Phe Leu Lys Ile
                245                 250                 255

Arg Glu Gly Arg Ile Ile Lys Glu Ile Phe Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Arg Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Glu Arg Met Gly Met Glu Leu Tyr Val Lys Tyr Asp
    370                 375                 380

Gly Asp Pro Trp Thr Asp Ser Glu Ala Leu Ala Pro Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Lys Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465
```

<210> SEQ ID NO 30
<211> LENGTH: 2305
<212> TYPE: DNA
<213> ORGANISM: Influenza B

<400> SEQUENCE: 30

```
agcagaagcg gtgcgtttga tttgccataa tggatacttt tattacaaga aacttccaga      60

ctacaataat acaaaaggcc aaaaacacaa tggcagaatt tagtgaagat cctgaattac     120

aaccagcaat gctattcaac atctgcgtcc atctagaggt ttgctatgta ataagtgaca     180

tgaattttct tgacgaagaa ggaaaatcat atacagcatt agaaggacaa ggaaaagaac     240
```

-continued

```
aaaacttgag accacaatat gaagtaattg agggaatgcc aagaaccata gcatggatgg    300
tccaaagatc cttagctcaa gagcatggaa tagagactcc aaagtatctg gctgatttgt    360
ttgattataa aaccaagaga tttatagaag ttggaataac aaaaggattg gctgatgatt    420
acttttggaa aaagaaagaa aagctgggaa atagcatgga actgatgata ttcagctaca    480
atcaagacta ttcgttaagt aatgaatcct cattggatga ggaagggaaa gggagagtgc    540
taagcagact cacagaactt caggctgaat taagtctgaa aaacctatgg caagttctca    600
taggagaaga agatgttgaa aagggaattg actttaaact tggacaaaca atatctagac    660
taagggatat atctgttcca gctggtttct ccaattttga aggaatgagg agctacatag    720
acaatataga tcctaaagga gcaatagaaa gaaatctagc aaggatgtct cccttagtat    780
cagccacacc taaaaagttg aaatgggagg acctaagacc aatagggcct cacatttaca    840
accatgagtt accagaagtt ccatataatg cctttcttct aatgtctgat gaattggggc    900
tggccaatat gactgaggga aagtccaaaa aaccgaagac attagccaaa gaatgtctag    960
aaaagtactc aacactacgg gatcaaactg acccaatatt aataatgaaa agcgaaaaag   1020
ctaacgaaaa tttcctatgg aagctgtgga gggactgtgt aaatacaata agtaatgagg   1080
aaatgagtaa cgagttacag aaaaccaatt atgccaagtg ggccacagga gatggattaa   1140
cataccagaa aataatgaaa gaagtagcaa tagatgacga aacaatgtgc caagaagagc   1200
ctaaaatccc taacaaatgt agagtggctg cttgggttca aacagagatg aatttattga   1260
gcactctgac aagtaaaaga gctctggacc taccagaaat agggccagac gtagcacccg   1320
tggagcatgt agggagtgaa agaaggaaat actttgttaa tgaaatcaac tgctgtaagg   1380
cctctacagt tatgatgaag tatgtgcttt ttcacacttc attattgaat gaaagcaatg   1440
ccagcatggg aaaatataaa gtaataccaa taaccaatag agtagtaaat gaaaaaggag   1500
aaagtttcga catgctttat ggtctggcgg ttaaaggaca atctcatctg aggggagata   1560
ctgatgttgt aacagttgtg actttcgaat ttagtggtac agatcccaga gtggactcag   1620
gaaagtggcc aaaatatact gtgtttagga ttggctccct atttgtgagt gggagggaaa   1680
aatctgtgta cctatattgc cgagtgaatg gcacaaataa gatccaaatg aaatggggaa   1740
tggaagctag aagatgtctg cttcaatcaa tgcaacaaat ggaagcaatt gttgaacaag   1800
aatcatcgat acaaggatat gacatgacca aagcttgttt caagggagac agagtaaata   1860
gccccaaaac ttttagtatt gggactcaag aaggaaaact agtaaaagga tcctttggga   1920
aagcactaag agtaatattt accaaatgtt tgatgcacta tgtatttgga aatgcccaat   1980
tggaggggtt tagtgccgag tctaggagac ttctactgtt aattcaagca ctaaaggaca   2040
gaaagggccc ttgggtgttc gacttagagg gaatgtattc tggaatagaa gaatgtatta   2100
gtaacaaccc ttgggtaata cagagtgcat actggttcaa tgaatggttg ggctttgaaa   2160
aggaggggag taaagtatta gaatcagtag atgaaataat gaatgaatga aaaaacatag   2220
tactcaattt ggtactattt tgttcattat gtatctaaac atccaataaa aagaatcgag   2280
aatcaaaaat gcacgtgttt ctact                                          2305
```

<210> SEQ ID NO 31
<211> LENGTH: 2369
<212> TYPE: DNA
<213> ORGANISM: Influenza B

<400> SEQUENCE: 31

```
agcagaagcg gagcctttaa gatgaatata aatccttatt ttctcttcat agatgtaccc     60
```

```
atacaggcag caatttcaac aacattccca tacaccggtg ttcccccctta ctcccatgga    120
acgggaacag gccacacaat agacaccgtg atcagaacac atgagtactc gaacaaggga    180
aaacagtatg tttctgacat cacaggatgt acaatggtag atccaacaaa tgggccatta    240
cccgaagaca atgagccgag tgcctatgca caattagatt gcgttctgga ggctttggat    300
agaatggatg aagaacatcc aggtttgttt caagcagcct cacagaatgc catggaggca    360
ctaatggtca caactgtaga caaattaacc caggggagac agacttttga ttggacagta    420
tgcagaaacc agcctgctgc aacggcacta aacacaacaa taacctcctt taggttgaat    480
gatttgaatg gagctgacaa gggtggattg gtacccttttt gccaagatat cattgattca    540
ttggacaaac ctgaaatgac tttcttctca gtaaagaata taaagaaaaa attgcctgct    600
aaaaacagaa agggtttcct cataaagaga ataccaatga aagtaaaaga caggataacc    660
agagtggaat acatcaaaag agcattatca ttaaacacaa tgacaaaaga tgctgaaagg    720
ggcaaactaa aaagaagagc gattgcaacc gctggaatac aaatcagagg gtttgtatta    780
gtagttgaaa acttggctaa aaatatctgt gaaaatctag aacaaagtgg tttgcccgta    840
ggtggaaatg aaaagaaggc caaactgtca aatgcagtgg ccaaaatgct cagtaactgc    900
ccaccaggag ggatcagcat gacagtaaca ggagacaata ctaaatggaa tgaatgctta    960
aatccaagaa tctttttggc tatgactgaa aggataacaa gagacagccc aatttggttc   1020
cgggattttt gtagtatagc accggtcttg ttctccaata aaatagccag attgggaaaa   1080
ggatttatga taacaagcaa aacaaaaaga ctgaaggctc aaataccttg tccagatctg   1140
tttagcatac cattagaaag atataatgaa gaaacaaggg caaaattaaa aaagctgaaa   1200
ccattcttca atgaagaagg aacggcatct ttgtcgcctg ggatgatgat gggaatgttt   1260
aatatgctat ctaccgtgtt gggagtagcc gcactaggta tcaaaaacat tggaaacaaa   1320
gaatatttat gggatggact gcaatcttct gatgattttg ctctgtttgt taatgcaaaa   1380
gatgaagaga catgtatgga aggaataaac gacttttacc gaacatgtaa attattggga   1440
ataaacatga gcaaaaagaa aagttactgt aatgaaactg gaatgtttga atttacaagc   1500
atgttctata gagatggatt tgtatctaat tttgcaatgg aaattccttc atttggagtt   1560
gctggagtaa atgaatcagc agatatggca ataggaatga caataataaa gaacaatatg   1620
atcaacaatg ggatgggtcc agcaacagca caaacagcca tacaattatt catagctgat   1680
tataggtaca cctacaaatg ccacagggga gattccaaag tggaaggaaa aagaatgaaa   1740
attataaagg agctatggga aaacactaaa ggaagagatg gtctgttagt ggcagatggt   1800
gggcccaaca tttacaattt gagaaactta catatcccag aaatagtatt gaagtacaac   1860
ctaatggacc ctgaatacaa agggcggtta cttcatcctc aaaatccatt tgtaggacat   1920
ttatctattg agggcatcaa agaagcagat ataaccccag cacatggtcc cgtaaagaaa   1980
atggattatg atgcagtatc tggaactcat agttggagaa ccaaaaggaa cagatctata   2040
ctaaatactg accagaggaa catgattctt gaggaacaat gctacgctaa gtgttgcaac   2100
ctttttgagg cctgttttaa tagtgcatca tacaggaaac cagtaggtca gcacagcatg   2160
cttgaggcta tggcccacag attaagagtg gatgcacgac tagattatga atcaggaaga   2220
atgtcaaagg atgattttga gaaagcaatg gctcaccttg gtgagattgg gtacatataa   2280
gctccgaaga tgtctatggg gttattggtc atcattgaat acatgtgata aacaaatgat   2340
taaaatgaaa aaaggctcgt gtttctact                                    2369
```

<210> SEQ ID NO 32
<211> LENGTH: 2396
<212> TYPE: DNA
<213> ORGANISM: Influenza B

<400> SEQUENCE: 32
agcagaagcg gagcgttttc aagatgacat tggctaaaat tgaattgtta aaacaactgt 60
taagggacaa tgaagccaaa acagtattga aacaaacaac ggtagaccaa tataacataa 120
taagaaaatt caatacatca agaattgaaa agaacccttc attgaggatg aagtgggcaa 180
tgtgttctaa ttttcccttg gctctgacca agggtgatat ggcaaacaga atccccttgg 240
aatacaaggg aatacaactt aaaacaaatg ctgaagacat aggaactaaa ggccaaatgt 300
gctcaatagc agcagttacc tggtggaata catatggacc aataggagat actgaaggtt 360
tcgaaaaggt ctacgaaagc ttttttctca gaaagatgag acttgacaat gccacttggg 420
gccgaataac ttttggccca gttgaaagag taagaaaaag ggtactgcta aaccctctca 480
ccaaggaaat gcctccagat gaagcaagta atgtgataat ggaaatattg ttccctaagg 540
aagcaggaat accaagagaa tctacttgga tacataggga actgataaaa gaaaaaagag 600
aaaaattgaa aggaacaatg ataactccca ttgtactggc atacatgctt gagagagaat 660
tggttgccag aagaaggttc ctgccggtgg caggagcaac atcagctgag ttcatagaaa 720
tgctacactg cttacaaggt gaaaattgga gacaaatata tcacccagga ggaaataaac 780
taactgaatc taggtctcaa tcgatgattg tagcttgtag aaagataatc agaagatcaa 840
tagtcgcatc aaacccatta gagctagctg tagaaattgc aaacaagact gtgatagata 900
ctgaaccttt aaaatcatgt ctgacagcca tagacggagg tgatgtagcc tgtgacataa 960
taagagctgc attaggacta aagatcagac aaagacaaag atttggacga cttgaactaa 1020
agagaatatc aggaagagga ttcaaaaatg atgaagaaat attaatcggg aacggaacaa 1080
tacagaagat tggaatatgg gacggagaag aggagttcca tgtaagatgt ggtgaatgca 1140
ggggaatatt aaaaaagagc aaaatgagaa tggaaaaact actaataaat tcagctaaaa 1200
aggaagacat gaaagattta ataatcttgt gcatggtatt ttctcaagac actaggatgt 1260
tccaaggagt gagaggagaa ataaattttc ttaatagagc aggccaactt ttatctccaa 1320
tgtaccaact ccaaagatat tttttgaata gaagcaacga tctctttgat caatgggggt 1380
atgaggaatc acccaaagca agtgagctac atggaataaa tgaattaatg aatgcatctg 1440
actacacttt gaaaggggtt gtagtaacaa aaaatgtaat tgatgatttt agttctactg 1500
aaacagaaaa agtatctata acaaaaaatc ttagtttaat aaaaaggact ggggaagtca 1560
taatgggggc taatgacgta agtgaattag aatcacaagc tcagctaatg ataacatatg 1620
atacacctaa gatgtgggag atgggaacaa ccaaagaact ggtgcaaaac acctaccaat 1680
gggtgctgaa aaatttggta acactgaagg ctcagtttct tctaggaaaa gaagacatgt 1740
tccaatggga tgcatttgaa gcatttgaaa gcataatccc ccagaagatg gctggccagt 1800
acagtggatt tgcaagagca gtgctcaaac aaatgagaga ccaagaggtt atgaaaactg 1860
accagttcat aaagttgttg cccttttgtt tctcaccacc aaaattaagg agaaatgggg 1920
agccttatca gttcttgagg cttgtattga agggaggagg agaaaatttc atcgaagtaa 1980
ggaaagggtc ccctctattc tcttacaatc cacaaacaga agtcctaact atatgcggca 2040
gaatgatgtc attaaaaggg aaaattgaag atgaagaaag gaatagatca atggggaatg 2100
cagtattagc gggctttctc gttagtggca agtatgaccc agatcttgga gatttcaaaa 2160
ctattgaaga acttgaaaag ctgaaaccgg gggagaaagc aaacatctta ctttatcaag 2220
gaaagcccgt taaagtagtt aaaaggaaaa gatatagtgc tttatccaat gacatttcac 2280
aaggaattaa gagacaaaga atgacagttg agtccatggg gtgggccttg agctaatata 2340
aatttatcca ttaattcaat aaacacaatt gagtgaaaaa tgctcgtgtt tctact 2396

<210> SEQ ID NO 33
<211> LENGTH: 1844
<212> TYPE: DNA
<213> ORGANISM: Influenza B

<400> SEQUENCE: 33
agcagaagca cagcattttc ttattaactt caagtaccaa caaaagaact gaaaatcaaa 60
atgtccaaca tggatattga cggtatcaac actgggacaa ttgacaaaac accggaagaa 120
ataacttctg gaaccagtgg gacaaccaga ccaatcatca gaccagcaac ccttgcccca 180
ccaagcaaca aacgaacccg gaacccatcc ccggaaagag caaccacaag cagtgaagct 240
gatgtcggaa ggaaaaccca aaagaaacag accccgacag agataaagaa gagcgtctac 300
aatatggtag tgaaactggg tgaattctat aaccagatga tggtcaaagc tggactcaac 360
gatgacatgg agagaaacct aatccaaaat gcgcatgctg tggaaagaat tctattggct 420
gccactgatg acaagaaaac tgaattccag aggaaaaaga atgccagaga tgtcaaagaa 480
ggaaaagaag aaatagacca caacaaaaca ggaggcacct tttacaagat ggtaagagat 540
gataaaacca tctacttcag ccctataaga attacctttt taaaagaaga ggtgaaaaca 600
atgtacaaaa ccaccatggg gagtgatggc ttcagtggac taaatcacat aatgattggg 660
cattcacaga tgaatgatgt ctgtttccaa agatcaaagg ccctaaaaag agttggactt 720
gacccttcat taatcagtac ctttgcagga agcacactcc ccagaagatc aggtgcaact 780
ggtgttgcaa tcaaaggagg tggaacttta gtggctgaag ccattcgatt tataggaaga 840
gcaatggcag acagagggct attgagagac atcaaagcca agactgccta tgaaaagatt 900
cttctgaatc taaaaaacaa atgctctgcg ccccaacaaa aggctctagt tgatcaagtg 960
atcggaagta gaaatccagg gattgcagac attgaagacc taaccctgct tgctcgtagt 1020
atggtcgttg ttaggccctc tgtggcgagc aaagtagtgc ttcccataag catttatgct 1080
aaaatacctc aactagggtt caatgttgaa gaatactcta tggttgggta tgaagccatg 1140
gctctctaca atatggcaac acctgtttcc atattaagaa tgggagatga tgcaaaagat 1200
aaatcgcaat tattcttcat gtcttgcttc ggagctgcct atgaagacct gagagttttg 1260
tctgcattaa caggcataga attcaagcct agatcagcat taaaatgcaa gggtttccat 1320
gttccagcaa aggaacaggt ggaaggaatg gggcagctc tgatgtccat caagctccag 1380
ttttgggctc caatgaccag atctggaggg aacgaagtag gtggagacgg agggtctggc 1440
caaataagtt gcagcccagt gtttgcagta gaaagaccta ttgctctaag caagcaagct 1500
gtaagaagaa tgctttcaat gaatattgag ggacgtgatg cagatgtcaa aggaaatcta 1560
ctcaagatga tgaatgactc aatggctaag aaaaccaatg gaaatgcttt cattgggaag 1620
aaaatgtttc aaatatcaga caaaaacaaa accaatcccg ttgaaattcc aattaagcag 1680
accatcccca atttcttctt tgggagggac acagcagagg attatgatga cctcgattat 1740
taaagcaaca aaatagacac tatgactgtg attgtttcaa tacgtttgga atgtgggtgt 1800
ttactcttat tgaaataaat ataaaaaatg ctgttgtttc tact 1844

<210> SEQ ID NO 34
<211> LENGTH: 1190
<212> TYPE: DNA
<213> ORGANISM: Influenza B

<400> SEQUENCE: 34
agcagaagca cgcactttct taaaatgtcg ctgtttggag acacaattgc ctacctgctt 60
tcattgacag aagatggaga aggcaaagca gaactagcag aaaaattaca ctgttggttc 120
ggtgggaaag aatttgacct agactctgcc ttggaatgga taaaaaacaa aagatgctta 180
actgatatac agaaagcact aattggtgcc tctatctgct tttaaaacc aaaagaccaa 240 gaaagaaaaa gaagattcat cacagagccc ctatcaggaa tgggaacaac agcaacaaaa 300
aagaagggcc tgattctagc tgagagaaaa atgagaagat gtgtgagttt tcatgaagca 360
tttgaaatag cagaaggcca tgaaagctca gcgctactat attgtctcat ggtcatgtac 420
ctgaaccctg gaaattattc aatgcaagta aaactaggaa cgctctgtgc tttgtgcgag 480
aaacaagcat cacattcaca cagggctcat agcagagcag caagatcttc agtgcctgga 540
gtgaggcgag aaatgcagat ggtctcagct atgaacacag caaaaacaat gaatggaatg 600
ggaaagggag aagacgtcca aaaactggca gaagagctgc aaagcaacat tggagtattg 660
agatctcttg ggcaagtcaa aaagaatggg gaaggaattg caaaggatgt gatggaagtg 720
ctaaagcaga gctctatggg aaattcagct cttgtgaaga aatacctata atgctcgaac 780
catttcagat tctttcaatt tgttctttca tcttatcagc tctccatttc atggcttgga 840
caatagggca tttgaatcaa ataaaaagag gagtaaacat gaaaatacga ataaaaaatc 900
caaataaaga gacaataaac agagaggtat caattttgag acacagttac caaaaagaaa 960
tccaggccaa agaaacaatg aaggaagtac tctctgacaa catggaggta ttgagtgacc 1020
acatagtaat tgaggggctt tctgctgaag agataataaa aatgggtgaa acagttttgg 1080
aggtagaaga attgcattaa attcaatttt tactgtattt cttgctatgc atttaagcaa 1140
attgtaatca atgtcagcaa ataaactgga aaaagtgcgt tgtttctact 1190

<210> SEQ ID NO 35
<211> LENGTH: 1096
<212> TYPE: DNA
<213> ORGANISM: Influenza B

<400> SEQUENCE: 35
agcagaagca gaggatttgt ttagtcactg gcaaacgaaa aaatggcgga caacatgacc 60
acaacacaaa ttgaggtggg tccgggagca accaatgcca ccataaactt tgaagcagga 120
attttggagt gctatgaaag gctttcatgg caaagagccc ttgactaccc tggtcaagac 180
cgcctaaaca aactaaagag aaaattggaa tcaagaataa agactcacaa caaaagtgag 240
ccagaaagta aaaggatgtc tcttgaagag agaaaagcta ttggggtaaa aatgatgaaa 300
gtgctcctat ttatgaaccc atctgctgga gttgaagggt ttgagccata ttgtatgaaa 360
aatccctcca atagcaactg tccagactgc aattgggctg attaccctcc aacaccagga 420
aagtaccttg atggcataga agaagaaccg gagaatgttg gtgactcaac tgaaatagta 480
ttaagggaca tgaacaacaa agatgcaagg caaaagataa aagaggaagt aaacactcag 540
aaagaaggga aattccgttt gacaataaaa agggatatac gtaatgtgtt gtccttgaga 600
gtgttggtaa acggaacatt catcaagcac cctaatggat acaagtcctt atcaactctg 660
catagattga atgcatatga ccagagtgga agacttgttg ctaaacttgt tgctactgat 720

```
gatcttacag tggaggatga agaagatggc catcggatcc tcaactcact cttcgagcgt    780

cttaatgaag gacattcaaa gccaattcga gcagctgaaa ctgcggtggg agtcttatcc    840

caatttggtc aagagcaccg attatcacca gaagagagag acaattagac tggttacgga    900

agaactttat cttttaagta aaagaattga tgataacata ttgttccaca aaacagtaat    960

agccaacagc tccataatag ctgacatgat tgtatcatta tcattattgg aaacattgta   1020

tgaaatgaag gatgtggttg aagtgtacag caggcagtgc ttgtgaattt aaaataaaaa   1080

tcctcttgtt actact                                                    1096
```

<210> SEQ ID NO 36
<211> LENGTH: 1557
<212> TYPE: DNA
<213> ORGANISM: Influenza B

<400> SEQUENCE: 36

```
agcagaagca gagcatcttc tcaaaactga ggcaaatagg ccaaaaatga acaatgctac     60

cttcaactat acaaacgtta accctatttc tcacatcagg gggagtgtta ttatcactat    120

atgtgtcagc ttcactatca tacttactgt attcggatat attgctaaaa ttttcaccaa    180

cagaaataac tgcaccaaca atgccattgg attgtgcaaa cgcatcaaat gttcaggctg    240

tgaaccgttc tgcaacaaaa gagatgacac ttcttctccc agaaccggag tggacatacc    300

ctcgtttatc ttgcccgggc tcaacctttc agaaagcact cctaattagc cctcatagat    360

tcggagaaac cagaggaaac tcagctccct tgacaataag ggaacctttt attgcttgtg    420

gaccaaagga atgcaaacac tttgctctaa cccattatgc agctcaacca gggggatact    480

acaatggaac aagagaggac agaaacaagc tgaggcatct gatttcagtc aaattgggca    540

aaataccaac agtagaaaac tccattttcc acatggcagc ttggagcggg tccgcatgcc    600

atgatggtag agaatggaca tatatcggag ttgatggccc tgacagtaat gcattgatca    660

aaataaaata tggagaagca tatactgaca cataccattc ctatgcaaac aacatcctaa    720

gaacacaaga aagtgcctgc aattgcattg gggagattg ttatcttatg ataactgatg    780

gctcagcttc aggaattagt aaatgcagat ttcttaagat tcgagagggt cgaataataa    840

aagaaatatt tccaacagga agagtagaac atactgaaga atgcacatgc ggatttgcca    900

gcaacaaaac catagaatgt gcctgtagag ataacagtta cacagcaaaa agaccctttg    960

tcaaattaaa tgtggagact gatacagctg aaataagatt gatgtgcaca gagacttatt   1020

tggacacccc cagaccagat gatggaagca taacagggcc ttgcgaatct aatggggaca   1080

aagggcgtgg aggcatcaag ggaggatttg ttcatcaaag aatggcatcc aagattggaa   1140

gatggtactc tcgaacgatg tctaaaactg aaagaatggg gatggaactg tatgtcaagt   1200

atgatggaga cccatggact gacagtgaag cccttgctcc tagtggagta atggtttcaa   1260

tggaagaacc tggttggtat tcttttggct tcgaaataaa agataagaaa tgtgatgtcc   1320

cctgtattgg gatagagatg gtacacgatg gtggaaaaaa gacttggcac tcagcagcaa   1380

cagccattta ctgtttaatg ggctcaggac aattgctatg ggacactgtc acaggtgttg   1440

atatggctct gtaatggagg aatggttgag tctgttctaa accctttgtt cctattttgt   1500

ttgaataatt gtccttactg aacttaattg tttctgaaaa atgctcttgt tactact      1557
```

<210> SEQ ID NO 37
<211> LENGTH: 1879
<212> TYPE: DNA

<213> ORGANISM: Influenza B

<400> SEQUENCE: 37
agcagaagca gagcattttc taatatccac aaaatgaagg caataattgt actactcatg 60
gtagtaacat ccaacgcaga tcgaatctgc actgggataa catcttcaaa ctcacctcat 120
gtggtcaaaa cagctactca aggggaagtc aatgtgactg gtgtgatacc actgacaaca 180
acaccaacaa aatctcattt tgcaaatcta aaaggaacaa agaccagagg gaaactatgc 240
ccaaactgtc tcaactgcac agatctggat gtggccttgg gcagaccaat gtgtgtgggg 300
accacacctt cggcaaaagc ttcaatactc cacgaagtca gacctgttac atccgggtgc 360
tttcctataa tgcacgacag aacaaaaatc agacagctac ccaatcttct cagaggatat 420
gaaaatatca gattatcaac ccaaaacgtt atcaacgcag aaagagcacc aggaggaccc 480
tacagacttg gaacctcagg atcttgccct aacgttacca gtagagacgg attcttcgca 540
acaatggctt gggctgtccc aagggacaac aaaacagcaa cgaatccact aacagtagaa 600
gtaccataca tttgtacaaa aggagaagac caaattactg tttgggggtt ccattctgat 660
gacaaaaccc aaatgaaaaa cctctatgga gactcaaatc ctcaaaagtt cacctcatct 720
gccaatggag taaccacaca ttatgtttct cagattggtg gcttcccaaa tcaaacagaa 780
gacggagggc taccacaaag cggcagaatt gttgttgatt acatggtgca aaaacctggg 840
aaaacaggaa caattgtcta tcaaagaggt gttttgttgc ctcaaaaggt gtggtgcgca 900
agtggcagga gcaaggtaat aaaagggtcc ttgcctttaa ttggtgaagc agattgcctt 960
cacgaaaaat acggtggatt aaacaaaagc aagccttact acacaggaga acatgcaaaa 1020
gccataggaa attgcccaat atgggtgaaa acacctttga agcttgccaa tggaaccaaa 1080
tatagacctc ctgcaaaact attaaaggaa aggggtttct tcggagctat tgctggtttc 1140
ttagaaggag gatgggaagg aatgattgca ggttggcacg gatacacatc tcatggagca 1200
catggagtgg cagtggcagc agaccttaag agtacgcaag aagccataaa caagataaca 1260
aaaaatctca attctttgag tgagctagaa gtaaagaatc ttcaaagact aagtggtgcc 1320
atggatgaac tccacaacga aatactcgag ctggatgaga aagtggatga tctcagagct 1380
gacacaataa gctcgcaaat agagcttgca gtcttgcttt ccaacgaagg aataataaac 1440
agtgaagatg agcatctatt ggcacttgag agaaaactaa agaaaatgct gggtccctct 1500
gctgtagaca tagggaatgg atgcttcgaa accaaacaca agtgcaacca gacctgctta 1560
gacagaatag ctgctggcac ctttaatgca ggagaatttt ctcttcccac ttttgattca 1620
ctgaatatta ctgctgcatc tttaaatgat gatggattgg ataatcatac tatactgctc 1680
tactactcaa ctgctgcttc tagtttggct gtaacattga tgatagctat ttttattgtt 1740
tatatggtct ccagagacaa tgtttcttgc tccatctgtc tataaggaaa attaagccct 1800
gtattttcct ttgttgtagt gcttgtttgc ttgttaccat tacaaagaaa cgttattgaa 1860
aaatgctctt gttactact 1879

<210> SEQ ID NO 38
<211> LENGTH: 1842
<212> TYPE: DNA
<213> ORGANISM: Influenza B

<400> SEQUENCE: 38
agcagaagca cagcattttc ttgtgaactt caagtaccaa caaaaactga aaatcaaaat 60
gtccaacatg gatattgacg gcatcaacac tggaacaatt gacaaaacac cagaagaaat 120

```
aacttccgga accagtgggg caaccagacc aatcatcaag ccagcaaccc ttgccccacc    180
aagcaataaa cgaacccgaa acccatcccc agaaagggca accacaagca gcgaagcgat    240
tgtcggaagg agaacccaaa agaaacaaac cccgacagag ataaagaaga gcgtctacaa    300
tatggtagtg aaactgggtg aattctacaa ccagatgatg gtcaaagctg gactcaacga    360
tgacatggag agaaacctaa tccaaaatgc acatgctgtg gaaagaattc tattggctgc    420
tactgatgac aagaaaactg aataccaaaa gaaaaagaat gccagagatg tcaaagaagg    480
gaaagaagaa atagaccaca acaaaacagg aggcaccttt tataagatgg taagagatga    540
taaaaccatc tacttcagcc ctataagaat taccttttta aaagaagagg tgaaaacaat    600
gtacaagacc accatgggga gtgatggttt cagtggacta aatcacatca tgattgggca    660
ttcacagatg aacgatgtct gtttccaaag atcaaaggca ctaaaaagag ttggacttga    720
cccttcatta atcagtactt ttgcaggaag cacactcccc agaagatcag gtgcaactgg    780
tgttgcgatc aaaggaggtg gaactttagt ggcagaagcc attcgattta taggaagagc    840
aatggcagac agagggctat tgagagacat cagagccaag acggcctatg aaaagattct    900
tctgaatctg aaaaacaagt gctctgcgcc ccaacaaaag gctctagttg atcaagtgat    960
cggaagtaga aacccaggga ttgcagacat agaagaccta accctgcttg cccgaagcat   1020
ggtcgttgtc aggccctctg tagcgagcaa agtggtgctt cccataagca ttaatgctaa   1080
aatacctcaa ctagggttca atgttgaaga atactctatg gttgggtatg aagccatggc   1140
tctttataat atggcaacac ctgtttccat attaagaatg ggagacgatg caaaagataa   1200
atcacaatta ttcttcatgt cttgctttgg agctgcctat gaagaccaaa gagttttgtc   1260
tgcactaacc ggcacagaat tcaagcctag gtcagcatta aagtgcaagg gtttccacgt   1320
tccagcaaag gagcaagtgg aaggaatggg ggcagctctg atgtccatca agctccagtt   1380
ttgggcccca atgaccagat ctgggggaa cgaagtaggt ggagacggag ggtctggtca    1440
aataagttgc agccccgtgt ttgcagtaga gagacctatt gctctaagca agcaagctgt   1500
aagaagaatg ctgtcaatga atattgaggg acgtgatgca gatgtcaaag gaaatctact   1560
caagatgatg aatgattcaa tggctaagaa aaccaatgga aatgctttca ttgggaagaa   1620
aatgtttcaa atatcagaca aaaacaaaat caatcccgtt gatattccaa ttaagcagac   1680
catccccaat ttcttctttg ggagggacac agcagaggat tatgatgacc tcgattatta   1740
aagcaacaaa atagacacta tggctgtgac tgtttcagta cgtttggaat gtgggtgttt   1800
actcttattg aaataaatgt aaaaaatgct gttgtttcta ct                      1842
```

<210> SEQ ID NO 39
<211> LENGTH: 1842
<212> TYPE: DNA
<213> ORGANISM: Influenza B

<400> SEQUENCE: 39

```
agcagaagca cagcattttc ttgtgaactt caagtaccaa caaaaactga aaatcaaaat     60
gtccaacatg gatattgacg gcatcaacac tggaacaatt gacaaaacac cagaagaaat    120
aacttccgga accagtgggg caaccagacc aatcatcaag ccagcaaccc ttgccccacc    180
aagcaataaa cgaacccgaa acccatcccc agaaagggca accacaagca gcgaagcgat    240
tgtcggaagg agaacccaaa agaaacaaac cccgacagag ataaagaaga gcgtctacaa    300
tatggtagtg aaactgggtg aattctacaa ccagatgatg gtcaaagctg gactcaacga    360
```

```
tgacatggag agaaacctaa tccaaaatgc acatgctgtg gaaagaattc tattggctgc    420
tactgatgac aagaaaactg aataccaaaa gaaaaagaat gccagagatg tcaaagaagg    480
gaaagaagaa atagaccaca acaaaacagg aggcaccttt tataagatgg taagagatga    540
taaaaccatc tacttcagcc ctataagaat taccttttta aaagaagagg tgaaaacaat    600
gtacaagacc accatgggga gtgatggttt cagtggacta aatcacatca tgattgggca    660
ttcacagatg aacgatgtct gtttccaaag atcaaaggca ctaaaaagag ttggacttga    720
cccttcatta atcagtactt ttgcaggaag cacactcccc agaagatcag gtgcaactgg    780
tgttgcgatc aaaggaggtg gaactttagt ggcagaagcc attcgattta taggaagagc    840
aatggcagac agagggctat tgagagacat cagagccaag acggcctatg aaaagattct    900
tctgaatctg aaaaacaagt gctctgcgcc ccaacaaaag gctctagttg atcaagtgat    960
cggaagtaga aacccaggga ttgcagacat agaagaccta accctgcttg cccgaagcat   1020
ggtcgttgtc aggccctctg tagcgagcaa agtggtgctt cccataagca ttaatgctaa   1080
aatacctcaa ctagggttca atgttgaaga atactctatg gttgggtatg aagccatggc   1140
tctttataat atggcaacac ctgtttccat attaagaatg ggagacgatg caaaagataa   1200
atcacaatta ttcttcatgt cttgctttgg agctgcctat gaagaccaaa gagttttgtc   1260
tgcactaacc ggcacagaat tcaagcctag gtcagcatta aagtgcaagg gtttccacgt   1320
tccagcaaag gagcaagtgg aaggaatggg ggcagctctg atgtccatca agctccagtt   1380
ttgggcccca atgaccagat ctgggggaa cgaagtaggt ggagacggag ggtctggtca   1440
aataagttgc agccccgtgt ttgcagtaga gagacctatt gctctaagca agcaagctgt   1500
aagaagaatg ctgtcaatga atattgaggg acgtgatgca gatgtcaaag gaaatctact   1560
caagatgatg aatgattcaa tggctaagaa aaccaatgga aatgctttca ttgggaagaa   1620
aatgtttcaa atatcagaca aaaacaaaat caatcccgtt gatattccaa ttaagcagac   1680
catccccaat ttcttctttg ggagggacac agcagaggat tatgatgacc tcgattatta   1740
aagcaacaaa atagacacta tggctgtgac tgtttcagta cgtttggaat gtgggtgttt   1800
actcttattg aaataaatgt aaaaaatgct gttgtttcta ct                      1842
```

<210> SEQ ID NO 40
<211> LENGTH: 2277
<212> TYPE: DNA
<213> ORGANISM: Influenza B

<400> SEQUENCE: 40

```
atggaaagaa taaaagagct aaggaatctg atgtcacaat ctcgcactcg cgagatactt     60
acaaaaacta ctgtagacca catggccata atcaagaaat acacatcagg aagacaggag    120
aaaaacccat cacttagaat gaaatggatg atggcaatga aataccaat tacagcagat    180
aaaaggataa cggaaatgat tcctgaaaga aatgagcaag gacagacatt atggagtaaa    240
gtgaatgatg ccggatcaga ccgagtgatg atatcacccc tggctgtgac atggtggaac    300
agaaatggac cagtggcaag tactattcac tatccaaaaa tctacaaaac ttactttgaa    360
aaggttgaaa ggttaaaaca tggaaccttt ggccctgtac actttagaaa ccaagtcaaa    420
atacgccgaa gagtcgacat aaatcctggt catgcagacc tcagcgccaa ggaggcacag    480
gatgtaatta tggaagttgt tttccctaat gaagtgggag ccagaatact aacatcagaa    540
tcgcaattaa cgataaccaa ggagaaaaaa gaagaactcc agaattgcaa aatttcccct    600
ttgatggttg catacatgtt agagagggaa cttgtccgca aaacgagatt tctcccggtt    660
```

gctggtggaa caagcagtgt gtacattgaa gttttgcatt taacacaggg gacatgctgg 720
gagcagatgt acactccagg tggggaggtg aggaatgatg atgttgatca aagcctaatt 780
attgctgcta ggaacatagt gagaagagct gcagtatcag cagatccact agcatcttta 840
ttagaaatgt gccatagcac acagattggt gggacaagga tggtggatat tctcaggcaa 900
aatccaacag aagaacaagc tgtggatata tgcaaagcag caatggggct gagaatcagt 960
tcatccttca gttttggcgg attcacattt aagagaacaa gtggatcatc agtcaaaagg 1020
gaggaagaag tgctcacggg caatctgcaa acattgaagc taactgtgca tgagggatat 1080
gaagagttca caatggttgg gaaaagggca acagctatac tcagaaaagc aaccaggaga 1140
ttgattcaac taatagtgag tggaagagac gaacagtcaa tagtcgaagc aatagttgta 1200
gcaatggtat tctcacaaga agattgcatg gtaaaagcag ttagaggtga tctgaatttc 1260
gttaatagag cgaatcagcg gttgaatccc atgcatcaac ttttgagaca ttttcagaag 1320
gatgctaaag tacttttctt aaattgggga attgaaccta tcgacaatgt gatgggaatg 1380
attgggatat tacctgatat gactccaagt accgagatgt caatgagagg agtgagagtc 1440
agcaaaatgg gtgtagatga atactccaat gctgaaaggg tagtggtgag cattgaccgt 1500
tttttgagag tccgggacca aagaggaaat gtactactgt ctccagagga agtcagtgaa 1560
acacagggaa cagagaaact gacaataact tactcttcat caatgatgtg ggagattaat 1620
ggccctgagt cagtgttgat caatacctat cagtggatca tcagaaactg ggagactgtt 1680
aaaattcagt ggtctcagaa ccctacaatg ctatacaata aaatggaatt cgagccattt 1740
cagtctctag tccctaaggc cattagaggc caatacagtg ggtttgttag aactctattt 1800
caacaaatga gggatgtgct tgggaccttt gacacaactc agataataaa acttcttccc 1860
tttgcagccg ctccaccaaa gcaaagtaga atgcaattct catcattgac tgtgaatgtg 1920
aggggatcag gaatgagaat acttgtaagg ggtaattctc cagtattcaa ctacaacaag 1980
accactaaga gactcacagt cctcggaaag gatgctggca ctttaactga agacccagat 2040
gaaggcacag ctggagtgga atctgctgtt ctaaggggat tcctcattct aggcaaagaa 2100
gatagaagat atgggccagc attaagcatc aatgaattga gcaaccttgc gaaaggggaa 2160
aaagctaatg tgctaattgg gcaaggggac gtagtgttgg taatgaaacg aaaacgggac 2220
tctagcatac ttactgacag ccagacagcg accaaaagaa ttcggatggc catcaat 2277

<210> SEQ ID NO 41
<211> LENGTH: 2277
<212> TYPE: DNA
<213> ORGANISM: Influenza B

<400> SEQUENCE: 41
atggaacgca ttaaagaact gcgcaacctg atgagccaga gccgcacccg cgaaattctg 60
accaaaacca ccgtggatca tatggcgatt attaaaaaat ataccagcgg ccgccaggaa 120
aaaaacccga gcctgcgcat gaaatggatg atggcgatga aatatccgat taccgcggat 180
aaacgcatta ccgaaatgat tccggaacgc aacgaacagg gccagaccct gtggagcaaa 240
gtgaacgatg cgggcagcga tcgcgtgatg attagcccgc tggcggtgac ctggtggaac 300
cgcaacggcc cggtggcgag caccattcat tatccgaaaa tttataaaac ctattttgaa 360
aaagtggaac gcctgaaaca tggcaccttt ggcccggtgc attttcgcaa ccaggtgaaa 420
attcgccgcc gcgtggatat taacccgggc catgcggatc tgagcgcgaa agaagcgcag 480

```
gatgtgatta tggaagtggt gtttccgaac gaagtgggcg cgcgcattct gaccagcgaa    540

agccagctga ccattaccaa agaaaaaaaa gaagaactgc agaactgcaa aattagcccg    600

ctgatggtgg cgtatatgct ggaacgcgaa ctggtgcgca aaacccgctt tctgccggtg    660

gcgggcggca ccagcagcgt gtatattgaa gtgctgcatc tgacccaggg cacctgctgg    720

gaacagatgt ataccccggg cggcgaagtg cgcaacgatg atgtggatca gagcctgatt    780

attgcggcgc gcaacattgt gcgccgcgcg gcggtgagcg cggatccgct ggcgagcctg    840

ctggaaatgt gccatagcac ccagattggc ggcacccgca tggtggatat tctgcgccag    900

aacccgaccg aagaacaggc ggtggatatt tgcaaagcgg cgatgggcct gcgcattagc    960

agcagcttta gctttggcgg ctttaccttt aaacgcacca gcggcagcag cgtgaaacgc   1020

gaagaagaag tgctgaccgg caacctgcag accctgaaac tgaccgtgca tgaaggctat   1080

gaagaattta ccatggtggg caaacgcgcg accgcgattc tgcgcaaagc gacccgccgc   1140

ctgattcagc tgattgtgag cggccgcgat gaacagagca ttgtggaagc gattgtggtg   1200

gcgatggtgt ttagccagga agattgcatg gtgaaagcgg tgcgcggcga tctgaacttt   1260

gtgaaccgcg cgaaccagcg cctgaacccg atgcatcagc tgctgcgcca ttttcagaaa   1320

gatgcgaaag tgctgtttct gaactggggc attgaaccga ttgataacgt gatgggcatg   1380

attggcattc tgccggatat gaccccgagc accgaaatga gcatgcgcgg cgtgcgcgtg   1440

agcaaaatgg gcgtggatga atatagcaac gcggaacgcg tggtggtgag cattgatcgc   1500

tttctgcgcg tgcgcgatca gcgcggcaac gtgctgctga gcccggaaga agtgagcgaa   1560

acccagggca ccgaaaaact gaccattacc tatagcagca gcatgatgtg ggaaattaac   1620

ggcccggaaa gcgtgctgat taacacctat cagtggatta ttcgcaactg ggaaaccgtg   1680

aaaattcagt ggagccagaa cccgaccatg ctgtataaca aaatggaatt tgaaccgttt   1740

cagagcctgg tgccgaaagc gattcgcggc cagtatagcg gctttgtgcg caccctgttt   1800

cagcagatgc gcgatgtgct gggcaccttt gataccaccc agattattaa actgctgccg   1860

tttgcggcgg cgccgccgaa acagagccgc atgcagttta gcagcctgac cgtgaacgtg   1920

cgcggcagcg gcatgcgcat tctggtgcgc ggcaacagcc cggtgtttaa ctataacaaa   1980

accaccaaac gcctgaccgt gctgggcaaa gatgcgggca ccctgaccga agatccggat   2040

gaaggcaccg cgggcgtgga aagcgcggtg ctgcgcggct ttctgattct gggcaaagaa   2100

gatcgccgct atggcccggc gctgagcatt aacgaactga gcaacctggc gaaaggcgaa   2160

aaagcgaacg tgctgattgg ccagggcgat gtggtgctgg tgatgaaacg caaacgcgat   2220

agcagcattc tgaccgatag ccagaccgcg accaaacgca ttcgcatggc gattaac      2277
```

```
<210> SEQ ID NO 42
<211> LENGTH: 585
<212> TYPE: PRT
<213> ORGANISM: Influenza B

<400> SEQUENCE: 42

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60
```

-continued

```
Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asp Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480
```

-continued

```
Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585
```

<210> SEQ ID NO 43
<211> LENGTH: 1812
<212> TYPE: DNA
<213> ORGANISM: Influenza B

<400> SEQUENCE: 43

```
agcattttct tgtgagcttc gagcactaat aaaactgaaa atcaaaatgt ccaacatgga     60
tattgacagt ataaataccg gaacaatcga taaaaaacca gaagaactga ctcccggaac    120
cagtggggca accagaccaa tcatcaagcc agcaaccctt gctccgccaa gcaacaaacg    180
aacccgaaat ccatccccag aaaggacaac cacaagcagt gaaaccgata tcggaaggaa    240
aatccaaaag aaacaaaccc caacagagat aaagaagagc gtctacaaca tggtggtaaa    300
gctgggtgaa ttctacaacc agatgatggt caaagctgga cttaatgatg acatggaaag    360
gaatctaatc caaaatgcac aagctgtgga gagaatccta ttggctgcaa ctgatgacaa    420
gaaaactgaa taccaaaaga aaaggaatgc cagagatgtc aaagaaggga aggaagaaat    480
agaccacaac aagacaggag gcacctttta taagatggta agagatgata aaaccatcta    540
cttcagccct ataaaaatta cctttttaaa agaagaggtg aaaacaatgt acaagaccac    600
catggggagt gatggtttca gtggactaaa tcacattatg attggacatt cacagatgaa    660
cgatgtctgt ttccaaagat caaaggcact gaaaagggtt ggacttgacc cttcattaat    720
cagtactttt gccggaagca cactacccag aagatcaggt acaactggtg ttgcaatcaa    780
aggaggtgga actttagtgg cagaagccat tcgattttata ggaagagcaa tggcagacag    840
agggctactg agagacatca aggccaagac agcctatgaa aagattcttc tgaatctgaa    900
aaacaagtgc tctgcgcccc aacaaaaggc tctagttgat caagtgatcg gaagtaggaa    960
cccagggatt gcagacatag aagacctaac tctgcttgcc agaagcatga tagttgtcag   1020
accctctgta gcgagcaaag tggtgcttcc cataagcatt tatgctaaaa tacctcaact   1080
aggattcaat atcgaagaat actctatggt tgggtatgaa gccatggctc tttataatat   1140
ggcaacacct gtttccatat taagaatggg agatgacgca aaagataaat ctcaactatt   1200
cttcatgtcg tgcttcggag ctgcctatga agatctaaga gtgttatctg cactaacggg   1260
caccgaattt aagcctagat cagcactaaa atgcaagggt ttccatgtcc cggctaagga   1320
gcaagtagaa ggaatggggg cagctctgat gtccatcaag cttcagttct gggccccaat   1380
gaccagatct ggagggaatg aagtaagtgg agaaggaggg tctggtcaaa taagttgcag   1440
ccctgtgttt gcagtagaaa gacctattgc tctaagcaag caagctgtaa gaagaatgct   1500
```

-continued gtcaatgaac gttgaaggac gtgatgcaga tgtcaaagga aatctactca aaatgatgaa 1560
tgattcgatg gcaaagaaaa ccagtggaaa tgctttcatt gggaagaaaa tgtttcaaat 1620
atcagacaaa aacaaagtca atcccattga gattccaatt aagcagacca tccccagttt 1680
cttctttggg agggacacag cagaggatta tgatgacctc gattattaaa gcaataaaat 1740
agacactatg gctgtgactg tttcagtacg tttgggatgt gggtgtttac tcttattgaa 1800
ataaatgtaa aa 1812

<210> SEQ ID NO 44
<211> LENGTH: 560
<212> TYPE: PRT
<213> ORGANISM: Influenza B

<400> SEQUENCE: 44

```
Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Ala Thr Arg Pro Ile
            20                  25                  30

Ile Lys Pro Ala Thr Leu Ala Pro Pro Ser Asn Lys Arg Thr Arg Asn
        35                  40                  45

Pro Ser Pro Glu Arg Ala Thr Thr Ser Ser Glu Ala Ile Val Gly Arg
    50                  55                  60

Arg Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Tyr Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Leu Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Arg
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320
```

Met Val Val Val Arg Pro Ser Val Ala Ser Lys Val Val Leu Pro Ile
325 330 335

Ser Ile Asn Ala Lys Ile Pro Gln Leu Gly Phe Asn Val Glu Glu Tyr
340 345 350

Ser Met Val Gly Tyr Glu Ala Met Ala Leu Tyr Asn Met Ala Thr Pro
355 360 365

Val Ser Ile Leu Arg Met Gly Asp Asp Ala Lys Asp Lys Ser Gln Leu
370 375 380

Phe Phe Met Ser Cys Phe Gly Ala Ala Tyr Glu Asp Gln Arg Val Leu
385 390 395 400

Ser Ala Leu Thr Gly Thr Glu Phe Lys Pro Arg Ser Ala Leu Lys Cys
405 410 415

Lys Gly Phe His Val Pro Ala Lys Glu Gln Val Glu Gly Met Gly Ala
420 425 430

Ala Leu Met Ser Ile Lys Leu Gln Phe Trp Ala Pro Met Thr Arg Ser
435 440 445

Gly Gly Asn Glu Val Gly Gly Asp Gly Gly Ser Gly Gln Ile Ser Cys
450 455 460

Ser Pro Val Phe Ala Val Glu Arg Pro Ile Ala Leu Ser Lys Gln Ala
465 470 475 480

Val Arg Arg Met Leu Ser Met Asn Ile Glu Gly Arg Asp Ala Asp Val
485 490 495

Lys Gly Asn Leu Leu Lys Met Met Asn Asp Ser Met Ala Lys Lys Thr
500 505 510

Asn Gly Asn Ala Phe Ile Gly Lys Lys Met Phe Gln Ile Ser Asp Lys
515 520 525

Asn Lys Ile Asn Pro Val Asp Ile Pro Ile Lys Gln Thr Ile Pro Asn
530 535 540

Phe Phe Phe Gly Arg Asp Thr Ala Glu Asp Tyr Asp Asp Leu Asp Tyr
545 550 555 560

<210> SEQ ID NO 45
<211> LENGTH: 560
<212> TYPE: PRT
<213> ORGANISM: Influenza B

<400> SEQUENCE: 45

Met Ser Asn Met Asp Ile Asp Gly Ile Asn Thr Gly Thr Ile Asp Lys
1 5 10 15

Thr Pro Glu Glu Ile Thr Ser Gly Thr Ser Gly Ala Thr Arg Pro Ile
20 25 30

Ile Lys Pro Ala Thr Leu Ala Pro Pro Ser Asn Lys Arg Thr Arg Asn
35 40 45

Pro Ser Pro Glu Arg Ala Ala Thr Ser Ser Glu Ala Asp Val Gly Arg
50 55 60

Arg Thr Gln Lys Lys Gln Thr Pro Thr Glu Ile Lys Lys Ser Val Tyr
65 70 75 80

Asn Met Val Val Lys Leu Gly Glu Phe Tyr Asn Gln Met Met Val Lys
85 90 95

Ala Gly Leu Asn Asp Asp Met Glu Arg Asn Leu Ile Gln Asn Ala His
100 105 110

Ala Ala Glu Arg Ile Leu Leu Ala Ala Thr Asp Asp Lys Lys Thr Glu
115 120 125

Phe Gln Lys Lys Lys Asn Ala Arg Asp Val Lys Glu Gly Lys Glu Glu

-continued

```
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Leu Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Arg
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Asn Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Gln Arg Val Leu
385                 390                 395                 400

Ser Ala Leu Thr Gly Thr Glu Phe Lys His Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Thr Lys Lys Thr
            500                 505                 510

Asn Gly Asn Ala Phe Ile Gly Lys Lys Met Phe Gln Ile Ser Asp Lys
        515                 520                 525
```

-continued

```
Asn Lys Thr Asn Pro Ile Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560
```